US011186580B2

(12) United States Patent
Douty et al.

(10) Patent No.: US 11,186,580 B2
(45) Date of Patent: Nov. 30, 2021

(54) CRYSTALLINE FORMS OF A PHOSPHOINOSITIDE 3-KINASE (PI3K) INHIBITOR

(71) Applicant: Incyte Corporation, Wilmington, DE (US)

(72) Inventors: Brent Douty, Fallowfield, PA (US); David M. Burns, Plymouth Meeting, PA (US); Andrew P. Combs, Kennett Square, PA (US); Zhongjiang Jia, Kennett Square, PA (US); Daniel Levy, Philadelphia, PA (US); Eddy W. Yue, Landenberg, PA (US)

(73) Assignee: Incyte Corporation, Wilmington, DE (US)

(*) Notice: Subject to any disclaimer, the term of this patent is extended or adjusted under 35 U.S.C. 154(b) by 107 days.

(21) Appl. No.: 16/560,087

(22) Filed: Sep. 4, 2019

(65) Prior Publication Data
US 2020/0071335 A1 Mar. 5, 2020

Related U.S. Application Data

(60) Provisional application No. 62/746,928, filed on Oct. 17, 2018, provisional application No. 62/727,321, filed on Sep. 5, 2018, provisional application No. 62/727,328, filed on Sep. 5, 2018, provisional application No. 62/727,339, filed on Sep. 5, 2018.

(51) Int. Cl.
C07D 487/04 (2006.01)
A61K 31/4188 (2006.01)

(52) U.S. Cl.
CPC ........ C07D 487/04 (2013.01); C07B 2200/13 (2013.01)

(58) Field of Classification Search
CPC ............... C07D 487/04; A61K 31/4188
See application file for complete search history.

(56) References Cited

U.S. PATENT DOCUMENTS

| 4,269,846 | A | 5/1981 | Huang et al. |
|---|---|---|---|
| 5,137,876 | A | 8/1992 | MacCoss et al. |
| 5,521,184 | A | 5/1996 | Zimmermann |
| 7,186,832 | B2 | 3/2007 | Sun |
| 7,511,145 | B2 | 3/2009 | Schmitz et al. |
| 8,329,697 | B2 | 12/2012 | Garbaccio et al. |
| 8,680,108 | B2 | 3/2014 | Li et al. |
| 8,759,359 | B2 | 6/2014 | Combs et al. |
| 8,940,752 | B2 | 1/2015 | Li et al. |
| 9,062,055 | B2 | 6/2015 | Li et al. |
| 9,096,600 | B2 | 8/2015 | Li et al. |
| 9,108,984 | B2 | 8/2015 | Combs et al. |
| 9,126,948 | B2 | 9/2015 | Combs et al. |
| 9,193,721 | B2 | 11/2015 | Combs et al. |
| 9,199,982 | B2 | 12/2015 | Li et al. |
| 9,586,949 | B2 | 3/2017 | Zou et al. |
| 10,022,387 | B2 | 7/2018 | Zou et al. |
| 10,065,963 | B2 | 9/2018 | Shvartsbart et al. |
| 10,138,248 | B2 | 11/2018 | Buesking et al. |
| 10,472,368 | B2 | 11/2019 | Shvartsbart et al. |
| 10,479,795 | B2 | 11/2019 | Buesking et al. |
| 10,738,057 | B2 | 8/2020 | Douty et al. |
| 2004/0220189 | A1 | 11/2004 | Sun et al. |
| 2005/0009832 | A1 | 1/2005 | Sun et al. |
| 2007/0099925 | A1 | 5/2007 | Calderwood et al. |
| 2007/0225286 | A1 | 9/2007 | Ren et al. |
| 2010/0298334 | A1 | 11/2010 | Rodgers et al. |
| 2011/0015212 | A1 | 1/2011 | Li et al. |
| 2011/0059951 | A1 | 3/2011 | Rodgers et al. |
| 2011/0224190 | A1 | 9/2011 | Huang et al. |
| 2012/0149681 | A1 | 6/2012 | Rodgers et al. |
| 2012/0149682 | A1 | 6/2012 | Rodgers et al. |
| 2012/0157430 | A1 | 6/2012 | Li et al. |
| 2012/0238564 | A1 | 9/2012 | Luk et al. |
| 2012/0329792 | A1 | 12/2012 | Bartolome-Nebreda et al. |
| 2013/0018034 | A1 | 1/2013 | Yao et al. |
| 2013/0045963 | A1 | 2/2013 | Rodgers et al. |
| 2013/0059835 | A1 | 3/2013 | Li et al. |
| 2013/0261101 | A1 | 10/2013 | Combs et al. |
| 2014/0005166 | A1 | 1/2014 | Rodgers et al. |
| 2014/0121198 | A1 | 5/2014 | Li et al. |
| 2014/0249132 | A1 | 9/2014 | Li et al. |
| 2014/0275127 | A1 | 9/2014 | Combs et al. |
| 2014/0343030 | A1 | 11/2014 | Li et al. |
| 2015/0005309 | A1 | 1/2015 | Barfacker et al. |
| 2015/0284390 | A1 | 10/2015 | Li et al. |

(Continued)

FOREIGN PATENT DOCUMENTS

| CL | 201902324 | 11/2019 |
|---|---|---|
| CL | 202000215 | 8/2020 |

(Continued)

OTHER PUBLICATIONS

Atzrodt et al., "The Renaissance of H/D Exchange," Angew Chem Int Ed., Oct. 4, 2007, 46(41):7744-7765.
Bala et al., "Highly efficient water-mediated approach to access benzazoles: metal catalyst and base-free synthesis of 2-substituted benzimidazoles, benzoxazoles, and benzothiazoles," Molecular Diversity, Mar. 2015, 19(2):263-272.
Barber et al., "PI3Kgamma inhibition blocks glomerulonephritis and extends lifespan in a mouse model of systemic lupus," Nat Medicine, Sep. 2005, 11(9):933-935.
Berge et al., "Pharmaceutical Salts," Journal of Pharmaceutical Science, 1977, 66(2): 1-19.

(Continued)

Primary Examiner — Karen Cheng
(74) Attorney, Agent, or Firm — Fish & Richardson P.C.

(57) ABSTRACT

The present invention relates to salts and crystalline forms of 2-(3-(8-Amino-6-(trifluoromethyl)imidazo[1,2-a]pyrazin-3-yl)-4-methylphenyl)-3,3,3-trifluoro-2-hydroxypropanamide, crystalline forms of 8-amino-N-(2-hydroxy-2-methylpropyl)-3-(2-methyl-5-(1,1,1-trifluoro-2-hydroxypropan-2-yl)phenyl)imidazo[1,2-a]pyrazine-6-carboxamide, and crystalline forms of 8-amino-N-(2-hydroxy-2-methylpropyl)-3-(2-(methyl-$d_3$)-5-(1,1,1-trifluoro-2-hydroxypropan-2-yl)phenyl)imidazo[1,2-a]pyrazine-6-carboxamide, which are PI3K inhibitors useful in the treatment of cancer and other diseases.

31 Claims, 17 Drawing Sheets

(56) References Cited

U.S. PATENT DOCUMENTS

| | | |
|---|---|---|
| 2015/0361094 A1 | 12/2015 | Li et al. |
| 2016/0000795 A1 | 1/2016 | Scherle et al. |
| 2016/0022685 A1 | 1/2016 | Li et al. |
| 2016/0024117 A1 | 1/2016 | Li et al. |
| 2017/0129899 A1 | 5/2017 | Shvartsbart et al. |
| 2017/0190689 A1 | 7/2017 | Sparks et al. |
| 2018/0009816 A1 | 1/2018 | Buesking et al. |
| 2018/0057469 A1 | 3/2018 | Wu et al. |
| 2019/0060331 A1 | 2/2019 | Zou et al. |
| 2019/0062336 A1 | 2/2019 | Shvartsbart et al. |
| 2019/0119287 A1 | 4/2019 | Buesking et al. |
| 2019/0152975 A1 | 5/2019 | Douty et al. |
| 2019/0359592 A1 | 11/2019 | Sparks et al. |
| 2020/0385392 A1 | 12/2020 | Douty et al. |

FOREIGN PATENT DOCUMENTS

| | | |
|---|---|---|
| CL | 202001680 | 9/2020 |
| CL | 202000664 | 11/2020 |
| CL | 202001501 | 11/2020 |
| CL | 202001632 | 11/2020 |
| CL | 202001009 | 12/2020 |
| EP | 2044051 | 1/2010 |
| WO | WO 00/009495 | 2/2000 |
| WO | WO 00/053595 | 9/2000 |
| WO | WO 01/014402 | 3/2001 |
| WO | WO 01/064655 | 9/2001 |
| WO | WO 2001/085724 | 11/2001 |
| WO | WO 2002/000196 | 1/2002 |
| WO | WO 03/024967 | 3/2003 |
| WO | WO 03/037347 | 5/2003 |
| WO | WO 2003/035065 | 5/2003 |
| WO | WO 2003/035644 | 5/2003 |
| WO | WO 2003/068225 | 8/2003 |
| WO | WO 03/099771 | 12/2003 |
| WO | WO 2004/005281 | 1/2004 |
| WO | WO 2004/046120 | 6/2004 |
| WO | WO 2004/056786 | 7/2004 |
| WO | WO 2004/078943 | 9/2004 |
| WO | WO 2004/080980 | 9/2004 |
| WO | WO 2005/012288 | 2/2005 |
| WO | WO 2005/028444 | 3/2005 |
| WO | WO 2005/118580 | 12/2005 |
| WO | WO 2006/056399 | 6/2006 |
| WO | WO 2007/019416 | 2/2007 |
| WO | WO 2007/019417 | 2/2007 |
| WO | WO 2007/028051 | 3/2007 |
| WO | WO 2009/005551 | 1/2009 |
| WO | WO 2009/016118 | 2/2009 |
| WO | WO 2009/024585 | 2/2009 |
| WO | WO 2009/064835 | 5/2009 |
| WO | WO 2009/079011 | 6/2009 |
| WO | WO 2009/114512 | 9/2009 |
| WO | WO 2009/123776 | 10/2009 |
| WO | WO 2009/133127 | 11/2009 |
| WO | WO 2009/158118 | 12/2009 |
| WO | WO 2010/051245 | 5/2010 |
| WO | WO 2010/061903 | 6/2010 |
| WO | WO 2010/069684 | 6/2010 |
| WO | WO 2010/135014 | 11/2010 |
| WO | WO 2011/099832 | 8/2011 |
| WO | WO 2011/123609 | 10/2011 |
| WO | WO 2011/149856 | 12/2011 |
| WO | WO 2011/149874 | 12/2011 |
| WO | WO 2012/051410 | 4/2012 |
| WO | WO 2012/074126 | 6/2012 |
| WO | WO 2012/143796 | 10/2012 |
| WO | WO 2012/170867 | 12/2012 |
| WO | WO 2013/104610 | 7/2013 |
| WO | WO 2013/129674 | 9/2013 |
| WO | WO 2013/180193 | 12/2013 |
| WO | WO 2014/009295 | 1/2014 |
| WO | WO 2014/149207 | 9/2014 |
| WO | WO 2014/153529 | 9/2014 |
| WO | WO 2014/182954 | 11/2014 |
| WO | WO 2015/008872 | 1/2015 |
| WO | WO 2015/051241 | 4/2015 |
| WO | WO 2015/154878 | 10/2015 |
| WO | WO 2016/044342 | 3/2016 |
| WO | WO 2016/064957 | 4/2016 |
| WO | WO 2016/075130 | 5/2016 |
| WO | WO 2016/166239 | 10/2016 |
| WO | WO 2017/223414 | 12/2017 |
| WO | WO 2018/038265 | 3/2018 |

OTHER PUBLICATIONS

Berod et al., "PI3Kγ deficiency delays the onset of experimental autoimmune encephalomyelitis and ameliorates its clinical outcome," Euro J Immunol., Mar. 2011, 41(3):833-844.

Blom et al., "Preparative LC-MS Purification: Improved Compound Specific Method Optimization," J Comb Chem., 2004, 6(6): 874-883.

Blom et al., "Two-Pump At Column Dilution Configuration for Preparative LC-MS," J Comb. Chem., Jul.-Aug. 2002, 4(295):295-301.

Blom et al., "Optimizing Preparative LC-MS Configurations and Methods for Parallel Synthesis Purification," J Comb Chem., 2003, 5(5):670-683.

Brock et al., "Roles of G beta gamma in membrane recruitment and activation of p110 gamma/p101 phosphoinositide 3-kinase gamma," J Biol Chem., Jan. 6, 2003, 160(1):89-99.

Bruneau et al., "2-Aminobiphenyl Palladacycles: The "Most Powerful" Precatalysts in C—C and C-Heteroatom Cross-Couplings," ACS Catal., 2015, 5(2):1386-1396.

Buesking et al., "Asymmetric Synthesis of Protected α-Amino Boronic Acid Derivatives with an Air- and Moisture-Stable Cu(II) Catalyst," J Org Chem., Mar. 31, 2014, 79(8):3671-3677.

Camps et al., "Blockade of PI3Kγ suppresses joint inflammation and damage in mouse models of rheumatoid arthritis," Nat Medicine., 2005, 11(9):939-943.

Cantley, "The phosphoinositide 3-kinase pathway," Science, May 31, 2002, 296(5573)4655-1657.

Carter et al., "Prioritization of driver mutations in pancreatic cancer using cancer-specific high-throughput annotation of somatic mutations (CHASM)," Cancer Biol Ther., Sep. 15, 2010, 10(6):582-587.

Choudhury-Mukherjee et al., "Design, synthesis, and evaluation of analogues of 3,3,3-trifluoro-2-hydroxy-2-phenyl-propionamide as orally available general anesthetics," J Med Chem, Jun. 5, 2003, 46(12):2494-2501.

Collier et al., "Discovery of Highly Isoform Selective Thiazolopiperidine Inhibitors of Phosphoinositide 3-Kinase γ," Journal of Medicinal Chemistry, Jul. 26, 2015, 58:5684-5688.

Collier et al., "Structural Basis for Isoform Selectivity in a Class of Benzothiazole Inhibitors of Phosphoinositide 3-Kinase [gamma]," Journal of Medicinal Chemistry, Jan. 2015, 58(1):517-521.

Comerford et al., "PI3Kγ Drives Primin and Survival of Autoreactive CD4+ T Cells during Experimental Autoimmune Encephalomyelitis," PLOS one, Sep. 2012, 7(9):e450095.

Cossy et al., "Formation of optically active 3-hydroxypiperidines," Tetrahedron Letters, Jan. 23, 1995, 36(4):549-552.

Cushing et al., "PI3Kδ and PI3Kγ as Targets for Autoimmune and Inflammatory Diseases," Journal of Medicinal Chemistry, Sep. 13, 2012, 55:8559-8581.

Database Registry [online], Chemical Abstracts Service, Columbus, OH, US, Jun. 1, 2015, Chemical Catalog; Supplier: Aurora Fine Chemicals: XP002755361, Database Accession No. 1770353-29-1.

Database Registry [online], Chemical Abstracts Service, Columbus, OH, US, Jun. 4, 2015, Chemical Catalog; Supplier: Aurora Fine Chemicals: XP002755362, Database Accession No. 1773443-64-3.

Database Registry [online], Chemical Abstracts Service, Columbus, OH, US, May 29, 2015, Chemical Catalog; Supplier: Aurora Fine Chemicals: XP002755360, Database Accession No. 1715195-44-0.

Database Registry [online], Chemical Abstracts Service, Columbus, OH, US; Aug. 2012, CAS client services: XP002755356, Database accession No. 1391828-67-3.

(56) References Cited

OTHER PUBLICATIONS

Database Registry [online], Chemical Abstracts Service, Columbus, OH, US; Dec. 2011, Chemical Catalog; Supplier: Ukrorgsyntez ltd.: XP002755357, Database accession No. 1347088-14-5.

Database Registry [online], Chemical Abstracts Service, Columbus, OH, US; Dec. 2012, Chemical Catalog; Supplier: Aurora Fine Chemicals: XP002755355, Database accession No. 1411464-90-8.

Database Registry [online], Chemical Abstracts Service, Columbus, OH, US; Feb. 2014, Chemical Catalog; Supplier: Aurora Fine Chemicals: XP002755346, Database accession No. 1554931-95-1.

Database Registry [online], Chemical Abstracts Service, Columbus, OH, US; Feb. 2014, Chemical Catalog; Supplier: Aurora Fine Chemicals: XP002755347, Database accession No. 1540856-06-1.

Database Registry [online], Chemical Abstracts Service, Columbus, OH, US; Feb. 2014, Chemical Catalog; Supplier: Aurora Fine Chemicals: XP002755349, Database accession No. 1538237-68-1.

Database Registry [online], Chemical Abstracts Service, Columbus, OH, US; Feb. 2014, Chemical Catalog; Supplier: Aurora Fine Chemicals: XP002755350, Database accession No. 1536955-67-5.

Database Registry [online], Chemical Abstracts Service, Columbus, OH, US; Jan. 2014, Chemical Catalog; Supplier: Aurora Fine Chemicals: XP002755351, Database accession No. 1528719-88-1.

Database Registry [online], Chemical Abstracts Service, Columbus, OH, US; Jan. 2014, Chemical Catalog; Supplier: Aurora Fine Chemicals: XP002755352, Database accession No. 1526778-80-2.

Database Registry [online], Chemical Abstracts Service, Columbus, OH, US; Jan. 2014, Chemical Catalog; Supplier: Aurora Fine Chemicals: XP002755353, Database accession No. 1522493-70-4.

Database Registry [online], Chemical Abstracts Service, Columbus, OH, US; Jan. 2014, Chemical Catalog; Supplier: Aurora Fine Chemicals: XP002755354, Database accession No. 1520181-20-7.

Database Registry [online], Chemical Abstracts Service, Columbus, OH, US; Oct. 2005, Chemical Library; Supplier: interchim: XP002755358, Database accession No. 866138-38-7.

Database Registry [online], Chemical Abstracts Service, Columbus, OH, US; Oct. 2005, Chemical Libraiy; Supplier: interchim: XP002755359, Database accession No. 864939-76-4.

Database Registry [online], Chemical Abstracts Service, Columbus, Ohio, US, Feb. 2010, Chemical Catalog; Supplier: Aurora Fine Chemicals: XP002755348, Database accession No. 1540777-22-7.

Doukas et al., "Aerosolized phosphoinositide 3-kinase gamma/delta inhibitor TG100-115 [3-[2,4-diamino-6-(3-hydroxyphenyl)pteridin-7-yl]phenol] as a therapeutic candidate for asthma and chronic obstructive pulmonary disease," J Pharmacol Exp Ther., Mar. 2009, 328(3):758-765.

Doukas et al., "Phosphoinositide 3-kinase gamma/delta inhibition limits infarct size after myocardial ischemia/reperfusion injury," Proc Natl Acad Sci USA., Dec. 26, 2006, 103(52):19866-19871.

EL Khoury et al., "Ccr2 deficiency impairs microglial accumulation and accelerates progression of Alzheimer-like disease," Nat Med, 2007, 13(4):432-438.

Elger et al., "Novel alpha-amino-3-hydroxy-5-methyl-4-isoxazole propionate (AMPA) receptor antagonists of 2,3-benzodiazepine type: chemical synthesis, in vitro characterization, and in vivo prevention of acute neurodegeneration," J. Med. Chem., Jul. 2005, 48(14): 4618-4627.

Falasca and Mufficci, "Targeting p110gamma in gastrointestinal cancers: attack on multiple fronts," Frontiers in Physiology, Oct. 15, 2014, 5:1-10.

Garamvolgyi et al., "Design and Synthesis of new imidazo[1,2-a]pyridine and imidazo[1,2-a]pyrazine derivatives with antiproliferative activity against melanoma cells," Eur J Med Chem., Jan. 27, 2018, 108:623-643.

Giri et al., "Mechanism of amyloid peptide induced CCR5 expression in monocytes and its inhibition by siRNA for Egr-1," Am J Physiol Cell Physiol., Aug. 2005, 289:C264-C276.

Gonzalez-Garcia et al., "Phosphatidylinositol 3-kinase gamma inhibition ameliorates inflammation and tumor growth in a model of colitis-associated cancer," Gastroenterology, Apr. 2010, 138(4):1373-1384.

Hannahan and Weinberg, "Hallmarks of cancer: the next generation," Cell, Mar. 4, 2011, 144(5):646-674.

Hayer et al., "PI3Kgamma regulates cartilage damage in chronic inflammatory arthritis," FASB J, 2009, 23(12):4288-4298.

International Preliminary Report on Patentability in International Application No. PCT/US2016/017073, dated Aug. 15, 2017, 11 pages.

International Preliminary Report on Patentability in International Application No. PCT/US2016/060468, dated May 8, 2018, 9 pages.

International Preliminary Report on Patentability in International Application No. PCT/US2017/012135, dated Jul. 19, 2018, 10 pages.

International Preliminary Report on Patentability in International Application No. PCT/US2017/038955, dated Dec. 25, 2018, 8 pages.

International Preliminary Report on Patentability in International Application No. PCT/US2018/056311, dated Apr. 30, 2020, 8 pages.

International Search Report and Written Opinion in International Application No. PCT/US2016/017073, dated Apr. 15, 2016, 21 pages.

International Search Report and Written Opinion in International Application No. PCT/US2016/060468, dated Jan. 25, 2017, 11 pages.

International Search Report and Written Opinion in International Application No. PCT/US2017/012135, dated May 19, 2017, 17 pages.

International Search Report and Written Opinion in International Application No. PCT/US2017/038955, dated Aug. 8, 2017, 15 pages.

International Search Report and Written Opinion in International Application No. PCT/US2018/056311, dated Jan. 21, 2019, 10 pages.

International Search Report and Written Opinion in International Application No. PCT/US2019/49419, dated Jan. 31, 2020, 10 pages.

Invitation to Pay Additional Fees in International Application No. PCT/US19/49419, dated Dec. 5, 2019, 10 pages.

Jimenez et al., "The p85 regulatory subunit controls sequential activation of phosphoinositide 3-kinase by Tyr kinases and Ras," J Biol Chem., Nov. 1, 2002, 277(44):41556-415562.

Kaneda et al., "Abstract 3650: PI3-kinase gamma controls the macrophage M1-M2 switch, thereby promoting tumor immunosuppression and progression," Presented at the Proceedings of the AACR Annual Meeting 2014, San Diego, CA, Apr. 5-9, 2014, Cancer Res., 74(Suppl 19): 2 pages.

Kerekes et al., "Aurora kinase inhibitors based on the imidazo[1,2-a]pyrazine core: fluorine and deuterium incorporation improve oral absorption and exposure," J Med Chem., Jan. 13, 2011, 54(1):201-210.

Kolb et al., "Catalytic Asymmetric Dihydroxylation," Chem Rev., 1994, 94(8):2483-2547.

Kumar et al., "Discovery and optimization of a new class of pyruvate kinase inhibitors as potential therapeutics for the treatment of methicillin-resistant *Staphylococcus aureus* infections," Bioorganic & Medicinal Chemistry, Jan. 2014, 22(5): 1708-1725.

Laffargue et al., "Phosphoinositide 3-kinase gamma is an essential amplifier of mast cell function," Immunity, 2002, 16(3)441-451.

Li et al., "PI3Kγ inhibition alleviates symptoms and increases axon number in experimental autoimmune encephalomyelitis mice," Neuroscience, 2013, 253:89-99.

Liu et al., "Discovery of Novel Small Molecule Mer Kinase Inhibitors for the Treatment of Pediatric Acute Lymphoblastic Leukemia," ACS Med. Chem. Lett., Feb. 9, 2012, 3(2): 129-134.

Lupia et al., "Ablation of phosphoinositide 3-kinase-gamma reduces the severity of acute pancreatitis," Am J Pathology., Dec. 2004, 165(6):2003-2011.

Mamedov et al., "Acid-catalyzed rearrangement of 3-(beta-2-aminostyryl)quinoxalin-2(1H)ones—a new and efficient method for the synthesis of 2-benzimidazol-2-ylquinolines," Tetrahedron Letters, Dec. 2010, 51(50):6503-6506.

Manning et al., "An innovative and efficient synthesis of stable isotope labelled 1-methyl-5-(4,4,5,5-tetramethyl-1,3,2-dioxaborolan-

(56) References Cited

OTHER PUBLICATIONS 2-yl)-1H-pyrazole via [13C42H3] N-methylpyrazole," J Label Compd Radiopharm., Nov. 2012, 55(13)467-469.

Martin et al., "PI3Kγ mediates Kaposi's sarcoma-associated herpes virus vGPCR-induced sarcomagenesis," Cancer Cell, 2011, 19(6):805-813.

Mejdrova et al., "Highly selective Phosphatidylinositol 4-Kinase III[beta] Inhibitors and Structural Insight into Their Mode of Action," Journal of Medicinal Chemistry, May 2015, 58(9): 3767-3793.

Moreno-Dorado et al., "Enantioselective synthesis of arylmethoxyacetic acid derivatives," Tetrahedron: Asymmetry, Feb. 21, 2003, 14(4):503-510.

Kendell et al., "Bromopropionic Acid," Organic Synthesis, 1941, 1:131.

Marvel et al., "Glutaric Acid," Organic Synthesis, 1941, 1:289.

Read, "Hydroxypropionic Acid," Organic Synthesis, 1941, 1:321.

Park et al., "Homogenous proximity tyrosine kinase assays: scintillation proximity assay versus homogenous time-resolved fluorescence," Anal. Biochem., Apr. 1999, 269(1):94-104.

Passos et al., "Involvement of phosphoinositide 3-kinase gamma in the neuro-inflammatory response and cognitive impairments induced by beta-amyloid 1-40 peptide in mice," Brain Behav. Immun., Mar. 2010, 24(3):493-501.

Pinho et al., "Phosphoinositide-3 kinases critically regulate the recruitment and survival of eosinophils in vivo: importance for the resolution of allergic inflammation," J. Leukocyte Biol., May 2005, 77(5):800-810.

Pomel et al., "Furan-2-ylmethylene thiazolidinediones as novel, potent, and selective inhibitors of phosphoinositide 3-kinase gamma," J. Med. Chem., Jun. 2006, 49(13):3857-71.

Prete et al., "Defective dendritic cell migration and activation of adaptive immunity in PI3Kgamma-deficient mice," The EMBO Journal, Sep. 1, 2004, 23(17):3505-3515.

Randis et al., "Role of PI3Kdelta and PI3Kgamma in inflammatory arthritis and tissue localization of neutrophils," Eur J Immunol., May 2008, 38(5):1215-1224.

Remington's Pharmaceutical Sciences, Mack Publishing Company, Easton, 1985, 17th ed., p. 1418.

Rodrigues et al., "Absence of PI3Kgamma leads to increased leukocyte apoptosis and diminished severity of experimental autoimmune encephalomyelitis," J Neuroimmunol, May 2010, 222(1-2):90-94.

Ruckle et al., "PI3Kgamma inhibition: towards an 'aspirin of the 21st century'?" Nat Rev Drug Discov., Nov. 2006, 5(11):903-918.

Ruiz-Castillo et al., "Applications of Palladium-Catalyzed C—N Cross-Coupling Reactions," Chem Rev., Oct. 12, 2016, 116(19): 12564-12649.

Schmid et al., "Receptor tyrosine kinases and TLR/IL1Rs unexpectedly activate myeloid cell PI3kγ, a single convergent point promoting tumor inflammation and progression," Cancer Cell, 2011, 19:715-727.

Schmidt et al., "Abstract 411: PI3 Kinase gamma Control of Arginase-1 expression promotes tumor immunosuppression," Cancer Res., Apr. 15, 2012, 72 (Suppl 1).

Sharpless et al., "The osmium-catalyzed asymmetric dihydroxylation: a new ligand class and a process improvement," J Org. Chem., 1992, 57(10):2768-2771.

Subramaniam et al., "Targeting nonclassical oncogenes for therapy in T-ALL," Cancer Cell, 2012, 21(4):459-472.

Thomas et al., "Airway inflammation: chemokine-induced neutrophilia and the class I phosphoinositide 3-kinases," Eur J Immunol., Apr. 2005, 35(4):1283-1291.

Vaillard et al., "Synthesis of 6-substituted 2-pyrrolyl and Indolyl Benzoxazoles by Intramolecular O—Arylation in Photostimulated Reactions," The Journal of Organic Chemistry, Feb. 2012, 77(3): 1507-1519.

Vanhaesebroeck et al., "Signalling by PI3K isoforms: insights from gene-targeted mice," Trends Biochem Sci, Apr. 2005, 30(4):194-204.

Vecchione et al., "Protection from angiotensin II-mediated vasculotoxic and hypertensive response in mice lacking PI3Kgamma," J Exp Med., 2005, 201:1217-1228.

Venable et al., "Phosphoinositide 3-Kinase Gamma (PI3K[gamma]) Inhibitors for the Treatment of Inflammation and Autoimmune Disease," Recent Patents on Inflammation & Allergy Drug Discovery, Jan. 2010, 4(1): 1-15.

Winterfeldt, "Applications of Diisobutylaluminium Hydride (DIBAH) and Triisobutylaluminium (TIBA) as Reducing Agents in Organic Synthesis," Synthesis 1975, 10:617-630.

Xu et al., "Design, synthesis and biological evaluation of deuterated nintedanib for improving pharmacokinetic properties," J Label Compd Radiopharma., Jun. 15, 2015, 58(7):308-312.

Chilean Office Action in Chilean Application No. 1047-2020, dated Apr. 9, 2021, 19 pages.

International Preliminary Report on Patentability in International Application No. PCT/US2019/049419, dated Mar. 18, 2021, 7 pages.

XRPD Form IA

DSC Form 1A

TGA Form IA

XRPD Form IIA

DSC Form IIA

TGA Form IIA

XRPD Form IIIA

DSC Form IIIA

XRPD Form IB

DSC Form IB

XRPD Form IIB

DSC Form IC

CRYSTALLINE FORMS OF A PHOSPHOINOSITIDE 3-KINASE (PI3K) INHIBITOR

TECHNICAL FIELD

The present invention relates to salts and crystalline forms of 2-(3-(8-amino-6-(trifluoromethyl)imidazo[1,2-a]pyrazin-3-yl)-4-methylphenyl)-3,3,3-trifluoro-2-hydroxypropanamide, 8-amino-N-(2-hydroxy-2-methylpropyl)-3-(2-methyl-5-(1,1,1-trifluoro-2-hydroxypropan-2-yl)phenyl)imidazo[1,2-a]pyrazine-6-carboxamide and 8-amino-N-(2-hydroxy-2-methylpropyl)-3-(2-(methyl-d$_3$)-5-(1,1,1-trifluoro-2-hydroxypropan-2-yl)phenyl)imidazo[1,2-a]pyrazine-6-carboxamide which are PI3K inhibitors useful in the treatment of cancer and other diseases.

BACKGROUND OF THE INVENTION

The compounds 2-(3-(8-amino-6-(trifluoromethyl)imidazo[1,2-a]pyrazin-3-yl)-4-methylphenyl)-3,3,3-trifluoro-2-hydroxypropanamide having Formula A, 8-amino-N-(2-hydroxy-2-methylpropyl)-3-(2-methyl-5-(1,1,1-trifluoro-2-hydroxypropan-2-yl)phenyl)imidazo[1,2-a]pyrazine-6-carboxamide having Formula B and 8-amino-N-(2-hydroxy-2-methylpropyl)-3-(2-(methyl-d$_3$)-5-(1,1,1-trifluoro-2-hydroxypropan-2-yl)phenyl)imidazo[1,2-a]pyrazine-6-carboxamide having Formula C:

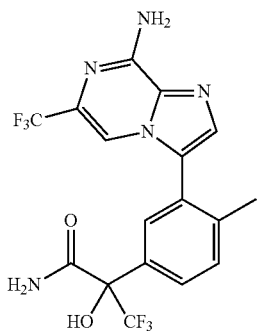

(A)

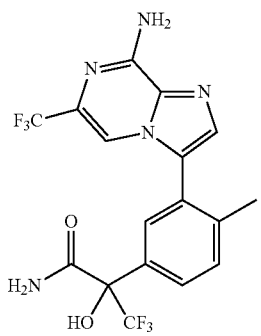

(B)

-continued

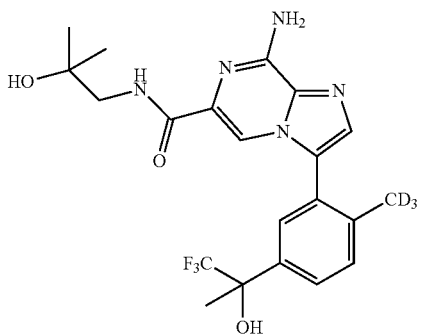

(C)

are phosphoinositide 3-kinase (PI3K) inhibitors useful in the treatment of various diseases including cancer. For the development of a drug, it is typically advantageous to employ a form of the drug having desirable properties with respect to its preparation, purification, reproducibility, stability, bioavailability, and other characteristics. Accordingly, the salts and crystalline forms of the compounds of Formula A, Formula B and Formula C provided herein address the ongoing need for the development of PI3K inhibitors for the treatment of serious diseases.

SUMMARY OF THE INVENTION

The present invention provides salts and crystalline forms of the compound of Formula A, crystalline forms of the compound of Formula B and a crystalline form of the compound of Formula C:

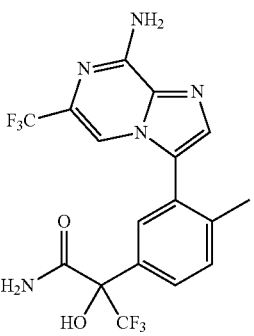

(A)

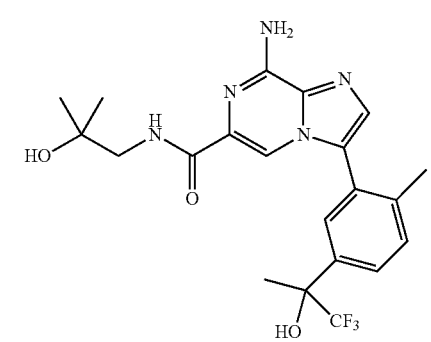

(B)

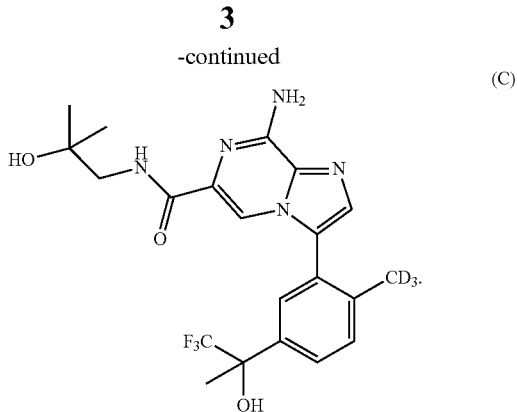

(C)

The present invention further provides a composition comprising the salts and crystalline forms of the compound of Formula A provided herein and at least one pharmaceutically acceptable carrier. The present invention further provides a composition comprising a crystalline form of the compound of Formula B and at least one pharmaceutically acceptable carrier. The present invention further provides a composition comprising a crystalline form of the compound of Formula C and at least one pharmaceutically acceptable carrier.

The present invention further provides a process for preparing salts and crystalline forms of the invention.

The present invention further provides a method of treating a disease associated with abnormal expression or activity of a PI3K kinase in a patient, comprising administering to the patient a therapeutically effective amount of a salt or crystalline form of the invention.

DETAILED DESCRIPTION

Figure 1:
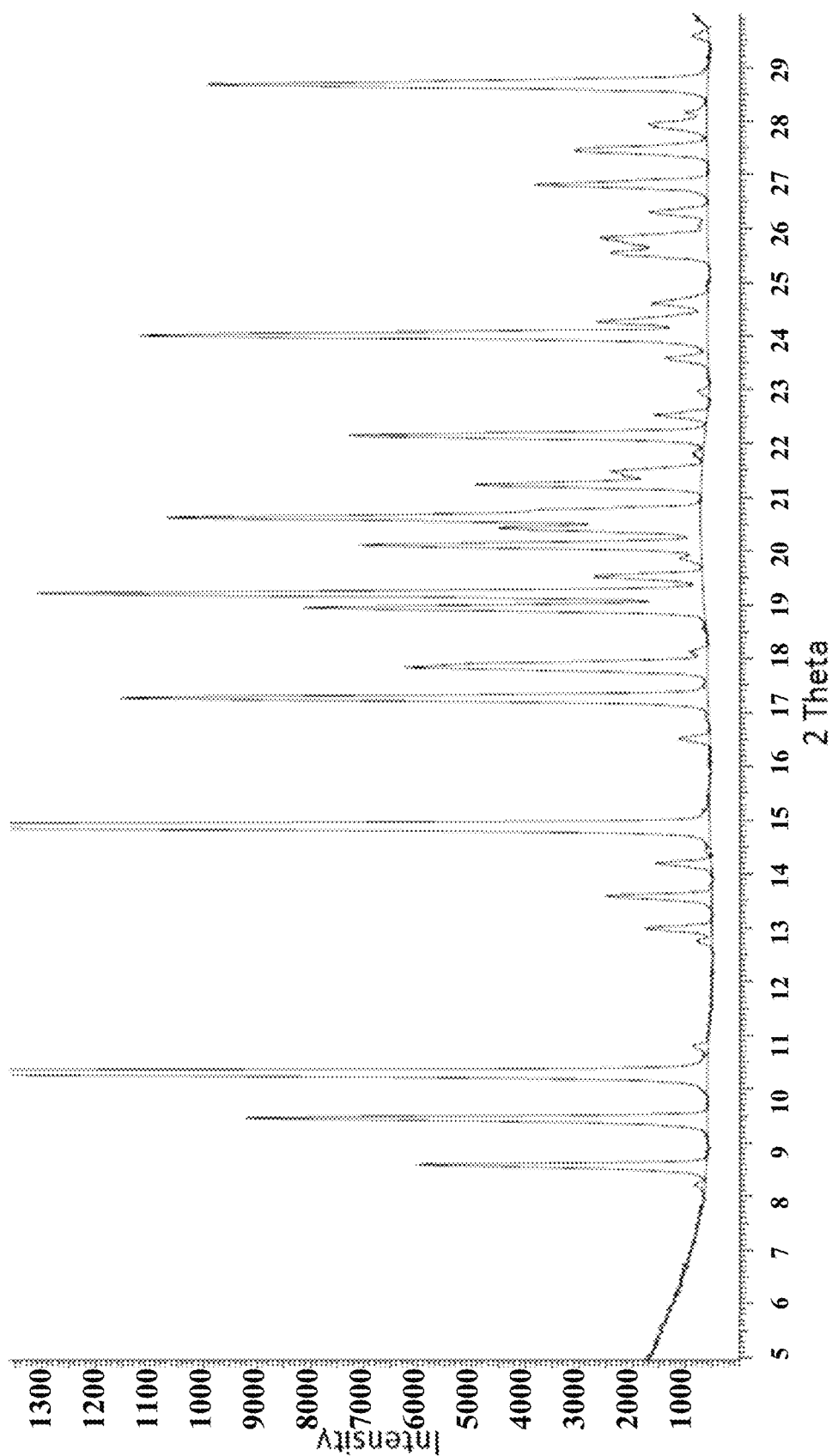
FIG. 1 shows an XRPD pattern for 2-(3-(8-amino-6-(trifluoromethyl)imidazo[1,2-a]pyrazin-3-yl)-4-methylphenyl)-3,3,3-trifluoro-2-hydroxypropanamide, crystalline Form IA.

The present invention relates to, inter alia, salts and crystalline forms of the PI3K inhibitor 2-(3-(8-amino-6-(trifluoromethyl)imidazo[1,2-a]pyrazin-3-yl)-4-methylphenyl)-3,3,3-trifluoro-2-hydroxypropanamide having Formula A:

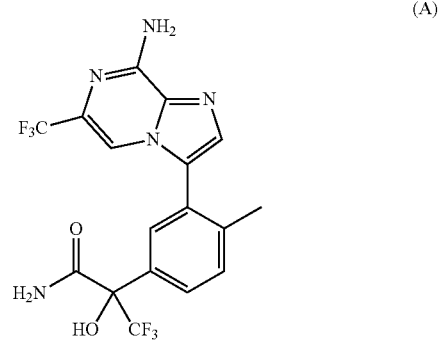 [SMILES: Cc1ccc(C(O)(C(N)=O)C(F)(F)F)cc1-c1cnc2c(N)nc(C(F)(F)F)cn12]

(A)

which are useful, for example, in the preparation of solid dosage forms of the above compound for the treatment of various diseases, including cancer.

The present invention also relates to, inter alia, crystalline forms of the PI3K inhibitor 8-amino-N-(2-hydroxy-2-methylpropyl)-3-(2-methyl-5-(1,1,1-trifluoro-2-hydroxypropan-2-yl)phenyl)imidazo[1,2-a]pyrazine-6-carboxamide having Formula B:

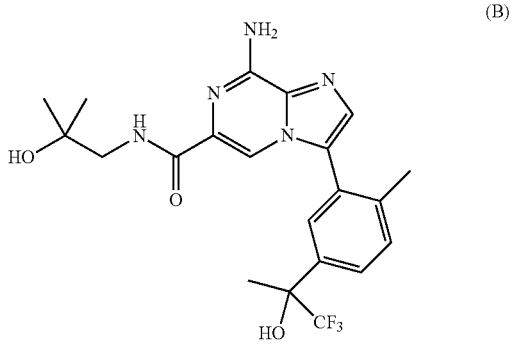 [SMILES: Cc1ccc(C(C)(O)C(F)(F)F)cc1-c1cnc2c(N)nc(C(=O)NCC(C)(C)O)cn12]

(B)

The present invention also relates to, inter alia, crystalline forms of the PI3K inhibitor 8-amino-N-(2-hydroxy-2-methylpropyl)-3-(2-(methyl-d$_3$)-5-(1,1,1-trifluoro-2-hydroxypropan-2-yl)phenyl)imidazo[1,2-a]pyrazine-6-carboxamide having Formula C:

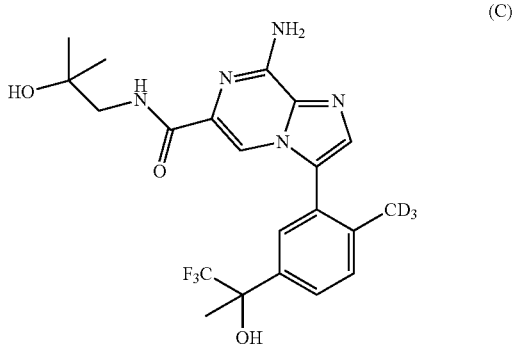 [SMILES: [2H]C([2H])([2H])c1ccc(C(C)(O)C(F)(F)F)cc1-c1cnc2c(N)nc(C(=O)NCC(C)(C)O)cn12]

(C)

Typically, different crystalline forms of the same substance have different bulk properties relating to, for example, hygroscopicity, solubility, stability, and the like. Forms with high melting points often have good thermodynamic stability which is advantageous in prolonging shelf-life drug formulations containing the solid form. Forms with lower melting points often are less thermodynamically stable, but are advantageous in that they have increased water solubility, translating to increased drug bioavailability. Forms that are weakly hygroscopic are desirable for their stability to heat and humidity and are resistant to degradation during long storage. Anhydrous forms are often desirable because they can be consistently made without concern for variation in weight or composition due to varying solvent or water content. On the other hand, hydrated or solvated forms can be advantageous in that they are less likely to be hygroscopic and may show improved stability to humidity under storage conditions.

As used herein, "crystalline form" is meant to refer to a certain lattice configuration of a crystalline substance. Different crystalline forms of the same substance typically have different crystalline lattices (e.g., unit cells) which are attributed to different physical properties that are characteristic of each of the crystalline forms. In some instances, different lattice configurations have different water or solvent content. The different crystalline lattices can be identified by solid state characterization methods such as by X-ray powder diffraction (XRPD). Other characterization methods such as differential scanning calorimetry (DSC), thermogravimetric analysis (TGA), dynamic vapor sorption (DVS), solid state NMR, and the like further help identify the crystalline form as well as help determine stability and solvent/water content.

Crystalline forms of a substance include both solvated (e.g., hydrated) and non-solvated (e.g., anhydrous) forms. A hydrated form is a crystalline form that includes water in the crystalline lattice. Hydrated forms can be stoichiometric hydrates, where the water is present in the lattice in a certain water/molecule ratio such as for hemihydrates, monohydrates, dihydrates, etc. Hydrated forms can also be non-stoichiometric, where the water content is variable and dependent on external conditions such as humidity.

Crystalline forms are most commonly characterized by XRPD. An XRPD pattern of reflections (peaks) is typically considered a fingerprint of a particular crystalline form. It is well known that the relative intensities of the XRPD peaks can widely vary depending on, inter alia, the sample preparation technique, crystal size distribution, filters, the sample mounting procedure, and the particular instrument employed. In some instances, new peaks may be observed or existing peaks may disappear, depending on the type of instrument or the settings (for example, whether a Ni filter is used or not). As used herein, the term "peak" refers to a reflection having a relative height/intensity of at least about 4% of the maximum peak height/intensity. Moreover, instrument variation and other factors can affect the 2-theta values. Thus, peak assignments, such as those reported herein, can vary by plus or minus about 0.2° (2-theta), and the term "substantially" as used in the context of XRPD herein is meant to encompass the above-mentioned variations.

In the same way, temperature readings in connection with DSC, TGA, or other thermal experiments can vary about ±4° C. depending on the instrument, particular settings, sample preparation, etc. For example, with DSC it is known that the temperatures observed will depend on the rate of the temperature change as well as the sample preparation technique and the particular instrument employed. Thus, the values reported herein related to DSC thermograms can vary, as indicated above, by ±4° C. Accordingly, a crystalline form reported herein having a DSC thermogram "substantially" as shown in any of the Figures is understood to accommodate such variation.

Crystalline Forms of the Compound of Formula A

The compound of Formula A can be isolated in numerous crystalline forms, including, for example, crystalline forms which are anhydrous, and/or non-solvated or solvated. In some embodiments, the crystalline forms of the compound of Formula A are solvated. In some embodiments, the crystalline forms of the compound of Formula A are anhydrous. In some embodiments, the crystalline forms of the compound of Formula A are non-solvated. In some embodiments, the crystalline forms of the compound of Formula A are anhydrous and non-solvated. By "anhydrous" is meant that the crystalline form of the compound of Formula A contains essentially no bound water in the crystal lattice structure, i.e., the compound does not form a crystalline hydrate.

In some embodiments, the present application provides a process of preparing a crystalline form of the compound 2-(3-(8-amino-6-(trifluoromethyl)imidazo[1,2-a]pyrazin-3-yl)-4-methylphenyl)-3,3,3-trifluoro-2-hydroxypropanamide. In some embodiments, the process comprises dissolving 2-(3-(8-amino-6-(trifluoromethyl)imidazo[1,2-a]pyrazin-3-yl)-4-methylphenyl)-3,3,3-trifluoro-2-hydroxypropanamide in a solvent to form a mixture and crystallizing the compound from the mixture.

In some embodiments, the solvent comprises isopropyl acetate. In some embodiments, the solvent further comprises heptane.

In some embodiments, the solvent comprises methanol.

In some embodiments, the process further comprises heating the mixture to a temperature of from about 70° C. to about 90° C.

In some embodiments, the process further comprises heating the mixture to a temperature of from about 50° C. to about 70° C.

In some embodiments, the process further comprises cooling the mixture to room temperature.

The present application further provides a crystalline form of the compound 2-(3-(8-amino-6-(trifluoromethyl)imidazo[1,2-a]pyrazin-3-yl)-4-methylphenyl)-3,3,3-trifluoro-2-hydroxypropanamide, which is prepared according to a process provided herein. In some embodiments, the crystalline form is Form IA as described herein. In some embodiments, the crystalline form is Form IIA as described herein. In some embodiments, the crystalline form is Form IIIA as described herein.

In some embodiments, the present application provides a process of preparing a hydrobromic acid salt of the compound 2-(3-(8-amino-6-(trifluoromethyl)imidazo[1,2-a]pyrazin-3-yl)-4-methylphenyl)-3,3,3-trifluoro-2-hydroxypropanamide. In some embodiments, the process comprises dissolving the compound of Formula A in a solvent to form a mixture and adding hydrobromic acid to the mixture.

In some embodiments of the process of preparing the hydrobromic acid salt, the solvent comprises methanol.

In some embodiments of the process of preparing the hydrobromic acid salt, the hydrobromic acid is added to the mixture as an aqueous solution of hydrobromic acid.

In some embodiments of the process of preparing the hydrobromic acid salt, an excess amount of hydrobromic acid is added to the mixture based on 1 equivalent of 2-(3-(8-amino-6-(trifluoromethyl)imidazo[1,2-a]pyrazin-3-yl)-4-methylphenyl)-3,3,3-trifluoro-2-hydroxypropanamide.

In some embodiments of the process of preparing the hydrobromic acid salt, about 1.1 to about 1.5 equivalents of hydrobromic acid are added to the mixture based on 1 equivalent of the 2-(3-(8-amino-6-(trifluoromethyl)imidazo[1,2-a]pyrazin-3-yl)-4-methylphenyl)-3,3,3-trifluoro-2-hydroxypropanamide.

In some embodiments of the process of preparing the hydrobromic acid salt, the process further comprises substantially isolating the 2-(3-(8-amino-6-(trifluoromethyl)imidazo[1,2-a]pyrazin-3-yl)-4-methylphenyl)-3,3,3-trifluoro-2-hydroxypropanamide hydrobromic acid salt.

In some embodiments of the process of preparing the hydrobromic acid salt, the 2-(3-(8-amino-6-(trifluoromethyl)imidazo[1,2-a]pyrazin-3-yl)-4-methylphenyl)-3,3,3-trifluoro-2-hydroxypropanamide hydrobromic acid salt is isolated as a crystalline form.

In some embodiments of the process of preparing the hydrobromic acid salt, the 2-(3-(8-amino-6-(trifluoromethyl)imidazo[1,2-a]pyrazin-3-yl)-4-methylphenyl)-3,3,3-trifluoro-2-hydroxypropanamide hydrobromic acid salt is isolated as a methanol solvate crystalline form.

In some embodiments, the present application further provides a hydrobromic acid salt of 2-(3-(8-amino-6-(trifluoromethyl)imidazo[1,2-a]pyrazin-3-yl)-4-methylphenyl)-3,3,3-trifluoro-2-hydroxypropanamide, which is prepared according to a process provided herein. In some embodiments, the hydrobromic acid salt is crystalline. In some embodiments, the hydrobromic acid salt is a solvated crystalline form. In some embodiments, the hydrobromic acid salt is a methanol solvate crystalline form.

In some embodiments, the crystalline forms of the invention are substantially isolated. By "substantially isolated" is meant that a particular crystalline form of the compound of Formula A is at least partially isolated from impurities. For example, in some embodiments a crystalline form of the invention comprises less than about 50%, less than about 40%, less than about 30%, less than about 20%, less than about 15%, less than about 10%, less than about 5%, less than about 2.5%, less than about 1%, or less than about 0.5% of impurities. Impurities generally include anything that is not the substantially isolated crystalline form including, for example, other crystalline forms and other substances.

In some embodiments, a crystalline form of the compound of Formula A is substantially free of other crystalline forms. The phrase "substantially free of other crystalline forms" means that a particular crystalline form of the compound of Formula A comprises greater than about 80%, greater than about 90%, greater than about 95%, greater than about 98%, greater than about 99% or greater than about 99.5% by weight of the particular crystalline form.

Crystalline Form IA of the Compound of Formula A

In some embodiments, the crystalline form of the compound of Formula A is Form IA. In some embodiments, crystalline Form IA of the compound of Formula A is anhydrous and non-solvated. The preparation of the compound of Form IA of the compound of Formula A is described in Example 1. Crystalline Form IA of the compound of Formula A can be generally prepared as described in Example 2.

Crystalline Form IA of the compound of Formula A can be identified by unique signatures with respect to, for example, X-ray powder diffraction (XRPD), differential scanning calorimetry (DSC), and thermogravimetric analysis (TGA). In some embodiments, crystalline Form IA of the compound of Formula A is characterized by an XRPD pattern substantially as shown in FIG. 1. Peaks from the XRPD pattern are listed in Table 1.

In some embodiments, crystalline Form IA of the compound of Formula A is characterized by an XRPD pattern comprising a peak, in terms of 2θ, at 8.6°±0.2°. In some embodiments, crystalline Form IA of the compound of Formula A is characterized by an XRPD pattern comprising a peak, in terms of 2θ, at 9.5°±0.2°. In some embodiments, crystalline Form IA of the compound of Formula A is characterized by an XRPD pattern comprising a peak, in terms of 2θ, at 10.3°±0.2°. In some embodiments, crystalline Form IA of the compound of Formula A is characterized by an XRPD pattern comprising a peak, in terms of 2θ, at 14.9°±0.2°.

In some embodiments, crystalline Form IA of the compound of Formula A has an XRPD pattern comprising the following peaks, in terms of 2θ: 8.6°±0.2°; 9.5°±0.2°; 10.3°±0.2°; 13.0°±0.2°; 13.6°±0.2°; 14.2°±0.2°; and 14.9°±0.2°. In some embodiments, crystalline Form IA of the compound of Formula A has an XRPD pattern comprising the following peaks, in terms of 2θ: 8.6°±0.2°; 9.5°±0.2°; 10.3°±0.2°; 14.9°±0.2°; 17.3°±0.2°; 17.8°±0.2°; 19.0°±0.2°; 19.2°±0.2°; 20.1°±0.2°; 20.6°±0.2°; 21.2°±0.2°; 22.2°±0.2°; 24.0°±0.2°; 26.8°±0.2°; and 28.7°±0.2°. In some embodiments, crystalline Form IA of the compound of Formula A has an XRPD pattern comprising the following peaks, in terms of 2θ: 10.3°±0.2°; 14.9°±0.2°; 17.3°±0.2°; 19.2°±0.2°; and 24.0°±0.2°.

In some embodiments, crystalline Form IA of the compound of Formula A has an XRPD pattern comprising 2 or more, 3 or more, or 4 or more of the following peaks, in terms of 2θ: 8.6°±0.2°; 9.5°±0.2°; 10.3°±0.2°; 13.0°±0.2°; 13.6°±0.2°; 14.2°±0.2°; 14.9°±0.2°; 17.3°±0.2°; 19.2°±0.2°; 20.6°±0.2°; 24.0°±0.2°; and 28.7°±0.2°. In some embodiments, crystalline Form IA of the compound of Formula A has an XRPD pattern comprising 2 or more, 3 or more, or 4 or more of the following peaks, in terms of 2θ: 8.6°±0.2°; 9.5°±0.2°; 10.3°±0.2°; 14.9°±0.2°; 17.3°±0.2°; 17.8°±0.2°; 19.0°±0.2°; 19.2°0.2°; 20.1°±0.2°; 20.6°±0.2°; 21.2°±0.2°; 22.2°±0.2°; 24.0°±0.2°; 26.8°±0.2°; and 28.7°±0.2°. In some embodiments, crystalline Form IA of the compound of Formula A has an XRPD pattern comprising 2 or more, 3 or more, or 4 or more of the following peaks, in terms of 2θ: 9.5°±0.2°; 10.3°±0.2°; 14.9°±0.2°; 17.3°±0.2°; 19.2°±0.2°; 20.6°±0.2°; 24.0°±0.2°; and 28.7°±0.2°.

Figure 2:
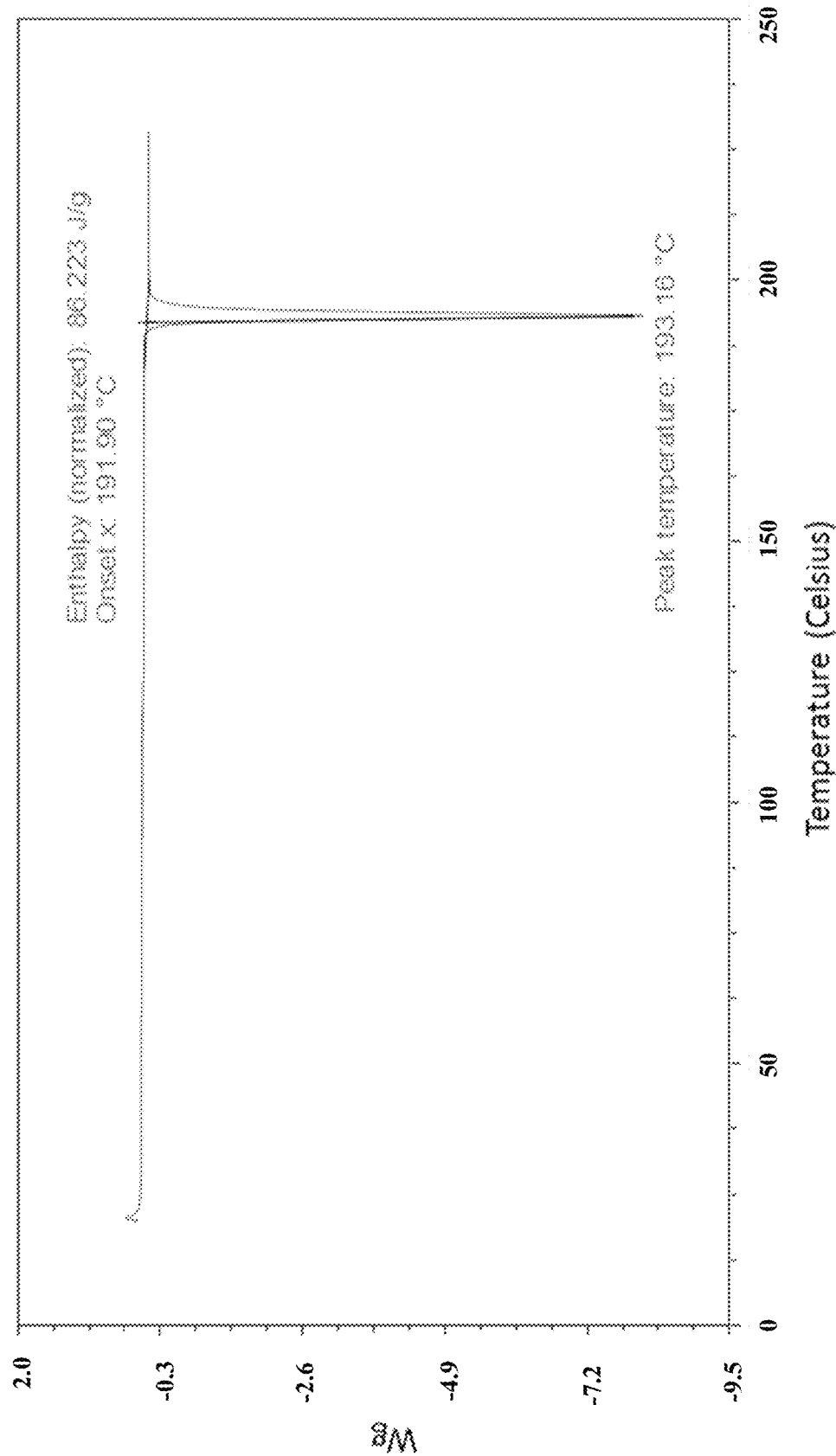
FIG. 2 shows the results of a DSC experiment for 2-(3-(8-amino-6-(trifluoromethyl)imidazo[1,2-a]pyrazin-3-yl)-4-methylphenyl)-3,3,3-trifluoro-2-hydroxypropanamide, crystalline Form IA.

In some embodiments, Form IA of the compound of Formula A is characterized by a DSC thermogram comprising an endothermic peak having a maximum at about 193° C. In some embodiments, crystalline Form IA of the compound of Formula A has a DSC thermogram substantially as shown in FIG. 2.

Figure 3:
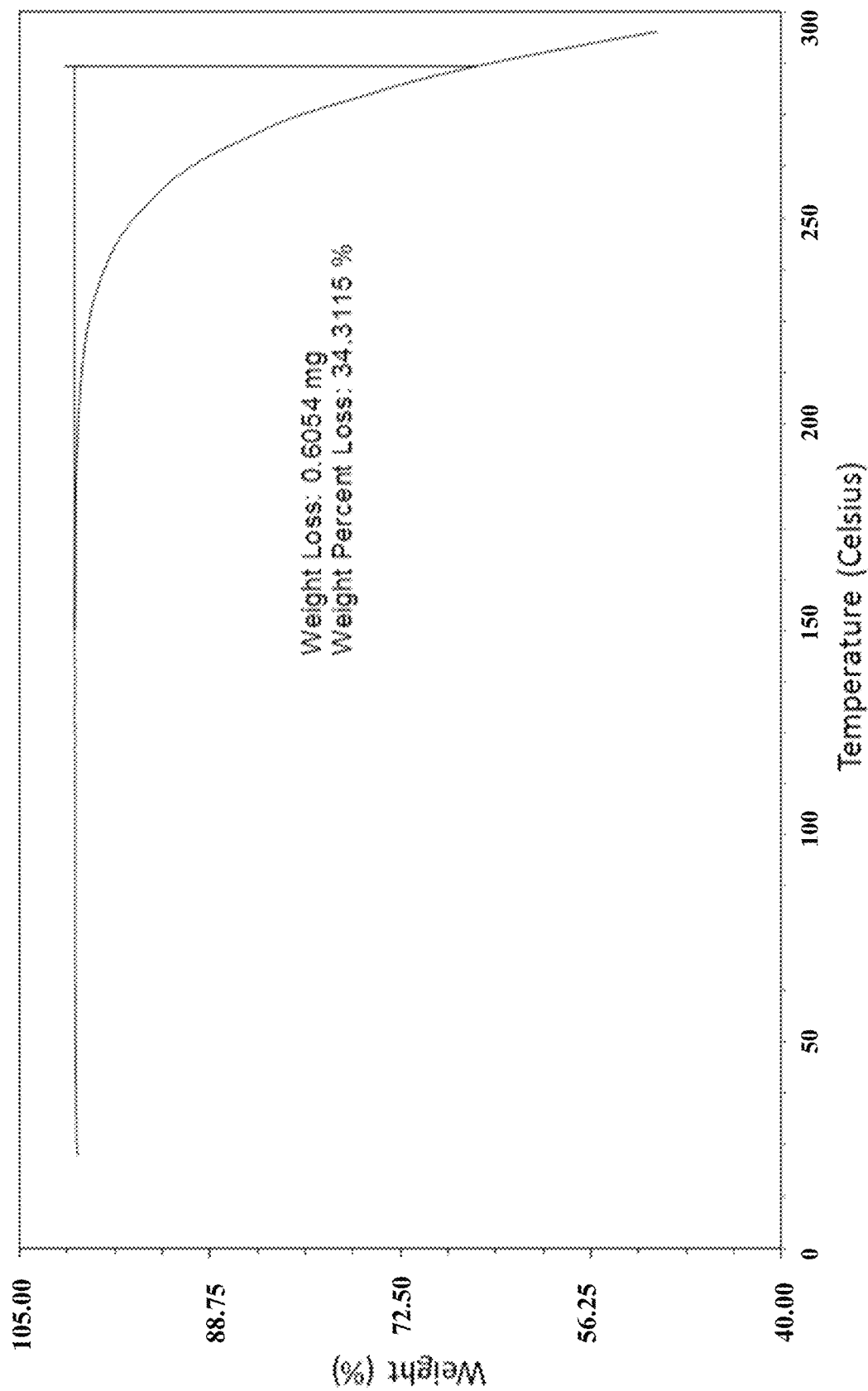
FIG. 3 shows the results of a TGA experiment for 2-(3-(8-amino-6-(trifluoromethyl)imidazo[1,2-a]pyrazin-3-yl)-4-methylphenyl)-3,3,3-trifluoro-2-hydroxypropanamide, crystalline Form IA.

In some embodiments, crystalline Form IA of the compound of Formula A has a TGA trace substantially as shown in FIG. 3.

Crystalline Form IIA of the Compound of Formula A

In some embodiments, the crystalline form of the compound of Formula A is Form IIA. In some embodiments, crystalline Form IIA of the compound of Formula A is anhydrous and non-solvated. This crystalline form can be generally prepared as described in Example 3.

Figure 4:
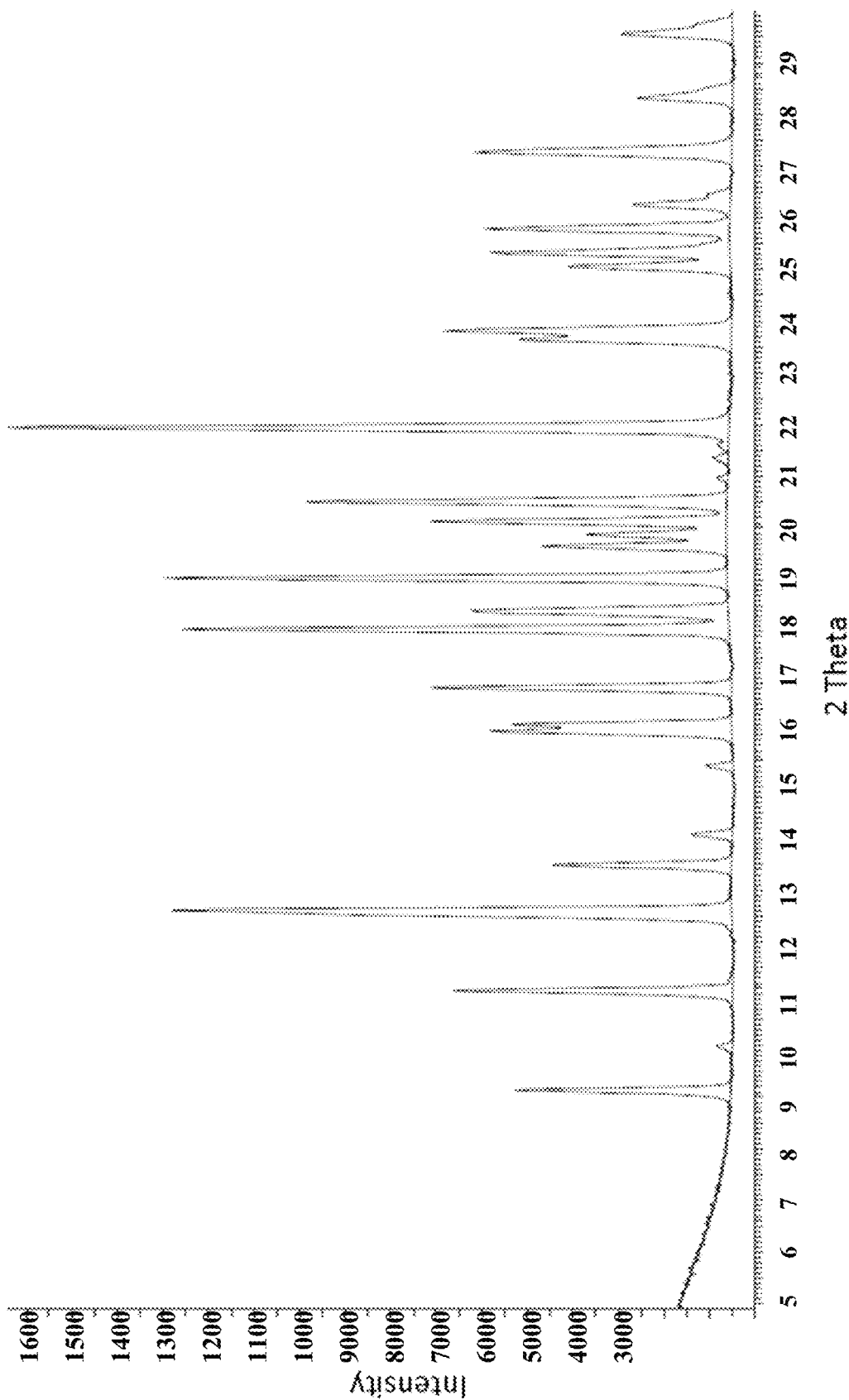
FIG. 4 shows an XRPD pattern for 2-(3-(8-amino-6-(trifluoromethyl)imidazo[1,2-a]pyrazin-3-yl)-4-methylphenyl)-3,3,3-trifluoro-2-hydroxypropanamide, crystalline Form IIA.

Crystalline Form IIA of the compound of Formula A can be identified by unique signatures with respect to, for example, X-ray powder diffraction (XRPD), differential scanning calorimetry (DSC), and thermogravimetric analysis (TGA). In some embodiments, crystalline Form IIA of the compound of Formula A is characterized by an XRPD pattern substantially as shown in FIG. 4. Peaks from the XRPD pattern are listed in Table 2.

In some embodiments, crystalline Form IIA of the compound of Formula A is characterized by an XRPD pattern comprising a peak, in terms of 2θ, at 9.1±0.2°. In some embodiments, crystalline Form IIA of the compound of Formula A is characterized by an XRPD pattern comprising a peak, in terms of 2θ, at 11.1°±0.2°. In some embodiments, crystalline Form IIA of the compound of Formula A is characterized by an XRPD pattern comprising a peak, in terms of 2θ, at 21.9°±0.2°. In some embodiments, crystalline Form IIA of the compound of Formula A is characterized by an XRPD pattern comprising a peak, in terms of 2θ, at 12.6°±0.2°. In some embodiments, crystalline Form IIA of the compound of Formula A is characterized by an XRPD pattern comprising a peak, in terms of 2θ, at 13.6°±0.2°. In some embodiments, crystalline Form IIA of the compound of Formula A is characterized by an XRPD pattern comprising a peak, in terms of 2θ, at 18.0°±0.2°. In some embodiments, crystalline Form IIA of the compound of Formula A is characterized by an XRPD pattern comprising a peak, in terms of 2θ, at 19.0°±0.2°.

In some embodiments, crystalline Form IIA of the compound of Formula A has an XRPD pattern comprising the following peaks, in terms of 2θ: 9.1°±0.2°; 11.1°±0.2°; 12.6°±0.2°; and 13.5°±0.2°. In some embodiments, crystalline Form IIA of the compound of Formula A has an XRPD pattern comprising the following peaks, in terms of 2θ: 9.1°±0.2°; 11.1°±0.2°; 12.6°±0.2°; 13.5°±0.2°; 16.1°±0.2°; 16.9°±0.2°; 18.0°±0.2°; 18.4°±0.2°; 19.0°±0.2°; 19.7°±0.2°; 20.1°±0.2°; 20.5°±0.2°; 21.9°±0.2°; 23.7°±0.2°; 23.8°±0.2°; 25.1°±0.2°; 25.3°±0.2°; 25.8°±0.2°; and 27.3°±0.2°. In some embodiments, crystalline Form IIA of the compound of Formula A has an XRPD pattern comprising the following peaks, in terms of 2θ: 12.6°±0.2°; 18.0°±0.2°; 19.0°±0.2°; and 21.9°±0.2°.

In some embodiments, crystalline Form IIA of the compound of Formula A has an XRPD pattern comprising 2 or more, 3 or more, or 4 or more of the following peaks, in terms of 2θ: 9.1°±0.2°; 11.1°±0.2°; 12.6°±0.2°; 13.5°±0.2°; 18.0°±0.2°; 19.0°±0.2°; 20.5°±0.2°; and 21.9°±0.2°. In some embodiments, crystalline Form IIA of the compound of Formula A has an XRPD pattern comprising 2 or more, 3 or more, or 4 or more of the following peaks, in terms of 2θ: 9.1°±0.2°; 11.1°±0.2°; 12.6°±0.2°; 13.5°±0.2°; 16.1°±0.2°; 16.9°±0.2°; 18.0°±0.2°; 18.4°±0.2°; 19.0°±0.2°; 19.7°±0.2°; 20.1°±0.2°; 20.5°±0.2°; 21.9°±0.2°; 23.7°±0.2°; 23.8°±0.2°; 25.1°±0.2°; 25.3°±0.2°; 25.8°±0.2°; and 27.3°±0.2°. In some embodiments, crystalline Form IIA of the compound of Formula A has an XRPD pattern comprising 2 or more, 3 or more, or 4 or more of the following peaks, in terms of 2θ: 12.6°±0.2°; 18.0°±0.2°; 19.0°±0.2°; 20.5°±0.2°; and 21.9°±0.2°.

Figure 5:
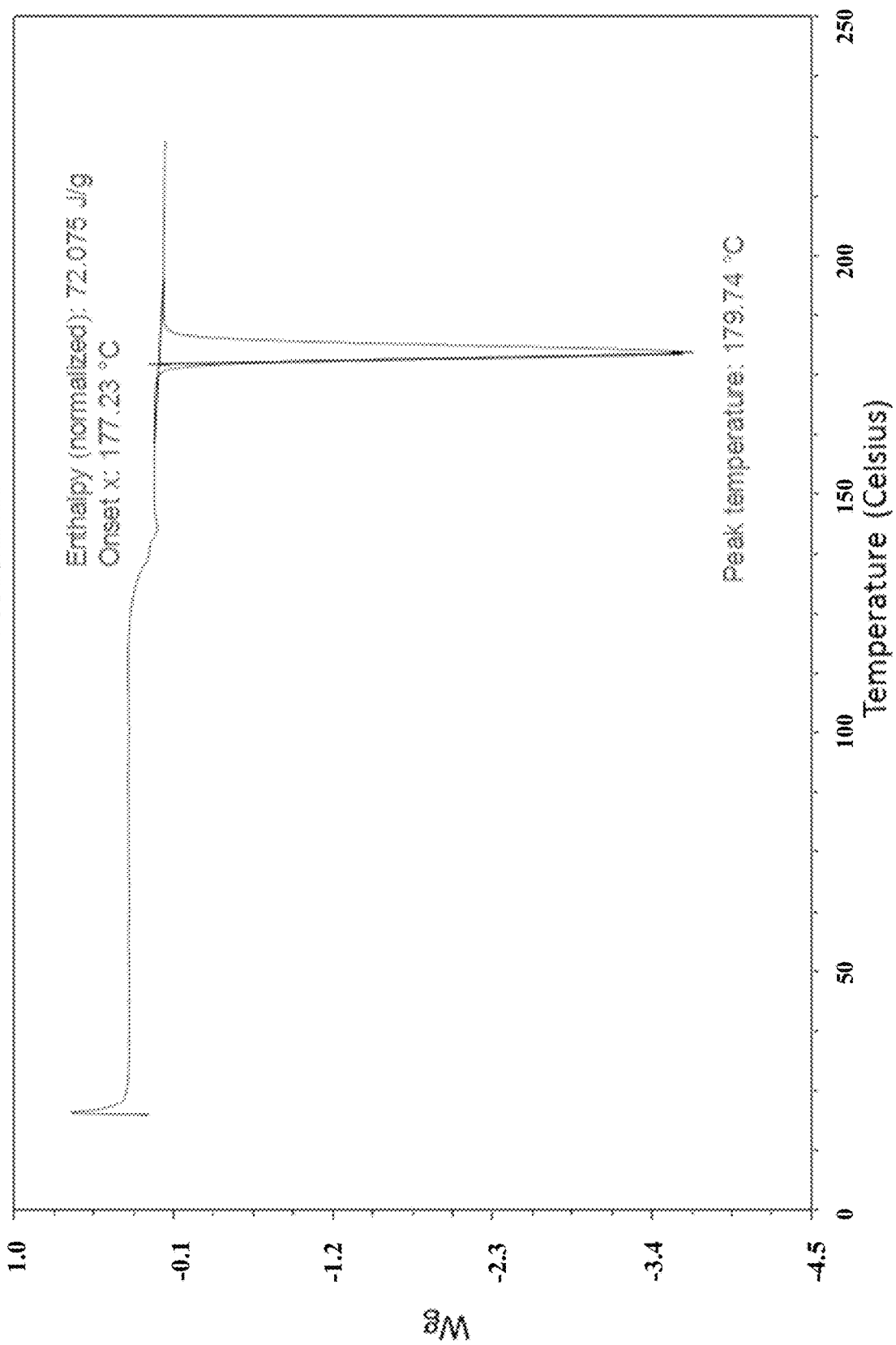
FIG. 5 shows the results of a DSC experiment for 2-(3-(8-amino-6-(trifluoromethyl)imidazo[1,2-a]pyrazin-3-yl)-4-methylphenyl)-3,3,3-trifluoro-2-hydroxypropanamide, crystalline Form IIA.

In some embodiments, Form IIA of the compound of Formula A is characterized by a DSC thermogram comprising an endothermic peak having a maximum at about 180° C. In some embodiments, crystalline Form IIA of the compound of Formula A has a DSC thermogram substantially as shown in FIG. 5.

Figure 6:
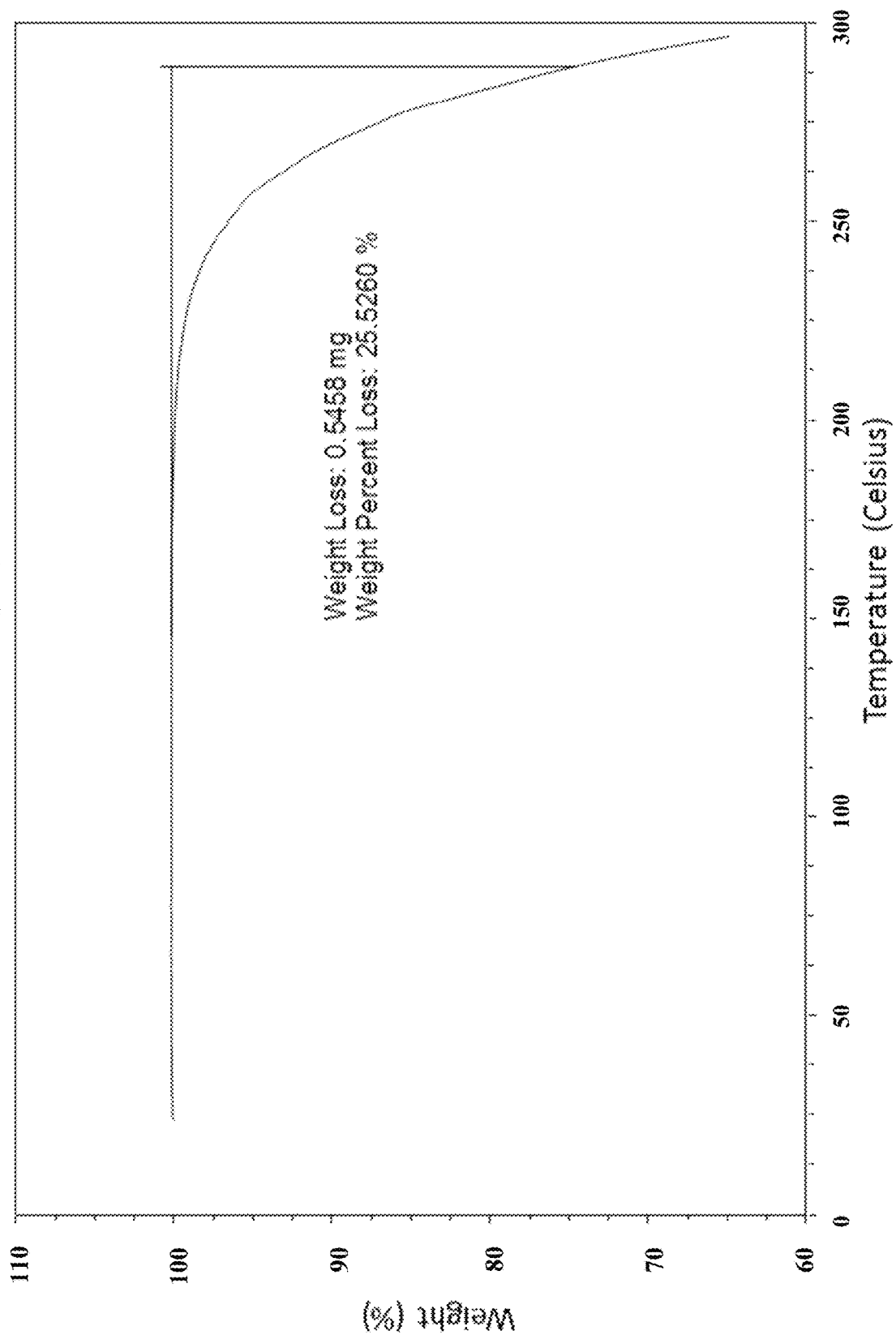
FIG. 6 shows the results of a TGA experiment for 2-(3-(8-amino-6-(trifluoromethyl)imidazo[1,2-a]pyrazin-3-yl)-4-methylphenyl)-3,3,3-trifluoro-2-hydroxypropanamide, crystalline Form IIA.

In some embodiments, crystalline Form IIA of the compound of Formula A has a TGA trace substantially as shown in FIG. 6.

Crystalline Form IIIA of the Compound of Formula A

In some embodiments, the crystalline form of the compound of Formula A is Form IIIA. In some embodiments, crystalline Form IIIA of the compound of Formula A is anhydrous and non-solvated. This crystalline form can be generally prepared as described in Example 4.

Figure 7:
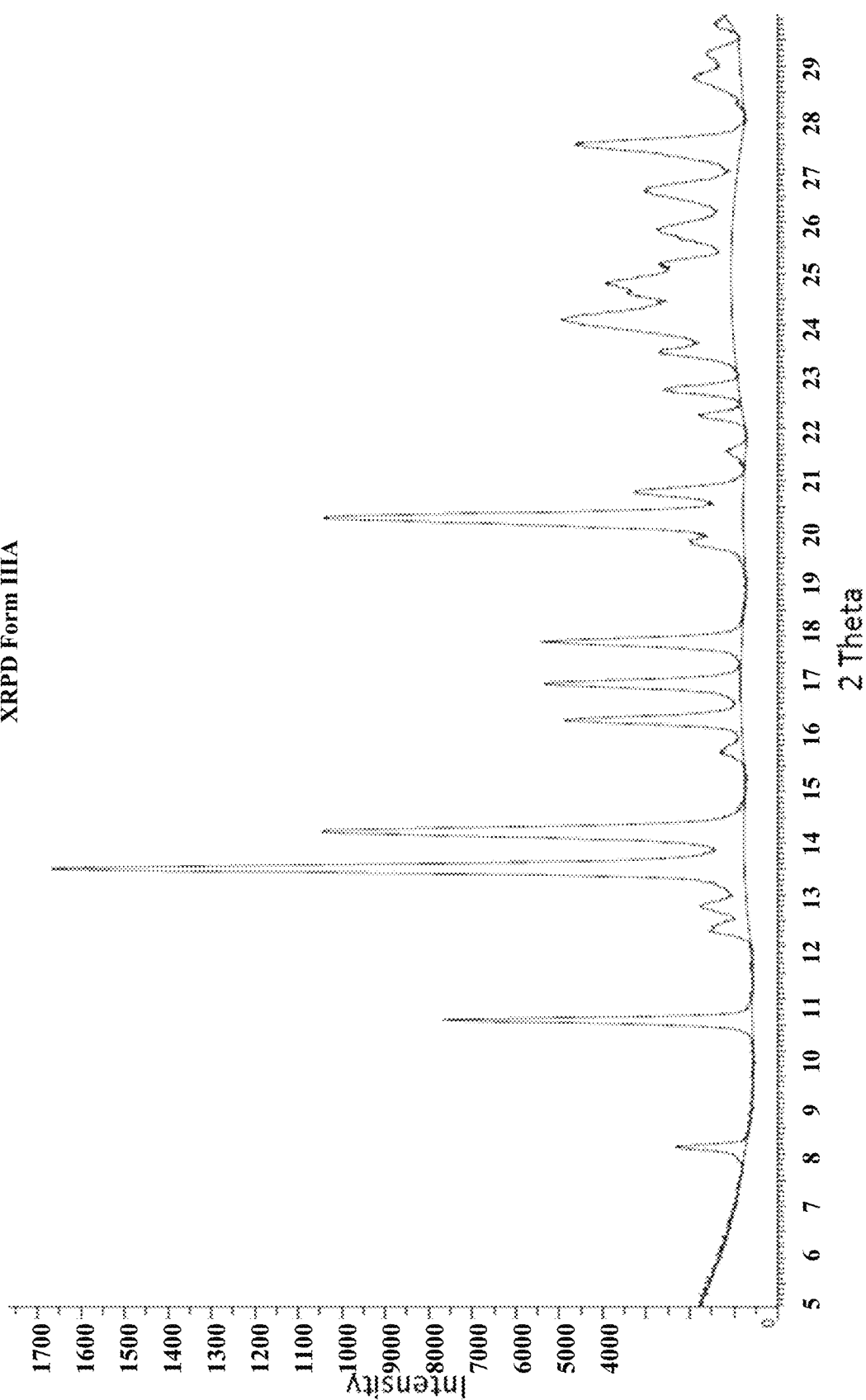
FIG. 7 shows an XRPD pattern for 2-(3-(8-amino-6-(trifluoromethyl)imidazo[1,2-a]pyrazin-3-yl)-4-methylphenyl)-3,3,3-trifluoro-2-hydroxypropanamide, crystalline Form IIIA.

Crystalline Form IIIA of the compound of Formula A can be identified by unique signatures with respect to, for example, X-ray powder diffraction (XRPD), differential scanning calorimetry (DSC), and thermogravimetric analysis (TGA). In some embodiments, crystalline Form IIIA of the compound of Formula A is characterized by an XRPD pattern substantially as shown in FIG. 7. Peaks from the XRPD pattern are listed in Table 3.

In some embodiments, crystalline Form IIIA of the compound of Formula A is characterized by an XRPD pattern comprising a peak, in terms of 2θ, at 8.1°±0.2°. In some embodiments, crystalline Form IIIA of the compound of Formula A is characterized by an XRPD pattern comprising a peak, in terms of 2θ, at 10.6°±0.2°. In some embodiments, crystalline Form IIIA of the compound of Formula A is characterized by an XRPD pattern comprising a peak, in terms of 20, at 13.5°±0.2°. In some embodiments, crystalline Form IIIA of the compound of Formula A is characterized by an XRPD pattern comprising a peak, in terms of 2θ, at 14.2°±0.2°. In some embodiments, crystalline Form IIIA of the compound of Formula A is characterized by an XRPD pattern comprising a peak, in terms of 2θ, at 20.3°±0.2°.

In some embodiments, crystalline Form IIIA of the compound of Formula A has an XRPD pattern comprising the following peaks, in terms of 2θ: 8.1°±0.2°; 10.6°±0.2°;

13.5°±0.2°; and 14.2°±0.2°. In some embodiments, crystalline Form IIIA of the compound of Formula A has an XRPD pattern comprising the following peaks, in terms of 2θ: 10.6°±0.2°; 13.5°±0.2°; 14.2°±0.2°; 16.4°±0.2°; 17.1°±0.2°, 17.9°±0.2°, 20.3°±0.2°, 20.8°±0.2°, 24.1°±0.2°, 24.6°±0.2°, 24.8°±0.2°, and 27.5°±0.2°. In some embodiments, crystalline Form IIIA of the compound of Formula A has an XRPD pattern comprising the following peaks, in terms of 2θ: 10.6°±0.2°; 13.5°±0.2°; 14.2°±0.2°; and 20.3°±0.2°.

In some embodiments, crystalline Form IIIA of the compound of Formula A has an XRPD pattern comprising 2 or more, 3 or more, or 4 or more of the following peaks, in terms of 2θ: 8.1°±0.2°; 10.6°±0.2°, 13.5°±0.2°, 14.2°±0.2°, 16.4°±0.2°, 17.1°±0.2°, 17.9°±0.2°, 20.3°±0.2°, and 24.1°±0.2°. In some embodiments, crystalline Form IIIA of the compound of Formula A has an XRPD pattern comprising 2 or more, 3 or more, or 4 or more of the following peaks, in terms of 2θ: 10.6°±0.2°; 13.5°±0.2°, 14.2°±0.2°, 16.4°±0.2°, 17.1°±0.2°, 17.9°±0.2°, 20.3°±0.2°, 20.8°±0.2°, 24.1°±0.2°, 24.6°±0.2°; 24.8°±0.2°; and 27.5°±0.2°. In some embodiments, crystalline Form IIIA of the compound of Formula A has an XRPD pattern comprising 2 or more, 3 or more, or 4 or more of the following peaks, in terms of 2θ: 10.6°±0.2°, 13.5°±0.2°, 14.2°±0.2°, 16.4°±0.2°, 17.1°±0.2°, 17.9°±0.2°, 20.3°±0.2°, and 24.1°±0.2°.

Figure 8:
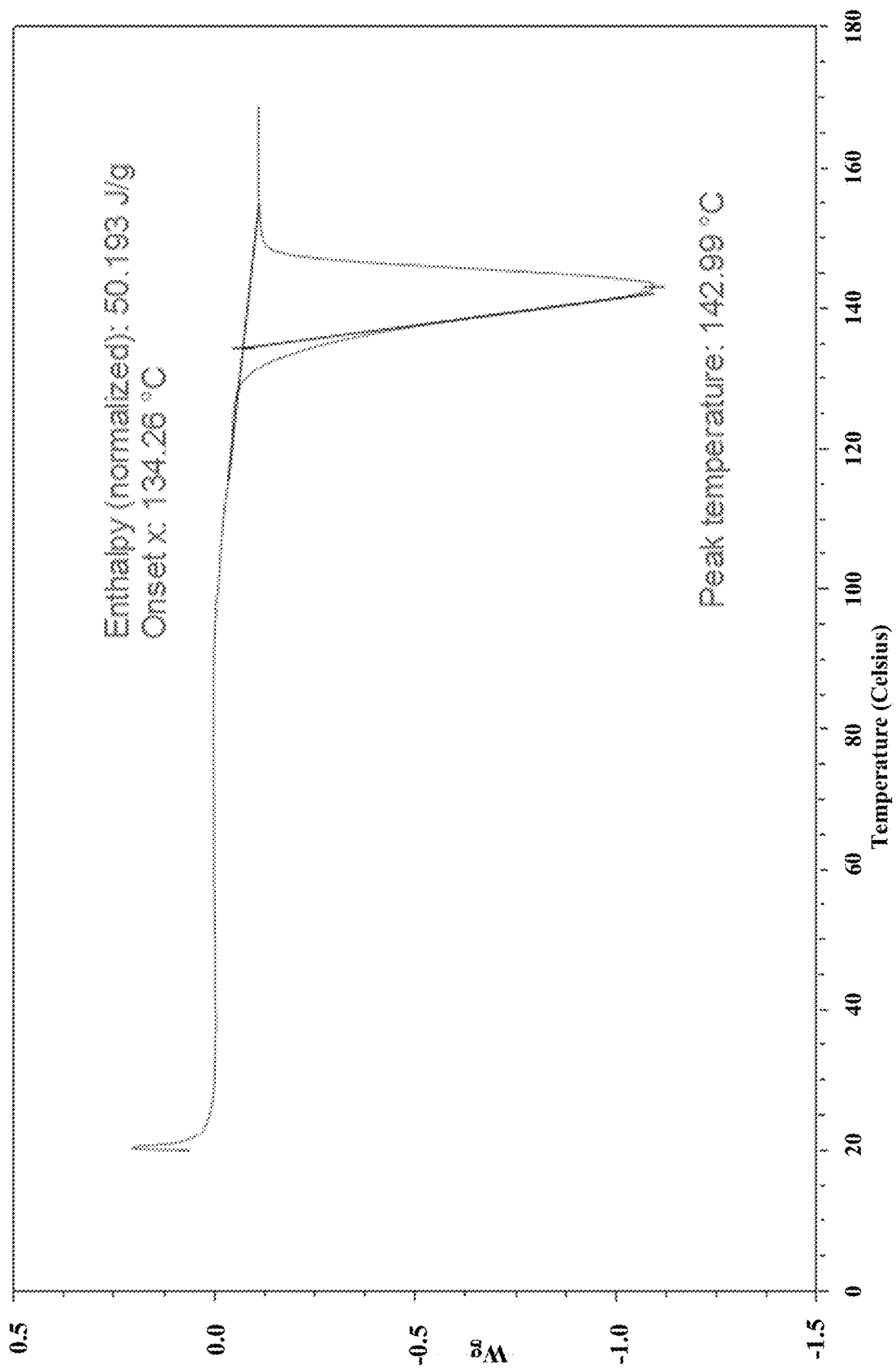
FIG. 8 shows the results of a DSC experiment for 2-(3-(8-amino-6-(trifluoromethyl)imidazo[1,2-a]pyrazin-3-yl)-4-methylphenyl)-3,3,3-trifluoro-2-hydroxypropanamide, crystalline Form IIIA.

In some embodiments, Form IIIA of the compound of Formula A is characterized by a DSC thermogram comprising an endothermic peak having a maximum at about 143° C. In some embodiments, crystalline Form IIIA of the compound of Formula A has a DSC thermogram substantially as shown in FIG. 8.

Figure 9:
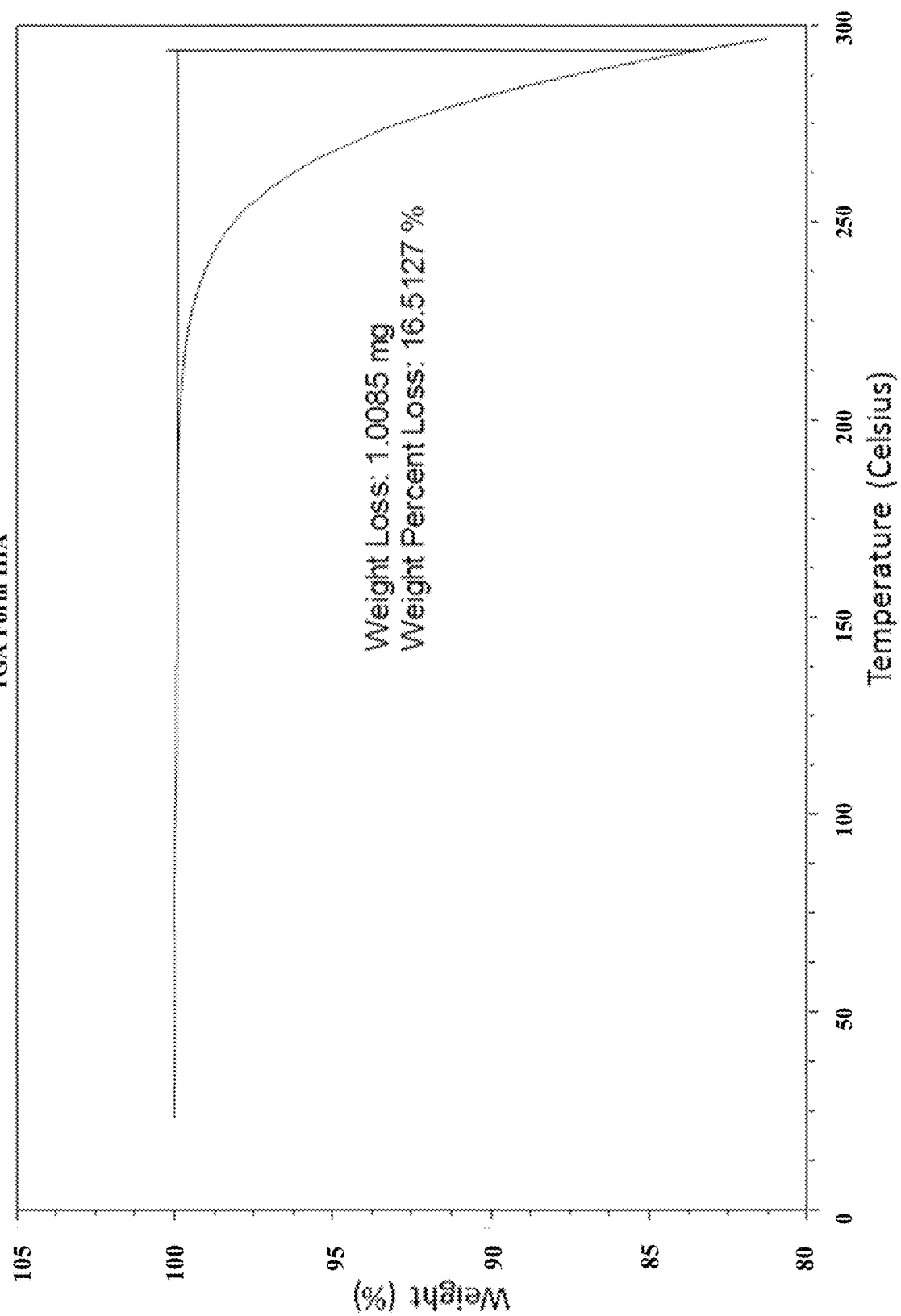
FIG. 9 shows the results of a TGA experiment for 2-(3-(8-amino-6-(trifluoromethyl)imidazo[1,2-a]pyrazin-3-yl)-4-methylphenyl)-3,3,3-trifluoro-2-hydroxypropanamide, crystalline Form IIIA.

In some embodiments, crystalline Form IIIA of the compound of Formula A has a TGA trace substantially as shown in FIG. 9.

Hydrobromic Acid Salt of Formula A

In some embodiments, the present application provides a hydrobromic acid salt of the compound of Formula A. In some embodiments, the hydrobromic acid salt of the compound of Formula A is a 1:1 stoichiometric ratio of 2-(3-(8-amino-6-(trifluoromethyl)imidazo[1,2-a]pyrazin-3-yl)-4-methylphenyl)-3,3,3-trifluoro-2-hydroxypropanamide to hydrobromic acid. The hydrobromic acid salt form can be generally prepared as described in Example 11.

In some embodiments, the hydrobromic acid salt of the compound of Formula A is crystalline. In some embodiments, the hydrobromic acid salt of the compound of Formula A is a solvated crystalline form. In some embodiments, the hydrobromic acid salt of the compound of Formula A is a methanol solvate crystalline form.

Crystalline Forms of the Compound of Formula B

The compound of Formula B can be isolated in numerous crystalline forms, including, for example, crystalline forms which are anhydrous and/or non-solvated. In some embodiments, the crystalline forms of the compound of Formula B are anhydrous. In some embodiments, the crystalline forms of the compound of Formula B are non-solvated. In some embodiments, the crystalline forms of the compound of Formula B are anhydrous and non-solvated. By "anhydrous" is meant that the crystalline form of the compound of Formula B contains essentially no bound water in the crystal lattice structure, i.e., the compound does not form a crystalline hydrate.

In some embodiments, the crystalline forms provided herein can be prepared, for example, by a process comprising dissolving 8-amino-N-(2-hydroxy-2-methylpropyl)-3-(2-methyl-5-(1,1,1-trifluoro-2-hydroxypropan-2-yl)phenyl) imidazo[1,2-a]pyrazine-6-carboxamide in a solvent to form a mixture and crystallizing the compound from the mixture.

In some embodiments, the process further comprises heating the mixture to a temperature of from about 70° C. to about 90° C. In some embodiments, the process further comprises cooling the mixture to room temperature.

In some embodiments, the solvent comprises isopropyl acetate. In some embodiments, the solvent further comprises heptane.

In some embodiments, the present application provides a crystalline form of the compound 8-amino-N-(2-hydroxy-2-methylpropyl)-3-(2-methyl-5-(1,1,1-trifluoro-2-hydroxy-propan-2-yl)phenyl)imidazo[1,2-a]pyrazine-6-carboxamide, which is prepared according to a process provided herein. In some embodiments, the crystalline form is Form IB as described herein. In some embodiments, the crystalline form is Form IIB as described herein.

In some embodiments, the crystalline forms of the invention are substantially isolated. By "substantially isolated" is meant that a particular crystalline form of the compound of Formula B is at least partially isolated from impurities. For example, in some embodiments a crystalline form of the invention comprises less than about 50%, less than about 40%, less than about 30%, less than about 20%, less than about 15%, less than about 10%, less than about 5%, less than about 2.5%, less than about 1%, or less than about 0.5% of impurities. Impurities generally include anything that is not the substantially isolated crystalline form including, for example, other crystalline forms and other substances. In some embodiments, a crystalline form of the compound of Formula B is substantially free of other crystalline forms. The phrase "substantially free of other crystalline forms" means that a particular crystalline form of the compound of Formula B comprises greater than about 80%, greater than about 90%, greater than about 95%, greater than about 98%, greater than about 99% or greater than about 99.5% by weight of the particular crystalline form.

Crystalline Form IB of the Compound of Formula B

In some embodiments, the crystalline form of the compound of Formula B is Form IB. In some embodiments, crystalline Form IB of the compound of Formula B is anhydrous and non-solvated. The preparation of the compound of Formula B is described in Examples 5 and 6. Crystalline Form IB can be generally prepared as described in Example 7.

Figure 10:
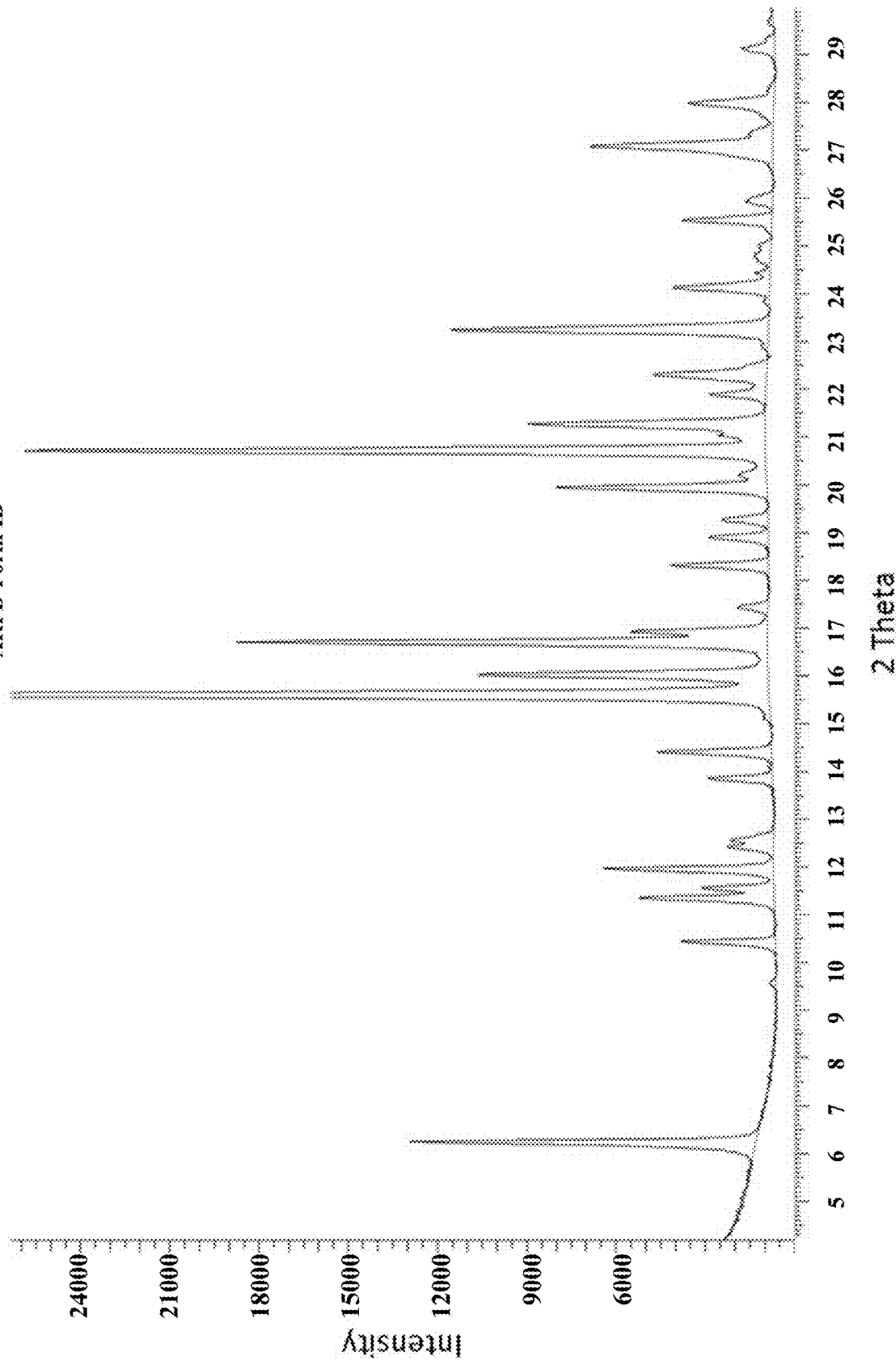
FIG. 10 shows an XRPD pattern for 8-amino-N-(2-hydroxy-2-methylpropyl)-3-(2-methyl-5-(1,1,1-trifluoro-2-hydroxypropan-2-yl)phenyl)imidazo[1,2-a]pyrazine-6-carboxamide, crystalline Form IB.

Crystalline Form IB of the compound of Formula B can be identified by unique signatures with respect to, for example, X-ray powder diffraction (XRPD) and differential scanning calorimetry (DSC). In some embodiments, crystalline Form IB of the compound of Formula B is characterized by an XRPD pattern substantially as shown in FIG. 10. Peaks from the XRPD pattern are listed in Table 4.

In some embodiments, crystalline Form IB of the compound of Formula B is characterized by an XRPD pattern comprising a peak, in terms of 2θ, at 6.2°±0.2°. In some embodiments, crystalline Form IB of the compound of Formula B is characterized by an XRPD pattern comprising a peak, in terms of 2θ, at 15.6°±0.2°. In some embodiments, crystalline Form IB of the compound of Formula B is characterized by an XRPD pattern comprising a peak, in terms of 2θ, at 20.7°±0.2°. In some embodiments, crystalline Form IB of the compound of Formula B has an XRPD pattern comprising the following peaks, in terms of 2θ: 6.2°±0.2°; 15.6°±0.2°; 16.7°±0.2°; 20.7°±0.2°; and 23.2°±0.2°. In some embodiments, crystalline Form IB of the compound of Formula B has an XRPD pattern comprising the following peaks, in terms of 2θ: 6.2°±0.2°;

10.4°±0.2°; 11.4°±0.2°; 11.6°±0.2°; 12.0°±0.2°; 13.9°±0.2°; 14.4°±0.2°; 15.6°±0.2°; 16.0°±0.2°; 16.7°±0.2°; 20.7°±0.2°; and 23.2°±0.2°. In some embodiments, crystalline Form IB of the compound of Formula B has an XRPD pattern comprising the following peaks, in terms of 2θ: 6.2°±0.2°; 12.0°±0.2°; 15.6°±0.2°; 16.0°±0.2°; 16.7°±0.2°; 19.3°±0.2°; 20.7°±0.2°; 23.2°±0.2°; and 27.1°±0.2°. In some embodiments, crystalline Form IB of the compound of Formula B has an XRPD pattern comprising the following peaks, in terms of 2θ: 6.2°±0.2°; 10.4°±0.2°; 11.4°±0.2°; 11.6°±0.2°; 12.0°±0.2°; 13.9°±0.2°; and 14.4°±0.2°.

In some embodiments, crystalline Form IB of the compound of Formula B has an XRPD pattern comprising 2 or more, 3 or more, or 4 or more of the following peaks, in terms of 2θ: 2θ: 6.2°±0.2°; 10.4°±0.2°; 11.4°±0.2°; 11.6°±0.2°; 12.0°±0.2°; 13.9°±0.2°; 14.4°±0.2°; 15.6°±0.2°; 16.0°±0.2°; 16.7°±0.2°; 20.7°±0.2°; and 23.2°±0.2°. In some embodiments, crystalline Form IB of the compound of Formula B has an XRPD pattern comprising 2 or more, 3 or more, or 4 or more of the following peaks, in terms of 2θ: 6.2°±0.2°; 12.0°±0.2°; 15.6°±0.2°; 16.0°±0.2°; 16.7°±0.2°; 19.3°±0.2°; 20.7°±0.2°; 23.2°±0.2°; and 27.1°±0.2°. In some embodiments, crystalline Form IB of the compound of Formula B has an XRPD pattern comprising 2 or more, 3 or more, or 4 or more of the following peaks, in terms of 2θ: 6.2°±0.2°; 15.6°±0.2°; 16.0°±0.2°; 16.7°±0.2°; 20.7°±0.2°; and 23.2°±0.2°. In some embodiments, crystalline Form IB of the compound of Formula B has an XRPD pattern comprising 2 or more, 3 or more, or 4 or more of the following peaks, in terms of 2θ: 6.2°±0.2°; 10.4°±0.2°; 11.4°±0.2°; 11.6°±0.2°; 12.0°±0.2°; 13.9°±0.2°; and 14.4°±0.2°.

Figure 11:
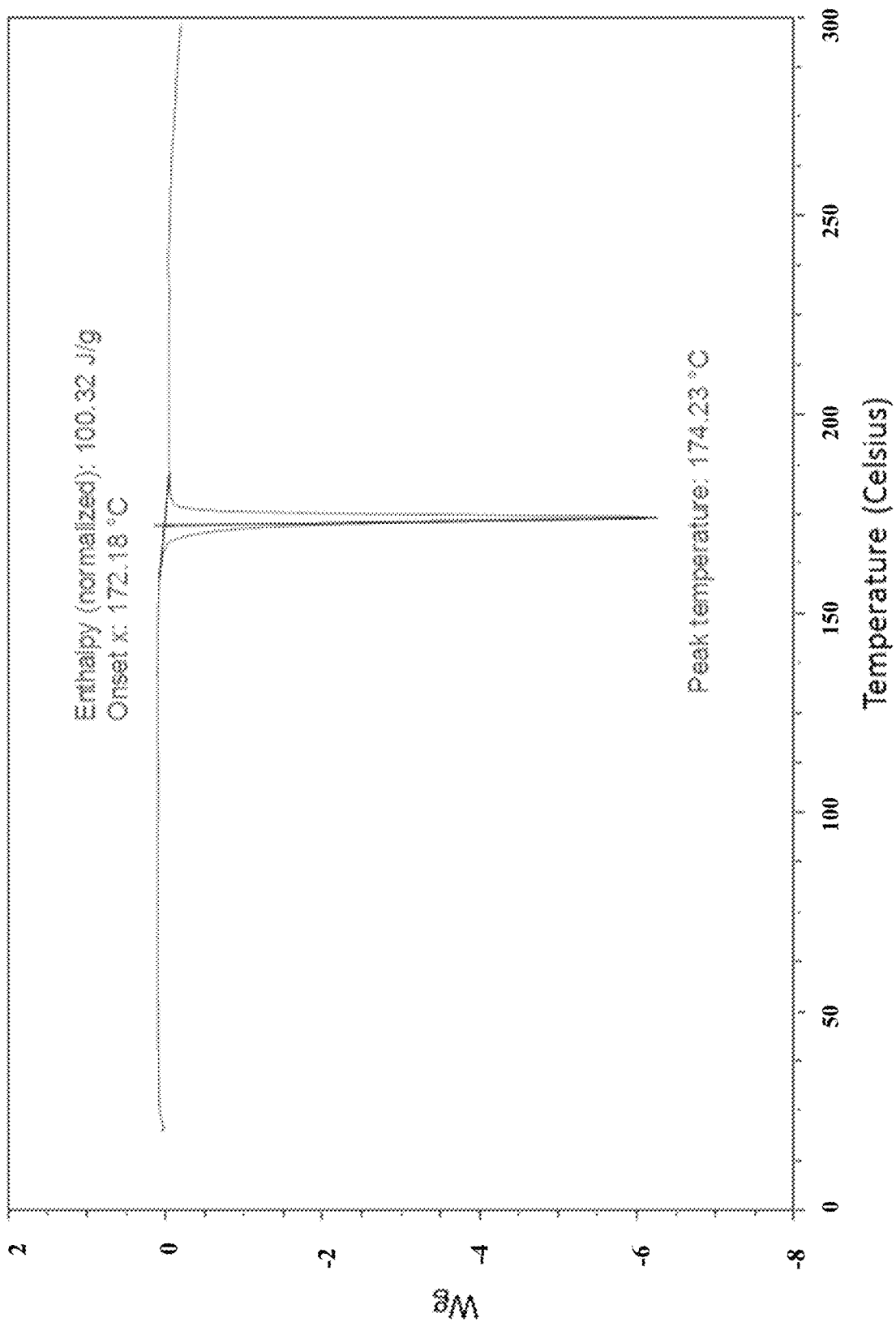
FIG. 11 shows the results of a DSC experiment for 8-amino-N-(2-hydroxy-2-methylpropyl)-3-(2-methyl-5-(1,1,1-trifluoro-2-hydroxypropan-2-yl)phenyl)imidazo[1,2-a]pyrazine-6-carboxamide, crystalline Form IB.

In some embodiments, Form IB of the compound of Formula B is characterized by a DSC thermogram comprising an endothermic peak having a maximum at about 174° C. In some embodiments, crystalline Form IB of the compound of Formula B has a DSC thermogram substantially as shown in FIG. 11.

Crystalline Form IIB of the Compound of Formula B

In some embodiments, the crystalline form of the compound of Formula B is Form IIB. In some embodiments, crystalline Form IIB of the compound of Formula B is anhydrous and non-solvated. This crystalline form can be generally prepared as described in Example 8.

Figure 12:
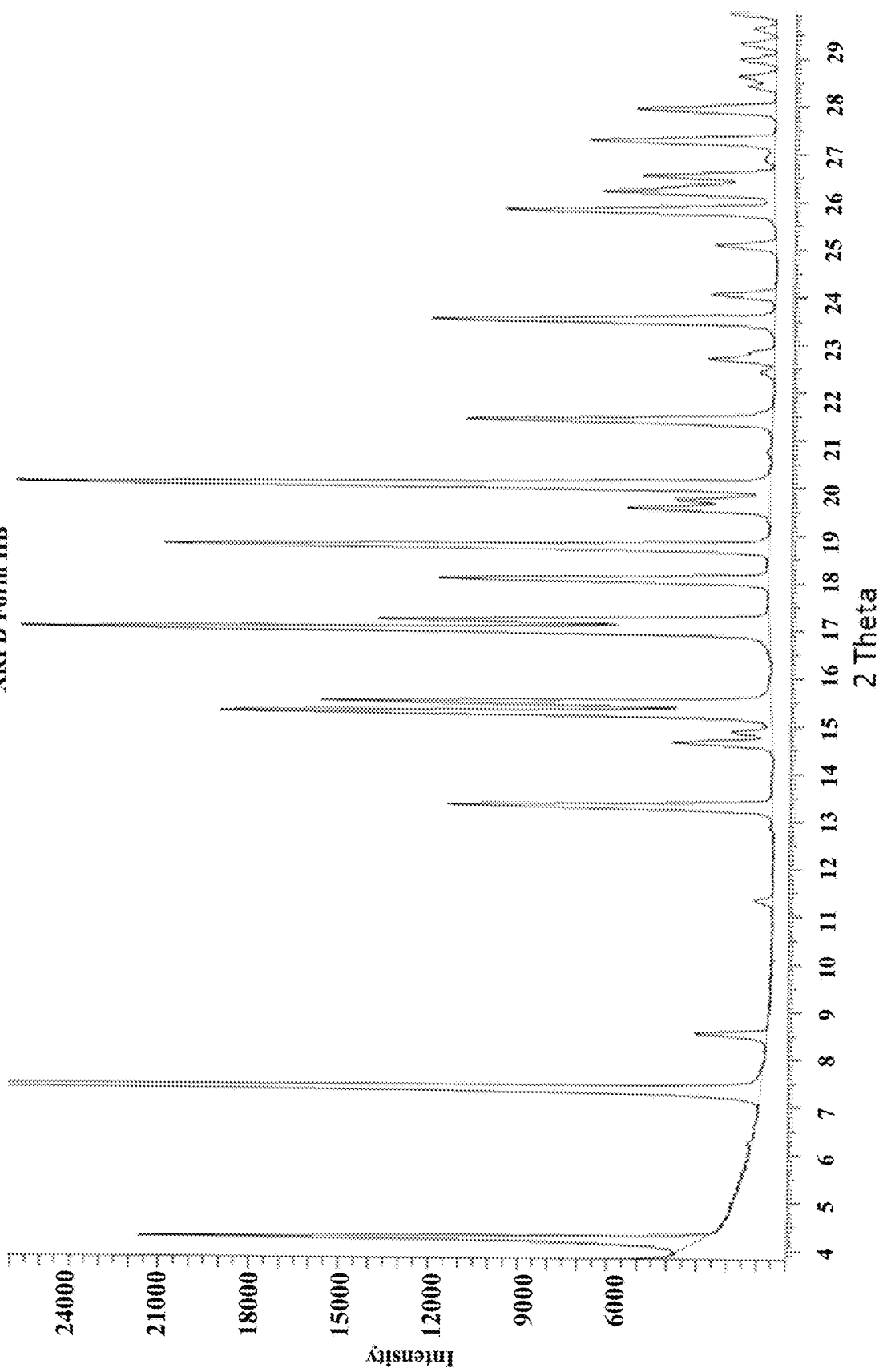
FIG. 12 shows an XRPD pattern for 8-amino-N-(2-hydroxy-2-methylpropyl)-3-(2-methyl-5-(1,1,1-trifluoro-2-hydroxypropan-2-yl)phenyl)imidazo[1,2-a]pyrazine-6-carboxamide, crystalline Form IIB.

Crystalline Form IIB of the compound of Formula B can be identified by unique signatures with respect to, for example, X-ray powder diffraction (XRPD) and differential scanning calorimetry (DSC). In some embodiments, crystalline Form IIB of the compound of Formula B is characterized by an XRPD pattern substantially as shown in FIG. 12. Peaks from the XRPD pattern are listed in Table 5.

In some embodiments, crystalline Form IIB of the compound of Formula B is characterized by an XRPD pattern comprising a peak, in terms of 2θ, at 4.2°±0.2°. In some embodiments, crystalline Form IIB of the compound of Formula B is characterized by an XRPD pattern comprising a peak, in terms of 2θ, at 7.4°±0.2°. In some embodiments, crystalline Form IIB of the compound of Formula B is characterized by an XRPD pattern comprising a peak, in terms of 2θ, at 13.3°±0.2°. In some embodiments, crystalline Form IIB of the compound of Formula B is characterized by an XRPD pattern comprising a peak, in terms of 2θ, at 20.1°±0.2°. In some embodiments, crystalline Form IIB of the compound of Formula B is characterized by an XRPD pattern comprising a peak, in terms of 2θ, at 17.0°±0.2°. In some embodiments, crystalline Form IIB of the compound of Formula B is characterized by an XRPD pattern comprising a peak, in terms of 2θ, at 18.8°±0.2°.

In some embodiments, crystalline Form IIB of the compound of Formula B has an XRPD pattern comprising the following peaks, in terms of 2θ: 4.3°±0.2°; 7.4°±0.2°; 13.3°±0.2°; and 15.3°±0.2°. In some embodiments, crystalline Form IIB of the compound of Formula B has an XRPD pattern comprising the following peaks, in terms of 2θ: 4.3°±0.2°; 7.4°±0.2°; 15.3°±0.2°; 17.0°±0.2°; 18.8°±0.2°; and 20.1°±0.2°. In some embodiments, crystalline Form IIB of the compound of Formula B has an XRPD pattern comprising the following peaks, in terms of 2θ: 4.3°±0.2°; 7.4°±0.2°; 13.3°±0.2°; 15.3°0.2°; 15.5°±0.2°; 17.0°±0.2°; 17.2°±0.2°; 18.1°±0.2°; 18.8°±0.2°; 19.6°±0.2°; 20.1°±0.2°; 21.4°±0.2°; 23.5°±0.2°; 25.8°±0.2°; 26.2°±0.2°; and 27.3°±0.2°.

In some embodiments, crystalline Form IIB of the compound of Formula B has an XRPD pattern comprising 2 or more, 3 or more, or 4 or more of the following peaks, in terms of 2θ: 4.3°±0.2°; 7.4°±0.2°; 13.3°±0.2°; 15.3°±0.2°; 15.5°±0.2°; 17.0°±0.2°; 17.2°±0.2°; 18.1°±0.2°; 18.8°±0.2°; 19.6°±0.2°; 20.1°±0.2°; 21.4°±0.2°; 23.5°±0.2°; 25.8°±0.2°; 26.2°±0.2°; and 27.3°±0.2°. In some embodiments, crystalline Form IIB of the compound of Formula B has an XRPD pattern comprising 2 or more, 3 or more, or 4 or more of the following peaks, in terms of 2θ: 4.3°±0.2°; 7.4°±0.2°; 13.3°±0.2°; 15.3°±0.2°; 15.5°±0.2°; 17.0°±0.2°; 17.2°±0.2°; 18.8°±0.2°; and 20.1°±0.2°.

Figure 13:
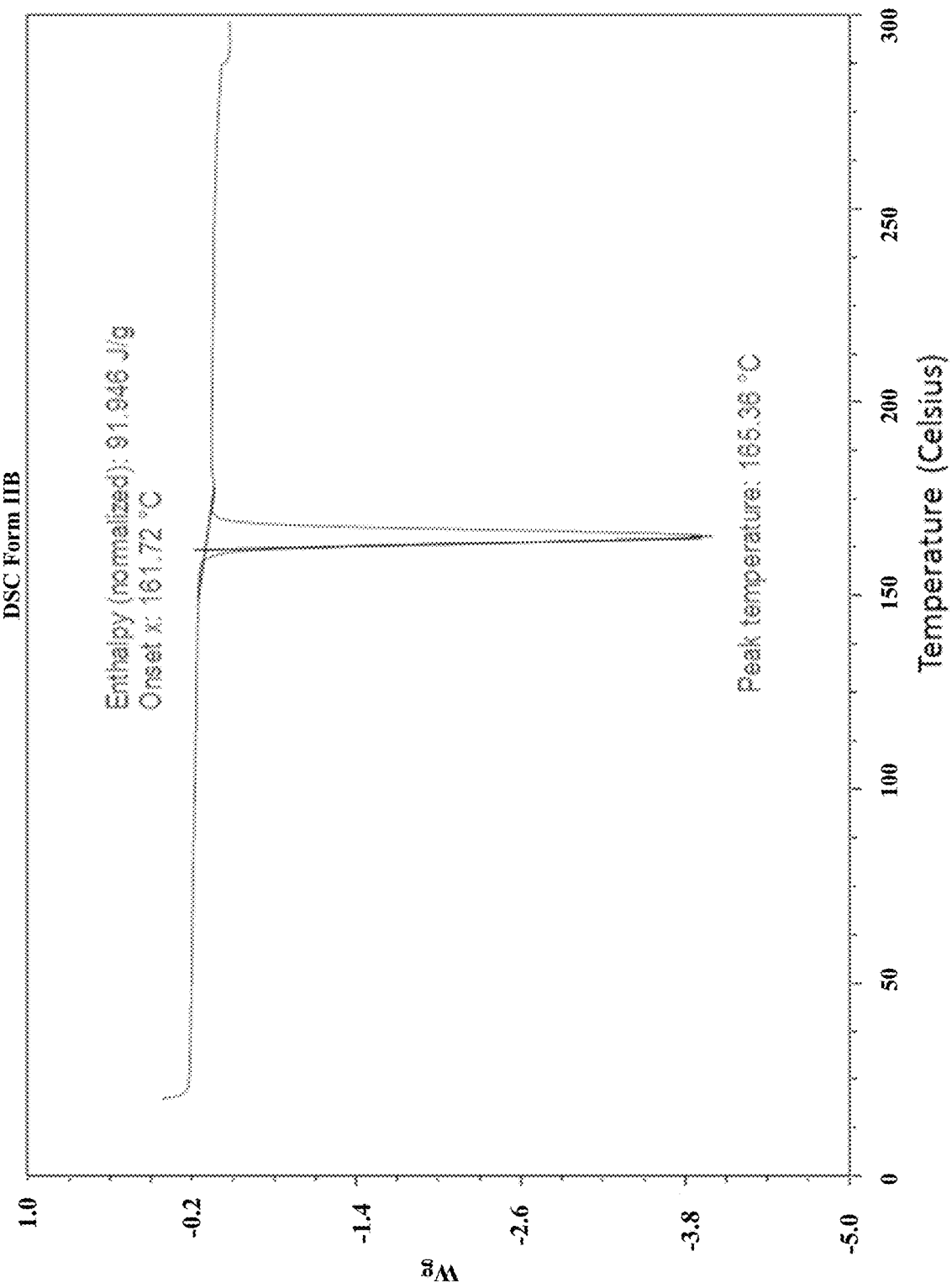
FIG. 13 shows the results of a DSC experiment for 8-amino-N-(2-hydroxy-2-methylpropyl)-3-(2-methyl-5-(1,1,1-trifluoro-2-hydroxypropan-2-yl)phenyl)imidazo[1,2-a]pyrazine-6-carboxamide, crystalline Form IIB.

In some embodiments, Form IIB of the compound of Formula B is characterized by a DSC thermogram comprising an endothermic peak having a maximum at about 165° C. In some embodiments, crystalline Form IIB of the compound of Formula B has a DSC thermogram substantially as shown in FIG. 13.

Crystalline Forms of the Compound of Formula C

The compound of Formula C can be isolated in numerous crystalline forms, including, for example, crystalline forms which are anhydrous and/or non-solvated. In some embodiments, the crystalline forms of the compound of Formula C are anhydrous. In some embodiments, the crystalline forms of the compound of Formula C are non-solvated. In some embodiments, the crystalline forms of the compound of Formula C are anhydrous and non-solvated. By "anhydrous" is meant that the crystalline form of the compound of Formula C contains essentially no bound water in the crystal lattice structure, i.e., the compound does not form a crystalline hydrate.

In some embodiments, the present application provides a process of preparing a crystalline form of the compound 8-amino-N-(2-hydroxy-2-methylpropyl)-3-(2-(methyl-d$_3$)-5-(1,1,1-trifluoro-2-hydroxypropan-2-yl)phenyl)imidazo[1,2-a]pyrazine-6-carboxamide. In some embodiments, the process comprises dissolving 8-amino-N-(2-hydroxy-2-methylpropyl)-3-(2-(methyl-d$_3$)-5-(1,1,1-trifluoro-2-hydroxypropan-2-yl)phenyl)imidazo[1,2-a]pyrazine-6-carboxamide in a solvent to form a mixture and crystallizing the compound from the mixture.

In some embodiments, the process further comprises heating the mixture to a temperature of from about 70° C. to about 90° C. In some embodiments, the process further comprises cooling the mixture to room temperature.

In some embodiments, the solvent comprises isopropyl acetate. In some embodiments, the solvent further comprises heptane.

The present application further provides a crystalline form of the compound 8-amino-N-(2-hydroxy-2-methylpropyl)-3-(2-(methyl-d$_3$)-5-(1,1,1-trifluoro-2-hydroxypropan-2-yl)

phenyl)imidazo[1,2-a]pyrazine-6-carboxamide, which is prepared according a process provided herein. In some embodiments, the crystalline form is Form IC as described herein.

In some embodiments, the crystalline forms of the invention are substantially isolated. By "substantially isolated" is meant that a particular crystalline form of the compound of Formula C is at least partially isolated from impurities. For example, in some embodiments a crystalline form of the invention comprises less than about 50%, less than about 40%, less than about 30%, less than about 20%, less than about 15%, less than about 10%, less than about 5%, less than about 2.5%, less than about 1%, or less than about 0.5% of impurities. Impurities generally include anything that is not the substantially isolated crystalline form including, for example, other crystalline forms and other substances.

In some embodiments, a crystalline form of the compound of Formula C is substantially free of other crystalline forms. The phrase "substantially free of other crystalline forms" means that a particular crystalline form of the compound of Formula C comprises greater than about 80%, greater than about 90%, greater than about 95%, greater than about 98%, greater than about 99% or greater than about 99.5% by weight of the particular crystalline form.

Crystalline Form IC of the Compound of Formula C

In some embodiments, the crystalline form of the compound of Formula C is crystalline Form IC. In some embodiments, crystalline Form IC of the compound of Formula C is anhydrous and non-solvated. The preparation of the compound of Formula C of the compound of Formula C is described in Example 9. Crystalline Form IC of the compound of Formula C can be generally prepared as described in Example 10.

Figure 14:
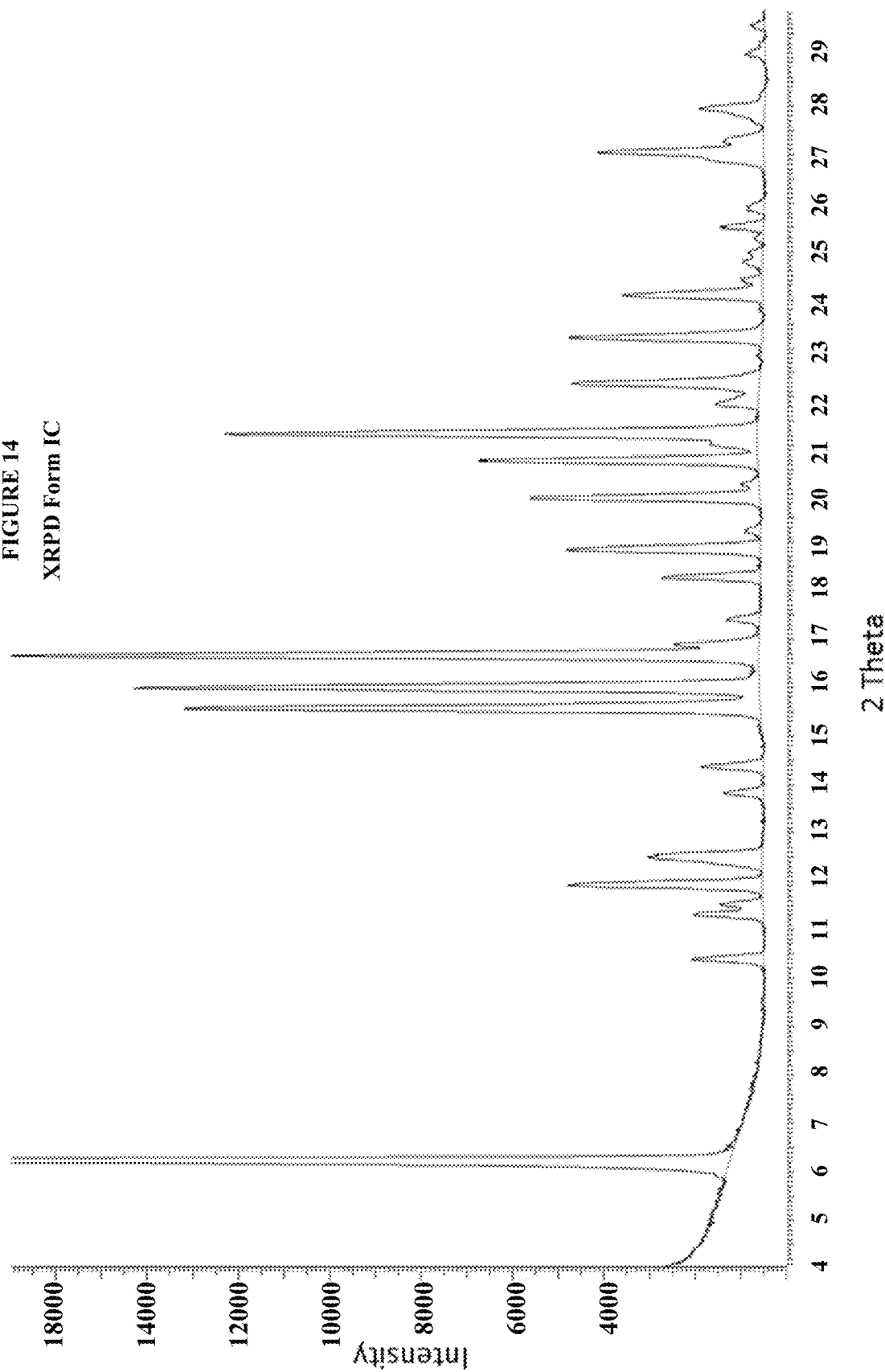
FIG. 14 shows an XRPD pattern for 8-amino-N-(2-hydroxy-2-methylpropyl)-3-(2-(methyl-$d_3$)-5-(1,1,1-trifluoro-2-hydroxypropan-2-yl)phenyl)imidazo[1,2-a]pyrazine-6-carboxamide, crystalline Form IC.

Crystalline Form IC of the compound of Formula C can be identified by unique signatures with respect to, for example, X-ray powder diffraction (XRPD) and differential scanning calorimetry (DSC). In some embodiments, crystalline Form IC of the compound of Formula C is characterized by an XRPD pattern substantially as shown in FIG. 14. Peaks from the XRPD pattern are listed in Table 6.

In some embodiments, crystalline Form IC of the compound of Formula C is characterized by an XRPD pattern comprising a peak, in terms of 2θ, at 6.2°±0.2°. In some embodiments, crystalline Form IC of the compound of Formula C is characterized by an XRPD pattern comprising a peak, in terms of 2θ, at 11.9°±0.2°. In some embodiments, crystalline Form IC of the compound of Formula C is characterized by an XRPD pattern comprising a peak, in terms of 2θ, at 16.7°±0.2°. In some embodiments, crystalline Form IC of the compound of Formula C has an XRPD pattern comprising the following peaks, in terms of 2θ: 6.2°±0.2°; 15.6°±0.2°; 16.0°±0.2°; 16.7°±0.2°; 18.8°±0.2°; 19.9°±0.2°; 20.7°±0.2°; 21.2°±0.2°; 22.3°±0.2°; 23.2°±0.2°; and 27.0°±0.2°. In some embodiments, crystalline Form IC of the compound of Formula C has an XRPD pattern comprising the following peaks, in terms of 2θ: 6.2°±0.2°; 15.6°±0.2°; 16.0°±0.2°; 16.7°±0.2°; and 21.2°±0.2°. In some embodiments, crystalline Form IC of the compound of Formula C has an XRPD pattern comprising the following peaks, in terms of 2θ: 6.2°±0.2°; 10.4°±0.2°; 11.3°±0.2°; 11.9°±0.2°; and 12.5°±0.2°.

In some embodiments, crystalline Form IC of the compound of Formula C has an XRPD pattern comprising 2 or more, 3 or more, or 4 or more of the following peaks, in terms of 2θ: 6.2°±0.2°; 15.6°±0.2°; 16.0°±0.2°; 16.7°±0.2°; 18.8°±0.2°; 19.9°±0.2°; 20.7°±0.2°; 21.2°±0.2°; 22.3°±0.2°; 23.2°±0.2°; and 27.0°±0.2°. In some embodiments, crystalline Form IC of the compound of Formula C has an XRPD pattern comprising 2 or more, 3 or more, or 4 or more of the following peaks, in terms of 2θ: 6.2°±0.2°; 10.4°±0.2°; 11.3°±0.2°; 11.9°±0.2°; 12.5°±0.2°; 13.8°±0.2°; 14.4°±0.2°; 15.6°±0.2°; 16.0°±0.2°; 16.7°±0.2°; 20.7°±0.2°; and 21.2°±0.2°. In some embodiments, crystalline Form IC of the compound of Formula C has an XRPD pattern comprising 2 or more, 3 or more, or 4 or more of the following peaks, in terms of 2θ: 6.2°±0.2°; 15.6°±0.2°; 16.0°±0.2°; 16.7°±0.2°; 20.7°±0.2°; and 21.2°±0.2°.

Figure 15:
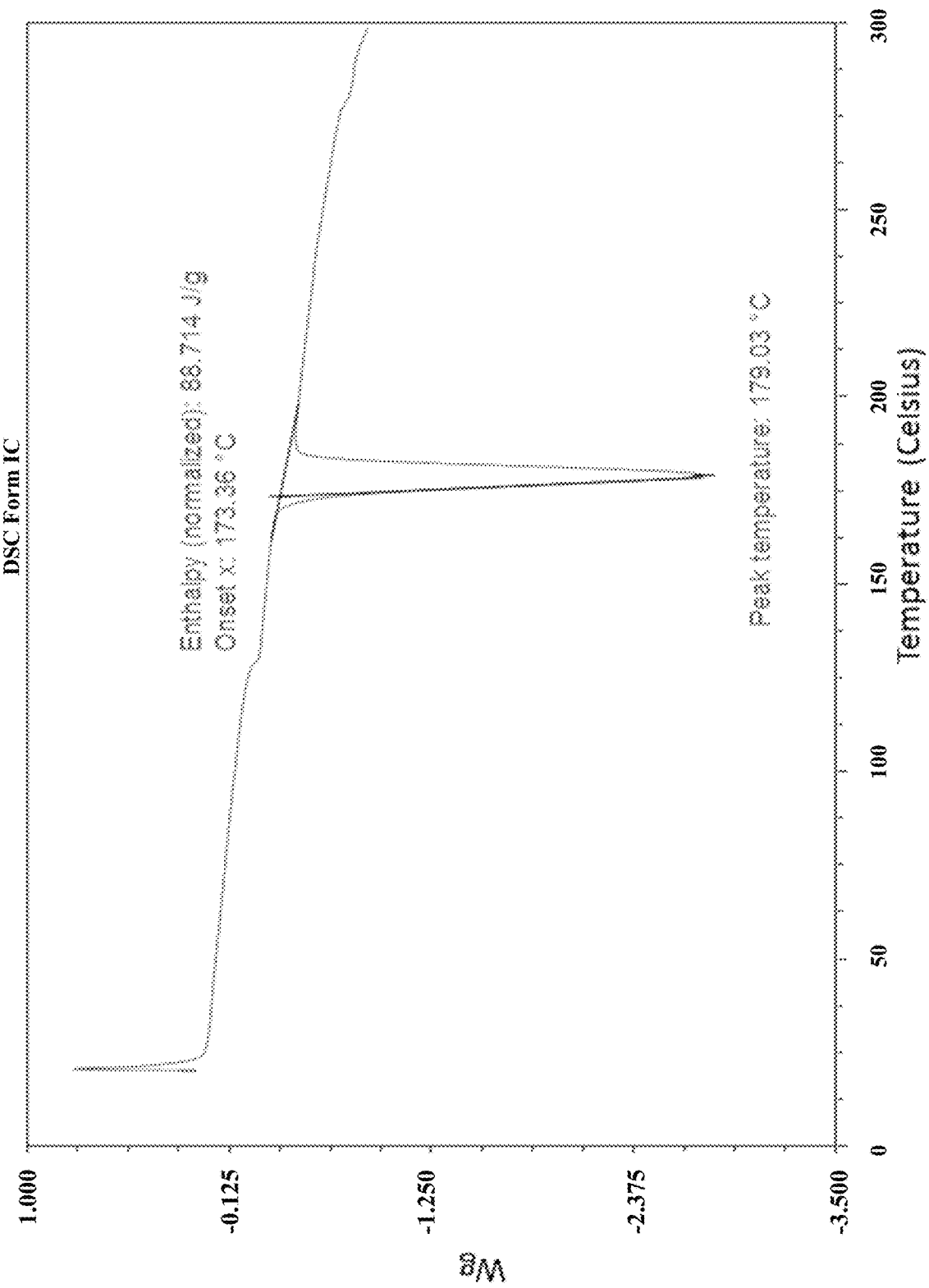
FIG. 15 shows the results of a DSC experiment for 8-amino-N-(2-hydroxy-2-methylpropyl)-3-(2-(methyl-$d_3$)-5-(1,1,1-trifluoro-2-hydroxypropan-2-yl)phenyl)imidazo[1,2-a]pyrazine-6-carboxamide, crystalline Form IC.

In some embodiments, Form IC of the compound of Formula C is characterized by a DSC thermogram comprising an endothermic peak having a maximum at about 179° C. In some embodiments, crystalline Form IC of the compound of Formula C has a DSC thermogram substantially as shown in FIG. 15.

Methods of Use

The compounds (e.g., salts and crystalline forms) of the invention described herein inhibit activity of PI3Kγ kinase. Accordingly, the salts and crystalline forms of the invention described herein can be used in methods of inhibiting PI3Kγ kinase by contacting the kinase. In some embodiments, the salts and crystalline forms of the invention can be used in methods of inhibiting activity of PI3Kγ in an individual/patient in need of the inhibition by administering an effective amount of a salt or crystalline form described herein. In some embodiments, modulating is inhibiting. In some embodiments, the contacting is in vivo. In some embodiments, the contacting is ex vivo. Advantageously, the crystalline forms as described herein demonstrate better efficacy and favorable safety and toxicity profiles in animal studies.

In some embodiments, the PI3Kγ includes a mutation. A mutation can be a replacement of one amino acid for another, or a deletion of one or more amino acids. In such embodiments, the mutation can be present in the kinase domain of the PI3Kγ.

In some embodiments, the salt or crystalline form further inhibits PI3Kδ.

The salts and crystalline forms described herein can be selective. By "selective" is meant that the salt or crystalline form binds to or inhibits PI3Kγ with greater affinity or potency, respectively, compared to at least one other kinase. In some embodiments, the salts and crystalline forms of the disclosure are selective inhibitors of PI3Kγ over PI3Kδ, PI3Kα, and PI3Kβ. In some embodiments, the salts and crystalline forms of the disclosure are selective inhibitors of PI3Kγ over PI3Kα and PI3Kβ. In some embodiments, selectivity can be at least about 2-fold, 3-fold, 5-fold, 10-fold, at or 20-fold over PI3Kδ as measured by the assays described herein. In some embodiments, selectivity can be tested at the 2 μM ATP concentration of each enzyme. In some embodiments, the selectivity of salts and crystalline forms of the disclosure can be determined by cellular assays associated with particular PI3K kinase activity.

Another aspect of the present disclosure pertains to methods of treating a kinase PI3Kγ-associated disease or disorder in an individual (e.g., patient) by administering to the individual in need of such treatment a therapeutically effective amount or dose of one or more salts or crystalline forms of the present disclosure or a pharmaceutical composition thereof. A PI3Kγ-associated disease or disorder can include any disease, disorder or condition that is directly or indirectly linked to expression or activity of the PI3Kγ, including overexpression and/or abnormal activity levels.

In some embodiments, the disease or disorder is an autoimmune disease or disorder, cancer, cardiovascular disease, or neurodegenerative disease.

In some embodiments, the disease or disorder is lung cancer (e.g., non-small cell lung cancer), melanoma, pancreatic cancer, breast cancer, prostate cancer, liver cancer, color cancer, endometrial cancer, bladder cancer, skin cancer, cancer of the uterus, renal cancer, gastric cancer, or sarcoma. In some embodiments, the sarcoma is Askin's tumor, sarcoma botryoides, chondrosarcoma, Ewing's sarcoma, malignant hemangioendothelioma, malignant schwannoma, osteosarcoma, alveolar soft part sarcoma, angiosarcoma, cystosarcoma phyllodes, dermatofibrosarcoma protuberans, desmoid tumor, desmoplastic small round cell tumor, epithelioid sarcoma, extraskeletal chondrosarcoma, extraskeletal osteosarcoma, fibrosarcoma, gastrointestinal stromal tumor (GIST), hemangiopericytoma, hemangiosarcoma, Kaposi's sarcoma, leiomyosarcoma, liposarcoma, lymphangiosarcoma, lymphosarcoma, malignant peripheral nerve sheath tumor (MPNST), neurofibrosarcoma, rhabdomyosarcoma, synovial sarcoma, or undifferentiated pleomorphic sarcoma.

In some embodiments, the disease or disorder is mesothelioma or adrenocarcinoma. In some embodiments, the disease or disorder is mesothelioma. In some embodiments, the disease or disorder is adrenocarcinoma.

In some embodiments, the disease or disorder is acute myeloid leukemia (e.g., acute monocytic leukemia), small lymphocyctic lymphoma, chronic lymphocytic leukemia (CLL), chronic myelogenous leukemia (CML), multiple myeloma, T-cell actute lymphoblasic leukemia (T-ALL), cutaneous T-cell lymphoma, large granular lymphocytic leukemia, mature (peripheral) t-cell neoplasm (PTCL), anaplastic large cell lymphoma (ALCL), or lymphoblastic lymphoma. In some embodiments, the mature (peripheral) t-cell neoplasm (PTCL) is T-cell prolymphocytic leukemia, T-cell granular lymphocytic leukemia, aggressive NK-cell leukemia, mycosis fungoides/Sezary syndrome, naplastic large cell lymphoma (T-cell type), enteropathy type T-cell lymphoma, adult T-cell leukemia/lymphoma, or angioimmunoblastic T-cell lymphoma In some embodiments, the anaplastic large cell lymphoma (ALCL) is systemic ALCL or primary cutaneous ALCL.

In some embodiments, the disease or disorder is Burkitt's lymphoma, acute myeloblastic leukemia, chronic myeloid leukemia, non-Hodgkin's lymphoma, Hodgkin's lymphoma, hairy cell leukemia, Mantle cell lymphoma, small lymphocytic lymphoma, follicular lymphoma, xenoderoma pigmentosum, keratoctanthoma, lymphoplasmacytic lymphoma, extranodal marginal zone lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma (aka asymptomatic myeloma), monoclonal gammopathy of undetermined significance (MGUS), or diffuse large B cell lymphoma.

MDSC (myeloid-derived suppressor cells) are a heterogenous group of immune cells from the myeloid lineage (a family of cells that originate from bone marrow stem cells). MDSCs strongly expand in pathological situations such as chronic infections and cancer, as a result of an altered haematopoiesis. MDSCs are discriminated from other myeloid cell types in which they possess strong immuno-suppressive activities rather than immunostimulatory properties. Similar to other myeloid cells, MDSCs interact with other immune cell types including T cells, dendritic cells, macrophages and natural killer cells to regulate their functions. In some embodiments, the compounds, etc. described herein can be used in methods related to cancer tissue (e.g., tumors) with high infiltration of MDSCs, including Solid tumors with high basal level of macrophage and/or MDSC infiltration.

In some embodiments, the disease or disorder is Burkitt's lymphoma, acute myeloblastic leukemia, chronic myeloid leukemia, non-Hodgkin's lymphoma, Hodgkin's lymphoma, hairy cell leukemia, Mantle cell lymphoma, small lymphocytic lymphoma, follicular lymphoma, lymphoplasmacytic lymphoma, extranodal marginal zone lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma (aka asymptomatic myeloma), monoclonal gammopathy of undetermined significance (MGUS), or diffuse large B cell lymphoma.

In some embodiments, the non-Hodgkin's lymphoma (NHL) is relapsed NHL, refractory NHL, recucurrent follicular NHL, indolent NHL (iNHL), or aggressive NHL (aNHL).

In some embodiments, the diffuse large B cell lymphoma is activated B-cell like (ABC) diffuse large B cell lymphoma, or germinal center B cell (GCB) diffuse large B cell lymphoma.

In some embodiments, the Burkitt's lymphoma is endemic Burkitt's lymphoma, sporadic Burkitt's lymphoma, or Burkitt's-like lymphoma.

In some embodiments, the disease or disorder is rheumatoid arthritis, multiple sclerosis, systemic lupus erythematous, asthma, allergy (e.g, allergic rhinitis), pancreatitis, psoriasis, anaphylaxis, glomerulonephritis, inflammatory bowel disease (e.g., Crohn's disease and ulcerative colitis), thrombosis, meningitis, encephalitis, diabetic retinopathy, benign prostatic hypertrophy, myasthenia gravis, Sjögren's syndrome, osteoarthritis, restenosis, or atherosclerosis.

In some embodiments, the disease or disorder is heart hypertropy, cardiac myocyte dysfunction, acute coronary syndrome, chronic obstructive pulmonary disease (COPD), chronic bronchitis, elevated blood pressure, ischemia, ischemia-reperfusion, vasoconstriction, anemia (e.g., hemolytic anemia, aplastic anemia, or pure red cell anemia), bacterial infection, viral infection, graft rejection, kidney disease, anaphylactic shock fibrosis, skeletal muscle atrophy, skeletal muscle hypertrophy, angiogenesis, sepsis, graft-versus-host disease, allogeneic or xenogeneic transplantation, glomerulosclerosis, progressive renal fibrosis, idiopathic thrombocytopenic purpura (ITP), idiopathic pulmonary fibrosis, autoimmune hemolytic anemia, vasculitis, lupus nephritis, pemphigus, or membranous nephropathy.

In some embodiments, disease or disorder is heart hypertropy, cardiac myocyte dysfunction, chronic obstructive pulmonary disease (COPD), elevated blood pressure, ischemia, ischemia-reperfusion, vasoconstriction, anemia (e.g., hemolytic anemia, aplastic anemia, or pure red cell anemia), bacterial infection, viral infection, graft rejection, kidney disease, anaphylactic shock fibrosis, skeletal muscle atrophy, skeletal muscle hypertrophy, angiogenesis, sepsis, graft rejection, glomerulosclerosis, progressive renal fibrosis, idiopathic thrombocytopenic purpura (ITP), autoimmune hemolytic anemia, vasculitis, systemic lupus erythematosus, lupus nephritis, pemphigus, or membranous nephropathy.

In some embodiments, the disease or disorder is Alzheimer's disease, central nervous system trauma, or stroke.

In some embodiments, the idiopathic thrombocytopenic purpura (ITP) is relapsed ITP or refractory ITP.

In some embodiments, the vasculitis is Behcet's disease, Cogan's syndrome, giant cell arteritis, polymyalgia rheumatica (PMR), Takayasu's arteritis, Buerger's disease (thromboangiitis obliterans), central nervous system vasculitis, Kawasaki disease, polyarteritis nodosa, Churg-Strauss syndrome, mixed cryoglobulinemia vasculitis (essential or hepatitis C virus (HCV)-induced), Henoch-Schonlein purpura (HSP), hypersensitivity vasculitis, microscopic polyangiitis, Wegener's granulomatosis, or anti-neutrophil cytoplasm antibody associated (ANCA) systemic vasculitis (AASV).

The present disclosure further provides a salt or crystalline form described herein, for use in any of the methods described herein.

The present disclosure further provides use of a crystalline form described herein, or a pharmaceutically acceptable salt thereof, for the preparation of a medicament for use in any of the methods described herein.

As used herein, the term "contacting" refers to the bringing together of indicated moieties in an in vitro system or an in vivo system. For example, "contacting" a PI3K with a salt or crystalline form of the disclosure includes the administration of a crystalline form of the present disclosure to an individual or patient, such as a human, having a PI3K, as well as, for example, introducing a salt or crystalline form of the disclosure into a sample containing a cellular or purified preparation containing the PI3K.

It is believed that the salts and crystalline forms provided herein, or any of the embodiments thereof, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active salt, crystalline form, or pharmaceutical agent that elicits the biological or medicinal response that is being sought in a tissue, system, animal, individual or human by a researcher, veterinarian, medical doctor or other clinician.

As used herein, the term "treating" or "treatment" can refer to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the salts and crystalline forms of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

I. Immune-Checkpoint Therapies

In some embodiments, the PI3Kγ inhibitors provided herein can be used in combination with one or more immune checkpoint inhibitors for the treatment of cancer as described herein. In one embodiment, the combination with one or more immune checkpoint inhibitors as described herein can be used for the treatment of melanoma. Salts and crystalline forms of the present disclosure can be used in combination with one or more immune checkpoint inhibitors. Exemplary immune checkpoint inhibitors include inhibitors against immune checkpoint molecules such as CD20, CD28, CD40, CD122, CD96, CD73, CD47, GITR, CSF1R, JAK, PI3K delta, PI3K gamma, TAM, arginase, HPK1, CD137 (also known as 4-1BB), ICOS, B7-H3, B7-H4, BTLA, CTLA-4, LAG3, TIM3, VISTA, TIGIT, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the salts and crystalline forms of the disclosure provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the PI3Kγ inhibitors provided herein can be used in combination with one or more agonists of immune checkpoint molecules, e.g., OX40, CD27, OX40, GITR, and CD137 (also known as 4-1BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), durvalumab (Imfinzi®), pidilizumab, SHR-1210, PDR001, MGA012, PDR001, AB122, or AMP-224. In some embodiments, the anti-PD-1 monoclonal antibody is nivolumab or pembrolizumab. In some embodiments, the anti-PD1 antibody is pembrolizumab. In some embodiments, the anti-PD-1 monoclonal antibody is MGA012. In some embodiments, the anti-PD1 antibody is SHR-1210. Other anti-cancer agent(s) include antibody therapeutics such as 4-1BB (e.g. urelumab, utomilumab).

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of PD-1 and PD-L1, e.g., an anti-PD-1/PD-L1 monoclonal antibody. In some embodiments, the anti-PD-1/PD-L1 is MCLA-136.

In some embodiments, the inhibitor is MCLA-145.

In some embodiments, the inhibitor of an immune checkpoint molecule is an inhibitor of CTLA-4, e.g., an anti- CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The salts and crystalline forms of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFδ receptor.

In some embodiments, the PI3Kγ inhibitors provided herein can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

As provided throughout, the additional compounds, inhibitors, agents, etc. can be combined with the present compound in a single or continuous dosage form, or they can be administered simultaneously or sequentially as separate dosage forms.

II. Cancer Therapies

Cancer cell growth and survival can be impacted by multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

The salts and crystalline forms of the present disclosure can be used in combination with one or more other enzyme/protein/receptor inhibitors or one or more therapies for the treatment of diseases, such as cancer. Examples of diseases and indications treatable with combination therapies include those as described herein. Examples of cancers include solid tumors and liquid tumors, such as blood cancers.

One or more additional pharmaceutical agents such as, for example, chemotherapeutics, anti-inflammatory agents, steroids, immunosuppressants, immune-oncology agents, metabolic enzyme inhibitors, chemokine receptor inhibitors, and phosphatase inhibitors, as well as targeted therapies such as Bcr-Abl, Flt-3, EGFR, HER2, JAK, c-MET, VEGFR, PDGFR, c-Kit, IGF-1R, RAF and FAK kinase inhibitors such as, for example, those described in WO 2006/056399. Other agents such as therapeutic antibodies can be used in combination with the salts and crystalline forms of the present disclosure for treatment of PI3K-associated diseases, disorders or conditions. The one or more additional pharmaceutical agents can be administered to a patient simultaneously or sequentially.

For example, the salts and crystalline forms as disclosed herein can be combined with one or more inhibitors of the following kinases for the treatment of cancer and other diseases or disorders described herein: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Non-limiting examples of inhibitors that can be combined with the salts and crystalline forms of the present disclosure for treatment of cancer and other diseases and disorders described herein include an FGFR inhibitor (FGFR1, FGFR2, FGFR3 or FGFR4, e.g., INCB54828, INCB62079 and INCB63904), a JAK inhibitor (JAK1 and/or JAK2, e.g., ruxolitinib, baricitinib or INCB39110), an IDO inhibitor (e.g., epacadostat, NLG919, or BMS-986205), an LSD1 inhibitor (e.g., INCB59872 and INCB60003), a TDO inhibitor, a PI3K-delta inhibitor (e.g., INCB50797 and INCB50465), a Pim inhibitor, a CSF1R inhibitor, a TAM receptor tyrosine kinases (Tyro-3, Axl, and Mer), a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643) and an adenosine receptor antagonist or combinations thereof.

In some embodiments, the salts and crystalline forms described herein are administered with a PI3Kδ inhibitor. In some embodiments, the salts and crystalline forms described herein are administered with a JAK inhibitor. In some embodiments, the salts and crystalline forms described herein are administered with a JAK1 or JAK2 inhibitor (e.g., baricitinib or ruxolitinib). In some embodiments, the salts and crystalline forms described herein are administered with a JAK1 inhibitor. In some embodiments, the salts and crystalline forms described herein are administered with a JAK1 inhibitor, which is selective over JAK2.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the salts and crystalline forms of the present disclosure and are presented as a non-limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, IRESSA™ (gefitinib), TARCEVA™ (erlotinib), antibodies to EGFR, intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, leucovirin, ELOXATIN™ (oxaliplatin), pentostatine, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide 17.alpha.-ethinylestradiol, diethylstilbestrol, testosterone, Prednisone, Fluoxymesterone, Dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, avastin, HERCEPTIN™ (trastuzumab), BEXXAR™ (tositumomab), VELCADE™ (bortezomib), ZEVALIN™ (ibritumomab tiuxetan), TRISENOX™ (arsenic trioxide), XELODA™ (capecitabine), vinorelbine, porfimer, ERBITUX™ (cetuximab), thiotepa, altretamine, melphalan, trastuzumab, lerozole, fulvestrant, exemestane, ifosfomide, rituximab, C225 (cetuximab), Campath, (alemtuzumab), clofarabine, cladribine, aphidicolon, rituxan, sunitinib, dasatinib, tezacitabine, Sml 1, fludarabine, pentostatin, triapine, didox, trimidox, amidox, 3-AP, and MDL-101,731.

The salts and crystalline forms of the present disclosure can further be used in combination with other methods of treating cancers, for example by chemotherapy, irradiation therapy, tumortargeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, Toll receptor agonists, STING agonists, oncolytic virotherapy and immunomodulating small molecules, including thalidomide or JAK1/2 inhibitor and the like. The salts and crystalline forms can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, olapariboxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, rucaparib, streptozocin, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, niraparib, veliparib, talazoparib and zoledronate.

Additional examples of chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include imatinib mesylate (GLEEVAC™), nilotinib, dasatinib, bosutinib, and ponatinib, and pharmaceutically acceptable salts. Other example suitable Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include midostaurin, lestaurtinib, linifanib, sunitinib, sunitinib, maleate, sorafenib, quizartinib, crenolanib, pacritinib, tandutinib, PLX3397 and ASP2215, and their pharmaceutically acceptable salts. Other example suitable Flt-3 inhibitors include compounds, and their pharmaceutically acceptable salts, as disclosed in WO 03/037347, WO 03/099771, and WO 04/046120.

Example suitable RAF inhibitors include dabrafenib, sorafenib, and vemurafenib, and their pharmaceutically acceptable salts. Other example suitable RAF inhibitors include compounds, and their pharmaceutically acceptable salts, as disclosed in WO 00/09495 and WO 05/028444.

Example suitable FAK inhibitors include VS-4718, VS-5095, VS-6062, VS-6063, BI853520, and GSK2256098, and their pharmaceutically acceptable salts. Other example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, the salts and crystalline forms of the disclosure can be used in combination with one or more other kinase inhibitors including imatinib, particularly for treating patients resistant to imatinib or other kinase inhibitors.

In some embodiments, the salts and crystalline forms of the disclosure can be used in combination with a chemotherapeutic in the treatment of cancer, and may improve the treatment response as compared to the response to the chemotherapeutic agent alone, without exacerbation of its toxic effects. In some embodiments, the salts and crystalline forms of the disclosure can be used in combination with a chemotherapeutic provided herein. For example, additional pharmaceutical agents used in the treatment of multiple myeloma, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM). Additive or synergistic effects are desirable outcomes of combining a PI3K inhibitor of the present disclosure with an additional agent.

In some embodiments, the salts and crystalline forms of the disclosure can be used in combination with an inhibitor of JAK or PI3Kδ.

The agents can be combined with the present compound in a single or continuous dosage form, or the agents can be administered simultaneously or sequentially as separate dosage forms.

The salts and crystalline forms of the present disclosure can be used in combination with one or more other inhibitors or one or more therapies for the treatment of infections. Examples of infections include viral infections, bacterial infections, fungus infections or parasite infections.

In some embodiments, a corticosteroid such as dexamethasone is administered to a patient in combination with the compounds of the disclosure where the dexamethasone is administered intermittently as opposed to continuously.

The salts and crystalline forms of the present disclosure as described herein can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The salts and crystalline forms of the present disclosure as described herein can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the salts and crystalline forms of the present disclosure can be used in combination with tumor specific antigen such as heat shock proteins isolated from tumor tissue itself. In some embodiments, the salts and crystalline forms can be combined with dendritic cells immunization to activate potent anti-tumor responses.

The salts and crystalline forms of the present disclosure can be used in combination with bispecific macrocyclic peptides that target Fe alpha or Fe gamma receptor-expressing effectors cells to tumor cells. The salts and crystalline forms of the present disclosure can also be combined with macrocyclic peptides that activate host immune responsiveness.

In some further embodiments, combinations of the salts and crystalline forms of the disclosure with other therapeutic agents can be administered to a patient prior to, during, and/or after a bone marrow transplant or stem cell transplant. The salts and crystalline forms of the present disclosure can be used in combination with bone marrow transplant for the treatment of a variety of tumors of hematopoietic origin.

The salts and crystalline forms can be used in combination with vaccines, to stimulate the immune response to pathogens, toxins, and self antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, Giardia, Malaria, Leishmania, Staphylococcus aureus, Pseudomonas Aeruginosa.

Viruses causing infections treatable by methods of the present disclosure include, but are not limit to human papillomavirus, influenza, hepatitis A, B, C or D viruses, adenovirus, poxvirus, herpes simplex viruses, human cytomegalovirus, severe acute respiratory syndrome virus, ebola virus, measles virus, herpes virus (e.g., VZV, HSV-1, HAV-6, HSV-II, and CMV, Epstein Barr virus), flaviviruses, echovirus, rhinovirus, coxsackie virus, cornovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lyme's disease bacteria.

Pathogenic fungi causing infections treatable by methods of the disclosure include, but are not limited to, *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*. Pathogenic parasites causing infections treatable by methods of the disclosure include, but are not limited to, *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compounds (e.g., salts and crystalline forms) of the disclosure can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, the compound of the disclosure or a pharmaceutically acceptable salt thereof, in combination with one or more pharmaceutically acceptable carriers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the disclosure may be milled using known milling procedures such as wet milling to obtain a particle size appropriate for tablet formation and for other formulation types. Finely divided (nanoparticulate) preparations of the compounds of the disclosure can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the disclosure contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the disclosure contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the disclosure contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the disclosure.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the disclosure. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the disclosure can further include one or more additional pharmaceutical agents such as a chemotherapeutic, steroid, anti-inflammatory compound, or immunosuppressant, examples of which are listed herein.

Labeled Compounds and Assay Methods

Another aspect of the present disclosure relates to labeled compounds (e.g., salts and crystalline forms) of the disclosure (radio-labeled, fluorescent-labeled, etc.) that would be useful not only in imaging techniques but also in assays, both in vitro and in vivo, for localizing and quantitating PI3K in tissue samples, including human, and for identifying PI3K ligands by inhibition binding of a labeled compound. Substitution of one or more of the atoms of the compounds of the present disclosure can also be useful in generating differentiated ADME (Adsorption, Distribution, Metabolism and Excretion.) Accordingly, the present disclosure includes PI3K assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}$H (also written as D for deuterium), $^{3}$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, 77Br, $^{123}$I, $^{124}$I, $^{125}$I and $^{131}$I. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as -CD$_3$ being substituted for —CH$_3$). In some embodiments, alkyl groups of the disclosed Formulas and/or Forms can be perdeuterated.

One or more constituent atoms of the compounds presented herein can be replaced or substituted with isotopes of the atoms in natural or non-natural abundance. In some embodiments, the compound includes at least one deuterium atom. For example, one or more hydrogen atoms in a compound presented herein can be replaced or substituted by deuterium (e.g., one or more hydrogen atoms of a $C_{1-6}$ alkyl group can be replaced by deuterium atoms, such as -CD$_3$ being substituted for —CH$_3$). In some embodiments, the compound includes two or more deuterium atoms. In some embodiments, the compound includes 1, 1-2, 1-3, 1-4, 1-5, or 1-6 deuterium atoms. In some embodiments, all of the hydrogen atoms in a compound can be replaced or substituted by deuterium atoms.

In some embodiments, 1, 2, 3, 4, 5, 6, 7, or 8 hydrogen atoms, attached to carbon atoms of any Formula A substituents are each optionally replaced by a deuterium atom.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. J. Med. Chem. 2011, 54, 201-210; R. Xu et. al. J. Label Compd. Radiopharm. 2015, 58, 308-312). In particular, substitution at one or more metabolism sites may afford one or more of the therapeutic advantages.

The radionuclide that is incorporated in the instant radio-labeled compounds will depend on the specific application of that radio-labeled compound. For example, for in vitro PI3K labeling and competition assays, compounds that incorporate $^3H$, $^{14}C$, $^{82}Br$, $^{125}I$, $^{131}I$ or $^{35}S$ can be useful. For radio-imaging applications $^{11}C$, $^{18}F$, $^{125}I$, $^{123}I$, $^{124}I$, $^{131}I$, $^{75}Br$, $^{76}Br$ or $^{77}Br$ can be useful.

It is understood that a "radio-labeled" or "labeled compound" is a compound that has incorporated at least one radionuclide. In some embodiments the radionuclide is selected from the group consisting of $^3H$, $^{14}C$, $^{125}I$, $^{35}S$ and $^{82}Br$.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the disclosure can be used in a screening assay to identify/evaluate compounds. For example, a newly synthesized or identified compound (i.e., test compound) which is labeled can be evaluated for its ability to bind a PI3K by monitoring its concentration variation when contacting with the PI3K, through tracking of the labeling. For example, a test compound (labeled) can be evaluated for its ability to reduce binding of another compound which is known to bind to a PI3K (i.e., standard compound). Accordingly, the ability of a test compound to compete with the standard compound for binding to the PI3K directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, for example, in the treatment or prevention of PI3K-associated diseases or disorders, such as cancer, which include one or more containers containing a pharmaceutical composition comprising a therapeutically effective amount of a salts and crystalline forms of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

The salts and crystalline forms of the Examples have been found to be PI3Kγ inhibitors according to at least one assay described herein.

EXAMPLES

Preparatory LC-MS purifications of some of the compounds prepared were performed on Waters mass directed fractionation systems. The basic equipment setup, protocols, and control software for the operation of these systems have been described in detail in the literature (see e.g., "Two-Pump At Column Dilution Configuration for Preparative LC-MS", K. Blom, J. Combi. Chem., 4, 295 (2002); "Optimizing Preparative LC-MS Configurations and Methods for Parallel Synthesis Purification", K. Blom, R. Sparks, J. Doughty, G. Everlof, T. Hague, A. Combs, J. Combi. Chem., 5, 670 (2003); and "Preparative LC-MS Purification:Improved Compound Specific Method Optimization", K. Blom, B. Glass, R. Sparks, A. Combs, J. Combi. Chem., 6, 874-883 (2004)). The compounds separated were typically subjected to analytical liquid chromatography mass spectrometry (LCMS) for purity analysis under the following conditions: Instrument; Agilent 1100 series, LC/MSD, Column:Waters Sunfire™ $C_{18}$ 5 µm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 µm, 30×100 mm or Waters XBridge™ $C_{18}$ 5 µm, 30×100 mm column, eluting with mobile phase A: 0.1% TFA (trifluoroacetic acid) in water and mobile phase B: acetonitrile; the flow rate was 60 mL/minute, the separating gradient was optimized for each compound using the Compound Specific Method Optimization protocol as described in the literature (see e.g. "Preparative LCMS Purification:Improved Compound Specific Method Optimization", K. Blom, B. Glass, R. Sparks, A. Combs, J. Comb. Chem., 6, 874-883 (2004)).

pH=10 purifications: Waters XBridge™ $C_{18}$ 5 µm, 30×100 mm column, eluting with mobile phase A: 0.1% NH4OH in water and mobile phase B: acetonitrile; the flow rate was 60 mL/minute, the separating gradient was optimized for each compound using the Compound Specific Method Optimization protocol as described in the literature (see e.g. "Preparative LCMS Purification:Improved Compound Specific Method Optimization", K. Blom, B. Glass, R. Sparks, A. Combs, J. Comb. Chem., 6, 874-883 (2004)).

In the below examples, X-Ray Powder Di taction analysis was carried out on a Broker D8 Advance ECO X-ray Powder Diffiactometer (XRPD) instrument with the following parameters: radiation source is Cu at 1.5418 A and LYNX-EYE™ detector and X-ray power of 40 KV, 25 mA. The sample powder was dispersed on a zero-background sample holder. General measurement conditions were: Start Angle—3°; Stop Angle—30°; Sampling—0.015 deg.; and Scan speed—2 deg/min.

Differential Scanning calorimetry (DSC) was carried out on a TA Instrument Differential Scanning calorimetry, Discovery DSC2500 with autosampler. The general experimental conditions were: 20-300° C. at 10° C./min, nitrogen gas flow at 50 mL/min, using an aluminum sample pan.

Example 1

2-(3-(8-Amino-6-(trifluoromethyl)imidazo[1,2-a]pyrazin-3-yl)-4-methylphenyl)-3,3,3-trifluoro-2-hydroxypropanamide

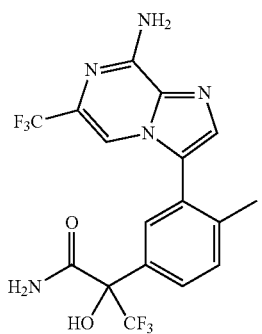 [SMILES: Cc1ccc(C(O)(C(N)=O)C(F)(F)F)cc1-c1cnc2c(N)nc(C(F)(F)F)cn12]

Thermogravimetric analysis (TGA) was carried out on a TA Instrument Thermogravimetric Analyzer, TGA5500 with an autosampler at the following conditions: Ramp at 10° C./min. from 25° C. to 600° C.; nitrogen gas at 25 mL/min balance purge flow; and platinum sample pan.

Step 1. 1-(3-Bromo-4-methylphenyl)-2,2,2-trifluoroethan-1-ol

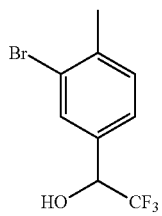

A solution of 3-bromo-4-methylbenzaldehyde (6.51 g, 32.7 mmol) [Aldrich, 565334] in tetrahydrofuran (65.4 mL) was cooled to 0° C. and treated with trimethyl(trifluoromethyl)silane (6.28 mL, 42.5 mmol). The yellow mixture was treated with 1.0 M tetrabutylammonium fluoride in tetrahydrofuran (0.654 mL, 0.654 mmol) at 0° C. and stirred for a few minutes at 0° C. The ice bath was removed and the resulting reaction mixture was stirred for 1.5 h. The reaction mixture was cooled back to 0° C. and treated with water (6.48 mL, 360 mmol) and 1.0 M tetrabutylammonium fluoride in tetrahydrofuran (6.54 mL, 6.54 mmol). The ice bath was removed and the reaction mixture was stirred at ambient temperature for 30 min. The yellow reaction mixture was diluted with brine (150 mL) and extracted with ethyl acetate (200 mL). The organic layer was washed with saturated ammonium chloride (100 mL), dried over sodium sulfate, filtered, and concentrated to give a tan oil. Purification by flash column chromatography using methyl tert-butyl ether (MTBE) in hexanes (0% to 50%) gave the desired product (8.42 g, 95.7%) as a yellow oil. LCMS for $C_9H_7BrF_3$ (M-OH)$^-$: m/z=251.0, 253.0; Found: 250.9, 252.8.

Step 2. 1-(3-Bromo-4-methylphenyl)-2,2,2-trifluoroethan-1-one

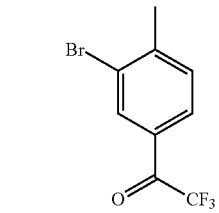

A mixture of 1-(3-bromo-4-methylphenyl)-2,2,2-trifluoroethan-1-ol (8.41 g, 31.3 mmol) in dichloromethane (125 mL) at 0° C. was treated with Dess-Martin periodinane (19.9 g, 46.9 mmol) and stirred at RT for 2.5 h. The reaction mixture was concentrated (by rotary evaporation with the water bath set at 30° C.) to an oily solid that was diluted with diethyl ether (200 mL) which precipitated more solids. This mixture was filtered over Celite® and the Celite® was rinsed with additional diethyl ether (200 mL). The filtrate was washed with saturated sodium bicarbonate solution (3×200 mL) and brine, dried over sodium sulfate, filtered, and concentrated to give an oily solid. The oily solid was partitioned between diethyl ether (150 mL) and water (100 mL). The organic layer was separated and washed with saturated sodium bicarbonate solution (2×75 mL) and brine, dried over sodium sulfate, filtered, and concentrated to give the desired product (7.93 g, 95.0%) as an oil that was used without further purification. LCMS for $C_9H_7BrF_3O$ (M+H)$^-$: m/z=267.0, 269.0; Found: 267.1, 268.9.

Step 3. 2-(3-Bromo-4-methylphenyl)-3,3,3-trifluoro-2-hydroxypropanenitrile

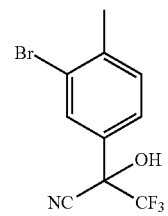

A solution of 1-(3-bromo-4-methylphenyl)-2,2,2-trifluoroethan-1-one (7.92 g, 29.7 mmol) in dichloromethane (29.7 mL) was treated with trimethylsilyl cyanide (8.70 mL, 65.2 mmol), potassium cyanide (0.290 g, 4.45 mmol), and 18-crown-6 (0.290 g, 1.10 mmol) and stirred for 1 h. The reaction was cooled with an ice bath due to an exotherm after the addition of 18-crown-6. The reaction mixture was concentrated (by rotary evaporation with the water bath set at 28° C.) to give a rust colored solid. The solid was dissolved in THF (29.6 mL), cooled to 0° C., treated with 1.8 M HCl (10.9 mL, 19.6 mmol), and stirred at room tempera- Step 4. 2-(3-Bromo-4-methylphenyl)-3,3,3-trifluoro-2-hydroxypropanamide (second eluting enantiomer)

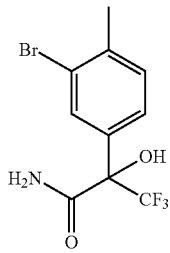

A solution of 2-(3-bromo-4-methylphenyl)-3,3,3-trifluoro-2-hydroxypropanenitrile (8.70 g, 29.6 mmol) in 1,4-dioxane (59.2 mL) at 0° C. was treated with concentrated HCl (9.00 mL, 108 mmol) that had been pre-cooled in an ice bath. While stirring at 0° C., the reaction mixture was bubbled with HCl gas for 45 min. The cooling bath was removed and the reaction mixture was stirred at rt for 61 h. The reaction mixture was bubbled with nitrogen for 10 min to remove some of the HCl, cooled to 0° C., and diluted with brine (200 mL), water (50 mL), and ethyl acetate (200 mL). The organic layer was separated and the aqueous layer was diluted with water (100 mL) to dissolve the remaining solids. The aqueous layer was extracted with ethyl acetate (100 mL). The combined organic extracts were washed with brine, dried over sodium sulfate, filtered, and concentrated to give a brown oil. Purification by flash column chromatography using MTBE in hexanes (0% to 60%) gave the racemic product as a yellow oily solid. The racemic mixture was separated via preparative chiral HPLC (Phenomenex Lux Amylose-1 [21.2×250 mm, 5 micron], eluting with 95% ethanol in hexanes, at flow rate of 18 mL/min, loading about 100 mg in 2 mL ethanol) to give the desired second eluting enantiomer (4.50 g, 48.8%) as a viscous yellow oil. The first enantiomer that eluted had a retention time of 4.0 min. The second enantiomer that eluted had a retention time of 5.3 min.

Second Eluting Enantiomer: $^1$H NMR (400 MHz, DMSO-$d_6$) δ 7.85 (d, J=1.9 Hz, 1H), 7.75 (s, 1H), 7.67 (s, 1H), 7.63-7.53 (m, 2H), 7.41 (d, J=8.1 Hz, 1H), 2.35 (s, 3H). LCMS for $C_{10}H_{10}BrF_3NO_2$ (M+H)$^+$: m/z=312.0, 314.0; Found: 312.0, 314.0.

Step 5. 3,3,3-Trifluoro-2-hydroxy-2-(4-methyl-3-(4,4,5,5-tetramethyl-1,3,2-dioxaborolan-2-yl)phenyl)propanamide

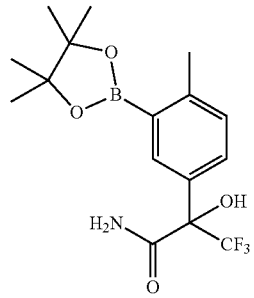 [SMILES: Cc1ccc(C(O)(C(N)=O)C(F)(F)F)cc1B1OC(C)(C)C(C)(C)O1]

A solution of 2-(3-bromo-4-methylphenyl)-3,3,3-trifluoro-2-hydroxypropanamide (3.57 g, 11.5 mmol) (Example 1, Step 4, second eluting enantiomer) in 1,4-dioxane (57.2 mL) was treated with bis(pinacolato)diboron (3.49 g, 13.7 mmol) and potassium acetate (3.71 g, 37.8 mmol) and degassed with nitrogen for 5 min. The reaction mixture was treated with bis(triphenylphosphine)palladium(II)chloride (0.482 g, 0.687 mmol), degassed for 5 min, and stirred at 100° C. for 2.5 h. The reaction mixture was diluted with ethyl acetate (50 mL), filtered over Celite®, and rinsed with additional ethyl acetate (100 mL). The filtrate was washed with brine, dried over sodium sulfate, filtered, and concentrated to a brown foam. Purification by flash column chromatography using MTBE in hexanes (0% to 100%) gave the desired product (3.35 g, 81.5%) as a thick yellow foam. $^1$H NMR (400 MHz, DMSO-$d_6$) δ 7.96 (d, J=2.2 Hz, 1H), 7.63 (dd, J=7.9, 2.1 Hz, 1H), 7.58 (s, 1H), 7.54 (s, 1H), 7.51-7.40 (m, 1H), 7.21 (d, J=8.2 Hz, 1H), 2.46 (s, 3H), 1.30 (s, 12H). LCMS for $C_{16}H_{22}BF_3NO_4$ (M+H)$^+$: m/z=360.2; Found: 360.1.

Step 6. 2-(3-(8-Amino-6-(trifluoromethyl)imidazo[1,2-a]pyrazin-3-yl)-4-methylphenyl)-3,3,3-trifluoro-2-hydroxypropanamide A solution of 3-bromo-6-(trifluoromethyl)imidazo[1,2-a]pyrazin-8-amine (7.50 g, 26.7 mmol) and 3,3,3-trifluoro-2-hydroxy-2-(4-methyl-3-(4,4,5,5-tetramethyl-1,3,2-dioxaborolan-2-yl)phenyl)propanamide (10.5 g, 29.4 mmol) (Example 1, Step 5) in 1,4-dioxane (133 mL) was treated with 1.0 M potassium carbonate in water (53.4 mL, 53.4 mmol), degassed with nitrogen 5 min, treated with dichloro[1,1'-bis(diphenylphosphino)ferrocene]palladium (II) dichloromethane adduct (3.27 g, 4.00 mmol), degassed with nitrogen an additional 5 min, and stirred at 100° C. for 19 h. The reaction mixture was treated with ethyl acetate (200 mL) and brine (50 mL), filtered over Celite and the Celite was rinsed with additional ethyl acetate. The aqueous layer from the filtrate was separated and extracted with ethyl acetate (200 mL). The combined organic extracts were dried over sodium sulfate, filtered, and concentrated to a brown foam. Purification by flash column chromatography using MeOH in dichloromethane (0% to 10%) gave the desired product as a red/brown foam that was not completely pure. This material was repurified by flash column chromatography using MeOH in dichloromethane (0% to 15%) to give the desired product as an orange/brown foam that was still not completely pure. This material was repurified by flash column chromatography using ethyl acetate (containing 5% MeOH) in hexanes (0% to 100%) to give the desired product as a white foam that still contained an impurity. This material was repurified by flash column chromatography using acetonitrile (containing 5% MeOH) in dichloromethane (0% to 100%) to give the desired product (4.67 g, 40.4%) as a white foam. $^1$H NMR (600 MHz, DMSO-$d_6$) δ 7.79 (s, 1H), 7.76-7.71 (m, 2H), 7.71-7.64 (m, 4H), 7.61 (d, J=3.5 Hz, 2H), 7.51 (d, J=8.2 Hz, 1H), 2.23 (s, 3H). LCMS for $C_{17}H_{14}F_6N_5O_2$ (M+H)$^+$: m/z=434.1; Found: 434.1.

Example 2

Preparation and Characterization of 2-(3-(8-Amino-6-(trifluoromethyl)imidazo[1,2-a]pyrazin-3-yl)-4-methylphenyl)-3,3,3-trifluoro-2-hydroxypropanamide, Crystalline Form IA (Free Base)

A vial was charged with 2-(3-(8-amino-6-(trifluoromethyl)imidazo[1,2-a]pyrazin-3-yl)-4-methylphenyl)-3,3,3-trifluoro-2-hydroxypropanamide (0.050 g, 0.115 mmol) and stirred at 80° C. while a 1:2 premixed solution of isopropyl acetate (0.676 mL)/heptane (1.34 mL) was added dropwise. After 2 mL was added the solid was not completely dissolved and some remained on the bottom of the vial. After almost all of the solids had dissolved, new solids were forming on the walls of the vial. More solids had formed after stirring at 80° C. for 2 h. After cooling to ambient temperature the solids were filtered and washed with heptane. The solids were collected and dried under reduced pressure for 30 min to give 2-(3-(8-amino-6-(trifluoromethyl)imidazo[1,2-a]pyrazin-3-yl)-4-methylphenyl)-3,3,3-trifluoro-2-hydroxypropanamide (Form IA) (33.2 mg, 66.4%) as a white solid.

Form IA was confirmed as a crystalline solid according to XRPD analysis. The XRPD pattern of Form IA is shown in FIG. 1 and the peak data is given below in Table 1.

TABLE 1

| XRPD Peak Data for Form IA. ||
| 2-Theta (°) | Relative Intensity (%) |
| --- | --- |
| 8.2 | 0.9 |
| 8.6 | 21.5 |
| 9.5 | 34.3 |
| 10.3 | 92.1 |
| 10.8 | 1.0 |
| 12.8 | 1.1 |
| 13.0 | 5.0 |
| 13.6 | 7.8 |
| 14.2 | 4.1 |
| 14.9 | 100 |
| 16.5 | 2.3 |
| 17.3 | 43.8 |
| 17.8 | 22.6 |
| 18.1 | 1.3 |
| 19.0 | 29.9 |
| 19.2 | 49.7 |
| 19.5 | 8.1 |
| 19.9 | 1.6 |
| 20.1 | 25.4 |
| 20.4 | 15.1 |
| 20.6 | 39.6 |
| 21.2 | 16.8 |
| 21.5 | 6.6 |
| 21.8 | 0.6 |
| 22.2 | 26.6 |
| 22.5 | 4.0 |
| 23.0 | 0.8 |
| 23.6 | 3.2 |

TABLE 1-continued

| XRPD Peak Data for Form IA. ||
| 2-Theta (°) | Relative Intensity (%) |
| --- | --- |
| 24.0 | 42.4 |
| 24.3 | 8.2 |
| 24.6 | 4.2 |
| 25.6 | 7.4 |
| 25.8 | 7.6 |
| 26.3 | 4.3 |
| 26.8 | 12.9 |
| 27.4 | 9.9 |
| 27.9 | 4.4 |
| 28.2 | 1.7 |
| 28.7 | 37.4 |
| 29.6 | 1.3 |

DSC analysis of Form IA revealed one endothermic peak with an onset temperature of 191.9° C. and a maximum at 193.2° C. The DSC thermogram is provided in FIG. 2.

TGA analysis of Form IA revealed significant weight loss above 200° C. due to decomposition of the sample. The TGA thermogram is provided in FIG. 3.

Form IA was confirmed as an anhydrous, non-solvated crystalline form.

Example 3

Preparation and Characterization of 2-(3-(8-Amino-6-(trifluoromethyl)imidazo[1,2-a]pyrazin-3-yl)-4-methylphenyl)-3,3,3-trifluoro-2-hydroxypropanamide, Crystalline Form IIA (Free Base)

Approximately 100 mg of 2-(3-(8-amino-6-(trifluoromethyl)imidazo[1,2-a]pyrazin-3-yl)-4-methylphenyl)-3,3,3-trifluoro-2-hydroxypropanamide free base was dissolved in 1 mL of isopropyl acetate in a 4 mL clear glass vial. To the solution, 2 mL of heptane was added with stirring at ambient temperature. The mixture was heated at 80° C. with stirring for 2 h. The mixture was cooled to ambient temperature and stirred for 1 h. The solid was collected by filtration and air dried to give 2-(3-(8-amino-6-(trifluoromethyl)imidazo[1,2-a]pyrazin-3-yl)-4-methylphenyl)-3,3,3-trifluoro-2-hydroxypropanamide (Form IIA).

Form IIA was confirmed as a crystalline solid according to XRPD analysis. The XRPD pattern of Form IIA is shown in FIG. 4 and the peak data is given below in Table 2.

TABLE 2

| XRPD Peak Data for Form IIA. ||
| 2-Theta (°) | Relative Intensity (%) |
| --- | --- |
| 9.1 | 29.8 |
| 10.0 | 2.2 |
| 11.1 | 38.6 |
| 12.6 | 77.6 |
| 13.5 | 24.8 |
| 14.1 | 5.6 |
| 15.4 | 3.6 |
| 16.1 | 24.0 |
| 16.9 | 41.4 |
| 18.0 | 75.7 |
| 18.4 | 35.0 |
| 19.0 | 77.5 |
| 19.7 | 25.5 |
| 19.9 | 19.5 |
| 20.1 | 40.9 |
| 20.5 | 58.2 |
| 21.0 | 1.1 |

TABLE 2-continued

XRPD Peak Data for Form IIA.

| 2-Theta (°) | Relative Intensity (%) |
|---|---|
| 21.4 | 2.1 |
| 21.6 | 1.3 |
| 21.9 | 100 |
| 23.7 | 29.4 |
| 23.8 | 39.7 |
| 25.1 | 22.5 |
| 25.3 | 33.1 |
| 25.8 | 33.9 |
| 26.3 | 13.6 |
| 26.4 | 3.3 |
| 27.3 | 35.5 |
| 28.3 | 13.2 |
| 29.6 | 15.4 |

DSC analysis of Form IIA revealed one endothermic peak with an onset temperature of 177.2° C. and a maximum at 179.7° C. The DSC thermogram is provided in FIG. 5.

TGA analysis of Form IIA revealed significant weight loss above 200° C. due to decomposition of the sample. The TGA thermogram is provided in FIG. 6.

Form IIA was confirmed as an anhydrous, non-solvated crystalline form.

Example 4

Preparation and Characterization of 2-(3-(8-Amino-6-(trifluoromethyl)imidazo[1,2-a]pyrazin-3-yl)-4-methylphenyl)-3,3,3-trifluoro-2-hydroxypropanamide, Crystalline Form IIIA (Free Base)

Approximately 72 mg of 2-(3-(8-amino-6-(trifluoromethyl)imidazo[1,2-a]pyrazin-3-yl)-4-methylphenyl)-3,3,3-trifluoro-2-hydroxypropanamide free base was dissolved in 1 mL of MeOH in a 4 mL clear glass vial. The solution was evaporated to dryness at ambient temperature. The resultant solid, which is a MeOH solvate, was dried at 60° C. under vacuum overnight to afford 2-(3-(8-amino-6-(trifluoromethyl)imidazo[1,2-a]pyrazin-3-yl)-4-methylphenyl)-3,3,3-trifluoro-2-hydroxypropanamide (Form IIIA).

Form IIIA was confirmed as a crystalline solid according to XRPD analysis. The XRPD pattern of Form IIIA is shown in FIG. 7 and the peak data is given below in Table 3.

TABLE 3

XRPD Peak Data for Form IIIA.

| 2-Theta (°) | Relative Intensity (%) |
|---|---|
| 8.1 | 10.0 |
| 10.6 | 44.4 |
| 12.4 | 5.0 |
| 12.8 | 6.7 |
| 13.5 | 100 |
| 14.2 | 60.9 |
| 15.8 | 3.3 |
| 16.4 | 25.7 |
| 17.1 | 28.3 |
| 17.9 | 29.1 |
| 19.8 | 7.8 |
| 20.3 | 60.6 |
| 20.8 | 15.8 |
| 21.6 | 2.7 |
| 22.3 | 6.5 |
| 22.8 | 10.9 |
| 23.5 | 10.8 |
| 24.1 | 24.6 |
| 24.6 | 15.0 |

TABLE 3-continued

XRPD Peak Data for Form IIIA.

| 2-Theta (°) | Relative Intensity (%) |
|---|---|
| 24.8 | 18.0 |
| 25.2 | 10.0 |
| 25.8 | 10.8 |
| 26.6 | 13.0 |
| 27.5 | 24.0 |
| 28.8 | 6.8 |
| 29.2 | 4.8 |
| 29.8 | 2.1 |

DSC analysis of Form IIIA revealed one endothermic peak with an onset temperature of 134.3° C. and a maximum at 143.0° C. The DSC thermogram is provided in FIG. 8.

TGA analysis of Form IIIA revealed significant weight loss above 200° C. due to decomposition of the sample. The TGA thermogram is provided in FIG. 9.

Form IIIA was confirmed as an anhydrous, non-solvated crystalline form.

Examples 5-6

8-Amino-N-(2-hydroxy-2-methylpropyl)-3-(2-methyl-5-(1,1,1-trifluoro-2-hydroxypropan-2-yl)phenyl)imidazo[1,2-a]pyrazine-6-carboxamide (En-antiomers 1 and 2)

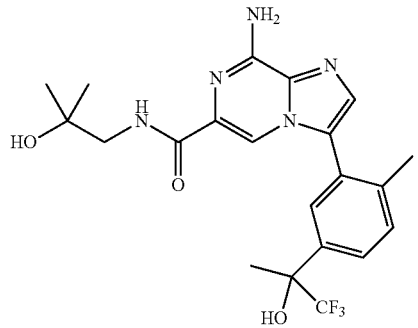 [SMILES: Cc1ccc(C(C)(O)C(F)(F)F)cc1-c1cnc2c(N)nc(C(=O)NCC(C)(C)O)cn12]

Step 1. 6,8-Dibromo-3-iodoimidazo[1,2-a]pyrazine

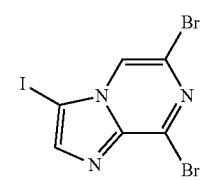 [SMILES: Brc1cn2c(I)cnc2c(Br)n1]

To a solution of 6,8-dibromoimidazo[1,2-a]pyrazine (0.50 g, 1.8 mmol) [Combi-Blocks, OR-7964] in DMF (12 mL) was added N-iodosuccinimide (0.45 g, 2.0 mmol). The reaction mixture was then heated at 60° C. for 15.5 h. The reaction mixture was concentrated in vacuo. The resulting solid was taken up into dichloromethane (DCM). The organic layer was washed sequentially with water and sat. Na$_2$S$_2$O$_3$ (aq). The organic layer was then dried over Na$_2$SO$_4$, filtered, and concentrated to afford the title compound as a light yellow solid (0.64 g, 88%). LCMS for C$_6$H$_3$Br$_2$IN$_3$ (M+H)$^+$: calculated m/z=401.8, 403.8, 405.8; found 401.8, 403.7, 405.6.

Step 2. 6-Bromo-3-iodo-N-(4-methoxybenzyl)imidazo[1,2-a]pyrazin-8-amine

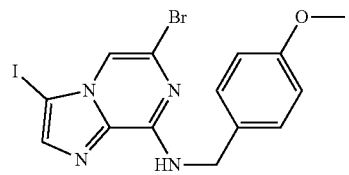 [SMILES: COc1ccc(CNc2nc(Br)cn3c(I)cnc23)cc1]

A solution of 6,8-dibromo-3-iodoimidazo[1,2-a]pyrazine (1.67 g, 3.57 mmol), N,N-diisopropylethylamine (1.24 mL, 7.13 mmol), and (4-methoxyphenyl)methanamine (0.512 mL, 3.92 mmol) in iPrOH (11.9 mL) was heated in a microwave at 110° C. for 1 h. After cooling to room temperature, the solidified reaction mixture was diluted with isopropanol (75 mL) and water (19 mL) and stirred for 10 min. The solids were collected by filtration to give the desired product (1.41 g, 86.1%) that was used without further purification. LCMS for C$_{14}$H$_{13}$BrIN$_4$O (M+H)$^+$: calculated m/z=458.9, 460.9; found 459.0, 461.0.

Step 3. 6-Bromo-3-iodoimidazo[1,2-a]pyrazin-8-amine trifluoroacetate

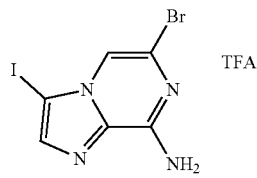

A solution of 6-bromo-3-iodo-N-(4-methoxybenzyl)imidazo[1,2-a]pyrazin-8-amine (2.72 g, 5.92 mmol) in trifluoroacetic acid (TFA, 14.8 mL) was stirred at 55° C. for 5.5 h. The reaction mixture was concentrated and re-concentrated after diluting with acetonitrile (2×). The solid was diluted with ethyl acetate (12 mL) and stirred at room temperature for 1 h. The slurry was diluted with hexanes (12 mL) dropwise and stirred at room temperature for 75 min. The solids were collected by filtration to give the desired product (2.03 g, 75.7%) that was used without further purification. LCMS for C$_6$H$_5$BrIN$_4$ (M+H)$^+$: calculated m/z=338.9, 340.9; found 338.8, 340.8.

Step 4. 2-(3-Bromo-4-methylphenyl)-1,1,1-trifluoropropan-2-ol

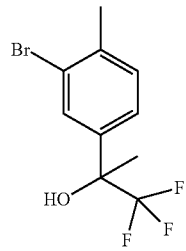

A solution of 1-(3-bromo-4-methylphenyl)ethan-1-one (1.20 g, 5.63 mmol) [Aldrich, 579734] in tetrahydrofuran (22.5 mL) at 0° C. was treated with trimethyl(trifluoromethyl)silane (1.00 mL, 6.76 mmol) [Aldrich, 488712] and stirred at 0° C. for 5 min. The reaction mixture was treated with 1.0 M tetra-n-butylammonium fluoride in tetrahydrofuran (0.282 mL, 0.282 mmol) at 0° C. and stirred at room temperature for 1 h. The reaction mixture was cooled to 0° C., treated with additional 1.0 M tetra-n-butylammonium fluoride in tetrahydrofuran (6.76 mL, 6.76 mmol), and stirred at room temperature for 30 min. The reaction mixture was diluted with ethyl acetate (100 mL) and washed with brine (2×75 mL). The organic layer was separated, dried over sodium sulfate, filtered, and concentrated to give a crude residue. Purification by flash column chromatography using ethyl acetate in hexanes (0%-30%) gave the desired product (1.54 g, 96.7%) as a yellow oil. LCMS for C$_{10}$H$_9$BrF$_3$ (M-OH)$^+$: m/z=265.0, 267.0; Found: 264.9, 267.0.

Step 5. 1,1,1-Trifluoro-2-(4-methyl-3-(4,4,5,5-tetramethyl-1,3,2-dioxaborolan-2-Aphenyl)propan-2-ol

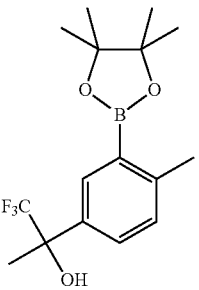 [SMILES: Cc1ccc(C(C)(O)C(F)(F)F)cc1B1OC(C)(C)C(C)(C)O1]

A mixture of 2-(3-bromo-4-methylphenyl)-1,1,1-trifluoropropan-2-ol (0.252 g, 0.890 mmol), bis(pinacolato)diboron (0.294 g, 1.16 mmol) and potassium acetate (0.288 g, 2.94 mmol) in tetrahydrofuran (4.95 mL) was degassed with nitrogen for 5 min. The reaction mixture was treated with triphenylphosphine palladium chloride (0.025 g, 0.036 mmol), degassed with nitrogen for another 5 min, and heated at 135° C. in the microwave for 20 min. The reaction mixture was diluted with ethyl acetate and filtered through a 0.5 micrometer cartridge that was rinsed with ethyl acetate. The filtrate was washed with water and brine, dried over sodium sulfate, filtered, and concentrated to give a crude residue. Purification by flash column chromatography using ether in hexanes (0%-50%) gave the desired product (272 mg, 92.5%) as a colorless oil. LCMS for $C_{16}H_{23}BF_3O_3$ (M+H)$^+$: m/z=331.2; Found: 331.2.

Step 6. 2-(3-(8-Amino-6-bromoimidazo[1,2-a] pyrazin-3-yl)-4-methylphenyl)-1,1,1-trifluoropropan-2-ol

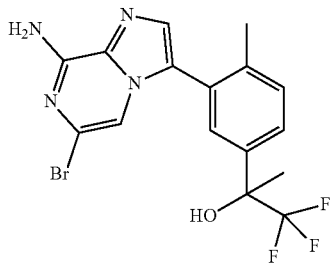 [SMILES: Cc1ccc(C(C)(O)C(F)(F)F)cc1-c1cnc2c(N)nc(Br)cn12]

A mixture of 6-bromo-3-iodoimidazo[1,2-a]pyrazin-8-amine trifluoroacetate (Step 3, 0.855 g, 1.89 mmol), 1,1,1-trifluoro-2-(4-methyl-3-(4,4,5,5-tetramethyl-1,3,2-dioxaborolan-2-yl)phenyl)propan-2-ol (Step 5; 0.623 g, 1.89 mmol), and tetrakis(triphenylphosphine)palladium(0) (0.131 g, 0.113 mmol) in ethanol (12.6 ml) was treated with 2.0 M sodium carbonate in water (1.89 ml, 3.77 mmol), degassed with nitrogen for 5 min, and heated in a microwave reactor at 130° C. for 2 h. The reaction mixture was partially concentrated to remove ethanol and diluted with ethyl acetate and water. The solids were removed with filtration and the aqueous layer of the filtrate was separated and extracted with ethyl acetate (2×). The combined organic layers were washed with brine, dried over magnesium sulfate, filtered, and concentrated to give a crude residue. Purification by flash column chromatography using methanol in dichloromethane (0%-2%) gave the desired product (610 mg, 77.8%) as a white foam. LCMS for $C_{16}H_{15}BrF_3N_4O$ (M+H)$^+$: m/z=415.0, 417.0; Found: 415.0, 417.0.

Step 7. Methyl 8-amino-3-(2-methyl-5-(1,1,1-trifluoro-2-hydroxypropan-2-yl)phenyl)imidazo[1,2-a]pyrazine-6-carboxylate

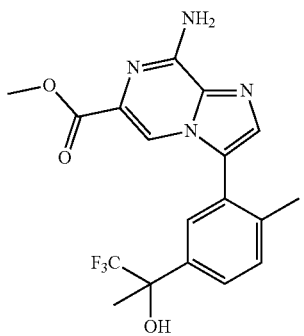

A solution of 2-(3-(8-amino-6-bromoimidazo[1,2-a] pyrazin-3-yl)-4-methylphenyl)-1,1,1-trifluoropropan-2-ol (Step 6; 0.250 g, 0.602 mmol) in methanol (16.1 ml) was treated with triethylamine (0.336 ml, 2.41 mmol), and degassed with nitrogen for 5 min. The reaction mixture was treated with Pd(dppf)$_2$CH$_2$Cl$_2$ (0.049 g, 0.060 mmol), degassed with nitrogen for another 5 min, saturated with CO by bubbling the gas through the reaction subsurface for 3 min, and heated at 60° C. overnight. The reaction mixture was concentrated and the resultant red oil was diluted with ethyl acetate, water, and saturated sodium bicarbonate. The aqueous layer was separated and re-extracted with ethyl acetate (2×). The combined organic layers were washed with brine, dried over magnesium sulfate, filtered, and concentrated to a brown oil. Purification by flash column chromatography using methanol in dichloromethane (0%-4%) gave the desired product (158 mg, 66.5%) as an amber oily solid. LCMS for $C_{18}H_{18}F_3N_4O_3$ (M+H)$^+$: m/z=395.1; Found: 395.1.

Step 8. 8-Amino-N-(2-hydroxy-2-methylpropyl)-3-(2-methyl-5-(1,1,1-trifluoro-2-hydroxypropan-2-yl) phenyl)imidazo[1,2-a]pyrazine-6-carboxamide A solution of methyl 8-amino-3-(2-methyl-5-(1,1,1-trifluoro-2-hydroxypropan-2-yl)phenyl)imidazo[1,2-a]pyrazine-6-carboxylate (Step 7, 0.080 g, 0.203 mmol) in THF (3.38 mL) was treated with 1-amino-2-methylpropan-2-ol (0.181 g, 2.03 mmol) followed by trimethylaluminum (0.507 mL, 1.01 mmol) (2 M in toluene) and stirred at 80° C. overnight. The reaction mixture was treated with additional trimethylaluminum (0.70 ml, 1.40 mmol) (2 M in toluene) and stirred at 80° C. overnight. The reaction mixture was cooled to room temperature, diluted with methanol, and filtered over a pad of Celite®. After rinsing with MeOH (2×), the filtrate was concentrated to an amber oil. Purification via silica gel chromatography (0-5% MeOH/DCM) afforded the title compound as an oily solid (26 mg, 28%) that was a mixture of enantiomers. The racemic mixture was separated via preparative chiral HPLC (Phenomenex Lux Amylose-1 [21.2×250 mm, 5 micron], eluting with 12% ethanol in hexanes, at flow rate of 18 mL/min, loading ~8 mg in 800 μL ethanol). The first peak that eluted had a retention time of 11.9 min (Example 1; Enantiomer 1). The second peak that eluted had a retention time of 16.1 min (Example 2, Enantiomer 2).

Example 5 (Enantiomer 1): $^1$H NMR (400 MHz, DMSO-$d_6$) δ 8.08 (t, J=6.1 Hz, 1H), 7.70 (d, J=2.8 Hz, 2H), 7.65 (d, J=8.1 Hz, 1H), 7.58 (s, 1H), 7.49 (d, J=8.2 Hz, 1H), 7.36 (s, 2H), 6.65 (s, 1H), 4.65 (s, 1H), 3.22 (d, J=6.1 Hz, 2H), 2.15 (s, 3H), 1.70 (s, 3H), 1.09 (s, 6H). LCMS for $C_{21}H_{25}F_3N_5O_3$ (M+H)$^+$: m/z=452.2; Found: 452.1.

Example 6 (Enantiomer 2): $^1$H NMR (600 MHz, DMSO-$d_6$) δ 8.08 (t, J=6.0 Hz, 1H), 7.70 (d, J=3.0 Hz, 2H), 7.65 (d, J=8.2 Hz, 1H), 7.58 (s, 1H), 7.49 (d, J=8.2 Hz, 1H), 7.36 (s, 2H), 6.65 (s, 1H), 4.65 (s, 1H), 3.22 (d, J=6.1 Hz, 2H), 2.15 (s, 3H), 1.70 (s, 3H), 1.09 (s, 6H). LCMS for $C_{21}H_{25}F_3N_5O_3$ (M+H)$^+$: m/z=452.2; Found: 452.2.

Example 7

Preparation and Characterization of 8-Amino-N-(2-hydroxy-2-methylpropyl)-3-(2-methyl-5-(1,1,1-trifluoro-2-hydroxypropan-2-yl)phenypimidazo[1,2-a] pyrazine-6-carboxamide, Crystalline Form IB (Free Base)

A round bottom flask was charged with 8-amino-N-(2-hydroxy-2-methylpropyl)-3-(2-methyl-5-(1,1,1-trifluoro-2-hydroxypropan-2-yl)phenyl)imidazo[1,2-a]pyrazine-6-carboxamide (Enantiomer 2 from Example 6, Step 8; 184 g, 408 mmol) and isopropyl acetate (950 mL). The mixture was stirred at 80° C. for 1 h, cooled to room temperature (RT), and stirred at RT overnight. The solids were collected to give 8-amino-N-(2-hydroxy-2-methylpropyl)-3-(2-methyl-5-(1,1,1-trifluoro-2-hydroxypropan-2-yl)phenyl)imidazo[1,2-a]pyrazine-6-carboxamide (Form IB, 152 g, 82.8%).

Form IB was confirmed as a crystalline solid according to XRPD analysis. The XRPD pattern of Form IB is shown in FIG. 10 and the peak data is given below in Table 4.

TABLE 4

XRPD Peak Data for Form IB.

| 2-Theta (°) | Relative Intensity (%) |
|---|---|
| 6.2 | 31.8 |
| 9.6 | 0.6 |
| 10.4 | 8.8 |
| 11.4 | 12.4 |
| 11.6 | 6.7 |
| 12.0 | 15.6 |
| 12.4 | 4.2 |
| 12.6 | 3.9 |
| 13.9 | 6.0 |
| 14.4 | 10.6 |
| 15.1 | 0.5 |
| 15.6 | 100 |
| 16.0 | 26.8 |
| 16.7 | 49.1 |
| 16.9 | 12.6 |
| 17.4 | 2.9 |
| 18.3 | 9.0 |
| 18.9 | 5.4 |
| 19.3 | 4.3 |
| 19.9 | 19.4 |
| 20.2 | 2.6 |
| 20.7 | 68.4 |
| 21.0 | 4.0 |
| 21.3 | 21.9 |
| 21.9 | 5.2 |
| 22.3 | 10.4 |
| 22.9 | 0.6 |
| 23.2 | 29.4 |
| 23.8 | 0.5 |
| 24.1 | 8.9 |
| 24.4 | 1.3 |
| 24.8 | 1.5 |
| 25.0 | 1.1 |
| 25.5 | 8.2 |
| 26.0 | 2.3 |
| 27.1 | 16.8 |
| 27.3 | 2.2 |
| 28.0 | 7.9 |
| 29.1 | 3.0 |
| 29.7 | 0.4 |

DSC analysis of Form IB revealed one endothermic peak with an onset temperature of 172.2° C. and a maximum at 174.2° C. The DSC thermogram is provided in FIG. 11. Form IB was confirmed as an anhydrous, non-solvated crystalline form.

Example 8

Preparation and Characterization of 8-Amino-N-(2-hydroxy-2-methylpropyl)-3-(2-methyl-5-(1,1,1-trifluoro-2-hydroxypropan-2-yl)phenypimidazo[1,2-a]pyrazine-6-carboxamide, Crystalline Form IIB (Free Base)

A vial was charged with 8-amino-N-(2-hydroxy-2-methylpropyl)-3-(2-methyl-5-(1,1,1-trifluoro-2-hydroxypropan-2-yl)phenyl)imidazo[1,2-a]pyrazine-6-carboxamide (Enantiomer 2 from Example 6, Step 8; 252 mg, 0.559 mmol) and isopropyl acetate (1.25 mL) and the solids slowly dissolved. The mixture was treated with heptane (0.35 mL) until the solids persisted. The mixture was heated at 80° C. for 30 min and stirred at RT overnight. The solids were collected to give 8-amino-N-(2-hydroxy-2-methylpropyl)-3-(2-methyl-5-(1,1,1-trifluoro-2-hydroxypropan-2-yl)phenyl)imidazo[1,2-a]pyrazine-6-carboxamide (Form IIB, 116 mg, 46.0%).

Form IIB was confirmed as a crystalline solid according to XRPD analysis. The XRPD pattern of Form IIB is shown in FIG. 12 and the peak data is given below in Table 5.

TABLE 5

XRPD Peak Data for Form IIB.

| 2-Theta (°) | Relative Intensity (%) |
|---|---|
| 4.3 | 59.1 |
| 6.2 | 0.5 |
| 7.4 | 100 |
| 8.6 | 7.6 |
| 11.3 | 2.1 |
| 13.3 | 34.1 |
| 14.7 | 10.5 |
| 14.9 | 4.1 |
| 15.3 | 58.1 |
| 15.5 | 47.3 |
| 17.0 | 78.5 |
| 17.2 | 41.1 |
| 18.1 | 34.9 |
| 18.8 | 63.6 |
| 19.6 | 15.1 |
| 19.8 | 10.0 |
| 20.1 | 79.7 |
| 20.8 | 0.6 |
| 21.4 | 32.3 |
| 22.4 | 1.5 |
| 22.7 | 6.9 |
| 23.5 | 36.0 |
| 24.1 | 6.8 |
| 25.1 | 6.3 |
| 25.8 | 28.3 |
| 26.2 | 18.0 |
| 26.5 | 13.9 |
| 26.9 | 1.0 |
| 27.3 | 19.5 |
| 27.9 | 14.6 |
| 28.4 | 3.1 |
| 28.6 | 4.0 |
| 29.0 | 3.9 |
| 29.3 | 3.8 |
| 29.6 | 2.4 |

DSC analysis of Form IIB revealed one endothermic peak with an onset temperature of 161.7° C. and a maximum at 165.4° C. The DSC thermogram is provided in FIG. 8. Form IIB was confirmed as an anhydrous, non-solvated crystalline form.

Example 9

8-Amino-N-(2-hydroxy-2-methylpropyl)-3-(2-(methyl-d₃)-5-(1,1,1-trifluoro-2-hydroxypropan-2-yl)phenyl)imidazo[1,2-a]pyrazine-6-carboxamide

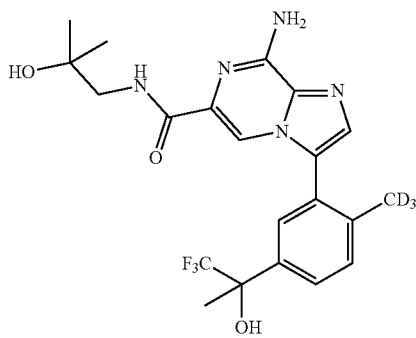 [SMILES: [2H]C([2H])([2H])c1ccc(C(C)(O)C(F)(F)F)cc1-c1cnc2c(N)nc(C(=O)NCC(C)(C)O)cn12]

Step 1. 1-(4-(Methyl-d₃)phenyl)ethan-1-one

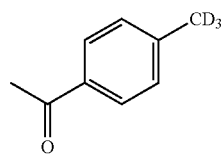

A solution of (4-acetylphenyl)boronic acid (1.00 g, 6.10 mmol) [Aldrich, 470821], bis(di-tert-butyl(4-dimethylaminophenyl)phosphine)dichloropalladium(II) (0.108 g, 0.152 mmol), and cesium fluoride (3.24 g, 21.4 mmol) in DMF (10.2 mL) and water (2.03 mL) was degassed with nitrogen for 10 min, treated with iodomethane-d₃ (1.44 mL, 23.2 mmol), and stirred at 45° C. overnight. The reaction mixture was cooled to rt and diluted with water and ethyl acetate. The aqueous layer was separated and extracted with ethyl acetate (2×). The combined organic extracts were washed with water and brine, dried over magnesium sulfate, filtered, and concentrated (60-70 Torr, 25° C. bath) to give the desired product (546 mg, 65.3%) as a yellow oil that was used without further purification. $^1$H NMR (400 MHz, CDCl₃) δ 7.86 (d, J=8.0 Hz, 2H), 7.26 (d, J=8.0 Hz, 2H), 2.58 (s, 3H). LCMS for C₉H₈D₃O (M+H)⁺: m/z=138.1; Found: 138.1.

Step 2. 1-(3-Bromo-4-(methyl-d₃)phenyl)ethan-1-one

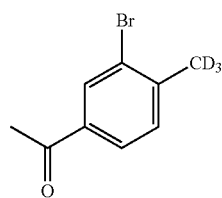

A suspension of aluminum chloride (13.6 g, 102 mmol) in dichloromethane (24 mL) was treated with 1-(4-(methyl-d₃)phenyl)ethan-1-one (6.35 g, 46.3 mmol) dropwise via syringe over 5 min. The residual material in the syringe was rinsed with dichloromethane (7.0 mL) and added to the reaction mixture dropwise. After the initial exotherm the reaction mixture was allowed to cool to rt for 3 min, stirred at 35° C. for 5 min, and treated with bromine (2.38 mL, 46.3 mmol) dropwise over 5 min. The reaction mixture was stirred for 25 min and then added slowly into a mixture of dichloromethane (50 mL), 1 N HCl (100 mL), and ice. The residual reaction mixture was rinsed into the dichloromethane/HCl/ice mixture with additional dichloromethane. The mixture was warmed to room temperature (rt) and the layers were separated. The aqueous layer was extracted with dichloromethane (2×75 mL). The combined organic layers were washed with saturated sodium bicarbonate and brine. The sodium bicarbonate and brine washes contained product and these were combined, acidified with 1M HCl, and extracted with dichloromethane (2×50 mL). The organic layers were all combined, dried over magnesium sulfate, filtered, and concentrated to a yellow oil. Purification by flash column chromatography using ethyl acetate in hexanes (0%-15%) gave the desired product (9.08 g, 90.8%) as a light yellow solid. $^1$H NMR (400 MHz, CDCl₃) δ 8.11 (d, J=1.8 Hz, 1H), 7.79 (dd, J=7.9, 1.8 Hz, 1H), 7.32 (d, J=7.9 Hz, 1H), 2.57 (s, 3H). LCMS for C₉H₇D₃BrO (M+H)⁺: m/z=216.0, 218.0; Found: 216.0, 218.0.

Step 3. 2-(3-Bromo-4-(methyl-d₃)phenyl)-1,1,1-trifluoropropan-2-ol

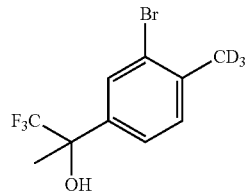 [SMILES: [2H]C([2H])([2H])c1ccc(C(C)(O)C(F)(F)F)cc1Br]

A solution of 1-(3-bromo-4-(methyl-d₃)phenypethan-1-one (9.08 g, 42.0 mmol) in tetrahydrofuran (168 mL) at 0° C. was treated with trimethyl(trifluoromethyl)silane (8.07 mL, 58.8 mmol) [Aldrich, 488712] and stirred at 0° C. for 5 min. The reaction mixture was treated with 1.0 M tetra-n-butylammonium fluoride in tetrahydrofuran (2.10 mL, 2.10 mmol) at 0° C. and stirred at room temperature for 1 h. The reaction mixture was treated with 1.0 M tetra-n-butylammonium fluoride in tetrahydrofuran (12.6 mL, 12.6 mmol) and water (9.8 mL) and stirred at room temperature for 30 min. The reaction mixture was diluted with water (100 mL) and extracted with ethyl acetate (3×50 mL). The combined organic layers were washed with brine, dried over magnesium sulfate, filtered, and concentrated to give a crude residue. Purification by flash column chromatography using ethyl acetate in hexanes (0%-20%) gave the desired product (13.3 g, 111%) as a yellow oil. $^1$H NMR (400 MHz, CDCl₃) δ 7.79-7.72 (m, 1H), 7.48-7.35 (m, 1H), 7.24 (s, 1H), 2.41 (br s, 1H), 1.76 (s, 3H).

Step 4. 1,1,1-Trifluoro-2-(4-(methyl-d₃)-3-(4,4,5,5-tetramethyl-1,3,2-dioxaborolan-2-yl)phenyl)propan-2-ol

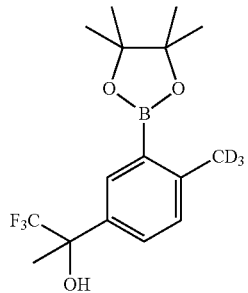 [SMILES: [2H]C([2H])([2H])c1ccc(C(C)(O)C(F)(F)F)cc1B1OC(C)(C)C(C)(C)O1]

A suspension of bis(pinacolato)diboron (12.8 g, 50.2 mmol) and potassium acetate (8.63 ml, 138 mmol) in dioxane (24 mL) was treated with 2-(3-bromo-4-(methyl-d₃)phenyl)-1,1,1-trifluoropropan-2-ol (13.3 g, 41.8 mmol). The residual 2-(3-bromo-4-(methyl-d₃)phenyl)-1,1,1-trifluoropropan-2-ol was rinsed in with dioxane (106 mL) and added to the reaction mixture which was degassed with nitrogen for 10 min. The reaction mixture was treated with bis(triphenylphosphine)palladium(II) dichloride (1.16 g, 1.67 mmol), degassed with nitrogen for another 10 min, and stirred at 100° C. overnight. The reaction mixture was cooled to rt, degassed with nitrogen for 5 min, treated with additional bis(triphenylphosphine)palladium(II) dichloride (1.16 g, 1.67 mmol), degassed with nitrogen for another 5 min, and stirred at 100° C. for 4 h. The reaction mixture was filtered over Celite® and rinsed with THF and ethyl acetate. The filtrate was washed with 1:1 water/brine (300 mL). The aqueous layer was re-extracted with ethyl acetate. The combined organic layers were dried over magnesium sulfate, filtered, and concentrated to a brown oil. Purification by flash column chromatography using MTBE in hexanes (0%-20%) gave the desired product (14.4 g, 84.7%) as a pale yellow oil. ¹H NMR (400 MHz, CDCl₃) δ 7.93 (d, J=2.3 Hz, 1H), 7.55-7.45 (m, 1H), 7.19 (d, J=8.1 Hz, 1H), 2.43 (br s, 1H), 1.77 (s, 3H), 1.34 (s, 12H). LCMS for C₁₆H₂₀D₃BF₃O₃ (M+H)⁺: m/z=334.2; Found: 334.3.

Step 5. 2-(3-(8-Amino-6-bromoimidazo[1,2-a]pyrazin-3-yl)-4-(methyl-d₃)phenyl)-1,1,1-trifluoropropan-2-ol (racemic mixture)

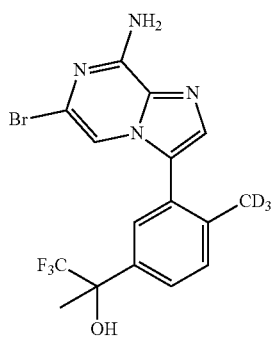 [SMILES: [2H]C([2H])([2H])c1ccc(C(C)(O)C(F)(F)F)cc1-c1cnc2c(N)nc(Br)cn12]

A solution of 1,1,1-trifluoro-2-(4-(methyl-d₃)-3-(4,4,5,5-tetramethyl-1,3,2-dioxaborolan-2-yl)phenyl)propan-2-ol (14.5 g, 35.6 mmol) in dioxane (178 mL) was treated with 6-bromo-3-iodoimidazo[1,2-a]pyrazin-8-amine (12.1 g, 35.6 mmol), degassed with nitrogen for 5 min, treated with dichloro[1,1'-bis(diphenylphosphino)ferrocene]palladium (II) dichloromethane adduct (5.81 g, 7.11 mmol), and degassed with nitrogen for another 5 min. The reaction mixture was treated with 1.0 M potassium carbonate in water (107 ml, 107 mmol), degassed with nitrogen for 5 min, and stirred at 80° C. overnight. The reaction mixture was cooled to rt and filtered over Celite®. The Celite® was rinsed with ethyl acetate and water. The filtrate was diluted with water (150 mL) and extracted with ethyl acetate (3×100 mL). The combined organic layers were dried over magnesium sulfate, filtered, and concentrated to a dark oil. Purification by flash column chromatography using methanol in dichloromethane (0%-5%) and repurification by flash column chromatography using ethyl acetate in hexanes (0%-100%) gave the desired product (13.8 g, 92.8%). LCMS for C₁₆H₁₂D₃BrF₃N₄O (M+H)⁺: m/z=418.1, 420.1; Found: 418.0, 420.0.

Step 6. Second eluting enantiomer of 2-(3-(8-amino-6-bromoimidazo[1,2-a]pyrazin-3-yl)-4-(methyl-d₃)phenyl)-1,1,1-trilluoropropan-2-ol

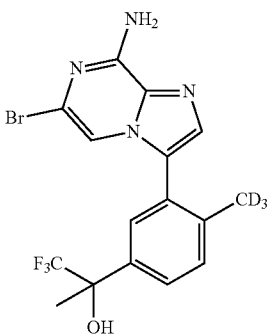 [SMILES: [2H]C([2H])([2H])c1ccc(C(C)(O)C(F)(F)F)cc1-c1cnc2c(N)nc(Br)cn12]

The racemic mixture of 2-(3-(8-amino-6-bromoimidazo[1,2-a]pyrazin-3-yl)-4-(methyl-d₃)phenyl)-1,1,1-trifluoropropan-2-ol was separated via preparative chiral HPLC (Phenomenex Lux Amylose-1 [21.2×250 mm, 5 micron], eluting with 20% ethanol in hexanes, at flow rate of 20 mL/min, loading ~200 mg in 4 mL ethanol). The first peak that eluted had a retention time of 9.6 min. The second peak that eluted had a retention time of 14.6 min.

Peak 2: ¹H NMR (400 MHz, DMSO-d₆) δ 7.66-7.59 (m, 2H), 7.59-7.53 (m, 3H), 7.46 (d, J=8.1 Hz, 1H), 7.25 (s, 1H), 6.66 (s, 1H), 1.71 (s, 3H). LCMS for C₁₆H₁₂D₃BrF₃N₄O (M+H)⁺: m/z=418.1, 420.1; Found: 418.0, 420.0.

Step 7. Methyl 8-amino-3-(2-(methyl-d₃)-5-(1,1,1-trifluoro-2-hydroxypropan-2-yl)phenyl)imidazo[1,2-a]pyrazine-6-carboxylate (single enantiomer prepared)

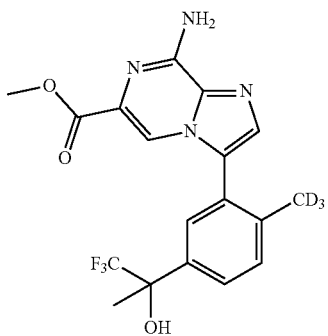 [SMILES: [2H]C([2H])([2H])c1ccc(C(C)(O)C(F)(F)F)cc1-c1cnc2c(N)nc(C(=O)OC)cn12]

A solution of 2-(3-(8-amino-6-bromoimidazo[1,2-a]pyrazin-3-yl)-4-(methyl-d3)phenyl)-1,1,1-trifluoropropan-2-ol (Peak 2 from Step 6, 4.95 g, 48.9 mmol) in methanol (163 mL) and DMF (40.7 mL) was treated with triethylamine (6.81 mL, 48.9 mmol), and degassed with nitrogen for 5 min. The reaction mixture was treated with Pd(dppf)₂CH₂Cl₂ (0.998 g, 1.22 mmol), degassed with nitrogen for another 5 min, saturated with CO by bubbling the gas through the reaction subsurface for 3 min, and heated at 60° C. overnight. The reaction mixture was concentrated and the resultant oil was diluted with ethyl acetate and water. The aqueous layer was separated and re-extracted with ethyl acetate (3×). The combined organic layers were washed with water, saturated ammonium chloride solution, and brine, dried over magnesium sulfate, filtered, and concentrated to a brown oil. Purification by flash column chromatography using methanol in dichloromethane (0%-5%) gave the desired product (4.49 g, 92.4%) as an orange solid. LCMS for $C_{18}H_{15}D_3F_3N_4O_3$ (M+H)⁺: m/z=398.1; Found: 398.3.

Step 8. 8-Amino-3-(2-(methyl-d₃)-5-(1,1,1-trilluoro-2-hydroxypropan-2-yl)phenyl)imidazo[1,2-a]pyrazine-6-carboxylic acid (single enantiomer prepared)

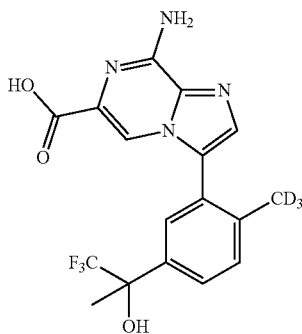 [SMILES: [2H]C([2H])([2H])c1ccc(C(C)(O)C(F)(F)F)cc1-c1cnc2c(N)nc(C(=O)O)cn12]

A solution of methyl 8-amino-3-(2-(methyl-d₃)-5-(1,1,1-trifluoro-2-hydroxypropan-2-yl)phenyl)imidazo[1,2-a]pyrazine-6-carboxylate (4.49 g, 11.3 mmol) (single enantiomer from step 7) in methanol (113 mL) was treated with 1.0 M sodium hydroxide (56.5 mL, 56.5 mmol) and stirred at room temperature. The reaction mixture was concentrated to remove methanol, diluted with water (50 mL), and extracted with ethyl acetate (50 mL, then 20 mL). The combined ethyl acetate layers were extracted with additional 1.0 M sodium hydroxide (3×20 mL). The combined basic aqueous layers were adjusted to pH 5 with citric acid (7.6 g). The aqueous layer was extracted with dichloromethane (2×150 mL). The aqueous layer was diluted with brine and extracted with ethyl acetate (150 mL). The combined organic layers were concentrated to give the desired product (4.06 g, 93.8%) as a tan solid that was used without further purification. ¹H NMR (400 MHz, DMSO-d₆) δ 7.76 (s, 1H), 7.71 (s, 1H), 7.65 (dd, J=8.2, 2.0 Hz, 1H), 7.59 (d, J=2.0 Hz, 1H), 7.49 (d, J=8.1 Hz, 1H), 7.30 (br s, 2H), 6.66 (s, 1H), 1.71 (s, 3H). LCMS for $C_{17}H_{13}D_3F_3N_4O_3$ (M+H)⁺: m/z=384.1; Found: 384.2.

Step 9. 8-Amino-N-(2-hydroxy-2-methylpropyl)-3-(2-(methyl-d₃)-5-(1,1,1-trifluoro-2-hydroxypropan-2-yl)phenyl)imidazo[1,2-a]pyrazine-6-carboxamide A solution of 8-amino-3-(2-(methyl-d₃)-5-(1,1,1-trifluoro-2-hydroxypropan-2-yl)phenyl)imidazo[1,2-a]pyrazine-6-carboxylic acid (4.06 g, 10.6 mmol) (single enantiomer from step 8) in DMF (106 mL) was treated with 1-amino-2-methylpropan-2-ol (1.44 g, 16.2 mmol) [Ark Pharm, AK-37803] and HATU (6.16 g, 16.2 mmol), stirred for 15 min, treated with triethylamine (4.43 mL, 31.8 mmol), and stirred at rt for 3.5 h. The reaction mixture was diluted with water (500 mL) and brine (100 mL) and extracted with ethyl acetate (3×150 mL). The combined organics were washed with saturated ammonium chloride (150 mL), 11% sodium carbonate (150 mL), and brine (100 mL), dried over magnesium sulfate, filtered, and concentrated to an amber oil. Purification by flash column chromatography using methanol in dichloromethane (0%-5%) gave the desired product (4.28 g, 89.0%) as a foam. ¹H NMR (600 MHz, DMSO-d₆) δ 8.14-8.05 (m, 1H), 7.74-7.69 (m, 2H), 7.66 (d, J=7.9 Hz, 1H), 7.62-7.54 (m, 1H), 7.50 (dd, J=8.2, 2.0 Hz, 1H), 7.38 (s, 2H), 6.67 (s, 1H), 4.67 (s, 1H), 3.23 (d, J=5.6 Hz, 2H), 1.71 (s, 3H), 1.10 (s, 6H). LCMS for $C_{21}H_{22}D_3F_3N_5O_3$ (M+H)⁺: m/z=455.2; Found: 455.2.

Example 10

Preparation and Characterization of 8-Amino-N-(2-hydroxy-2-methylpropyl)-3-(2-(methyl-d₃)-5-(1,1,1-trifluoro-2-hydroxypropan-2-yl)phenyl)imidazo[1,2-a]pyrazine-6-carboxamide, Crystalline Form IC (Free Base)

A round bottom was charged with 8-amino-N-(2-hydroxy-2-methylpropyl)-3-(2-(methyl-d₃)-5-(1,1,1-trifluoro-2-hydroxypropan-2-yl)phenyl)imidazo[1,2-a]pyrazine-6-carboxamide (4.60 g, 10.1 mmol) and isopropyl acetate (25.5 mL) that was heated at 80° C. The mixture was stirred at 80° C. and solids began to form within 5 min. The mixture was stirred at 80° C. for 1 h. The heat was discontinued and the mixture was stirred for 1 h while cooling to rt. The mixture was treated with heptane (25.5 mL) dropwise from an addition funnel over 35 min and stirred at rt for 40 min. The solids were collected, washed with 1:1 isopropyl acetate/heptane (10 mL) and dried under reduced pressure at 60° C. for 24 h to give 8-amino-N-(2-hydroxy-2-methylpropyl)-3-(2-(methyl-d₃)-5-(1,1,1-trifluoro-2-hydroxypropan-2-yl)phenyl)imidazo[1,2-a]pyrazine-6-carboxamide (Form I) (4.16 g, 90.4%).

Form IC was confirmed as a crystalline solid according to XRPD analysis. The XRPD pattern of Form IC is shown in FIG. 14 and the peak data is given below in Table 6.

TABLE 6

XRPD Peak Data for Form IC.

| 2-Theta (°) | Relative Intensity (%) |
|---|---|
| 6.2 | 100 |
| 10.4 | 6.4 |
| 11.3 | 6.0 |
| 11.5 | 3.7 |
| 11.9 | 17.3 |
| 12.5 | 10.1 |
| 13.8 | 3.5 |
| 14.4 | 5.5 |
| 15.6 | 51.0 |
| 16.0 | 55.2 |
| 16.7 | 66.3 |
| 16.9 | 7.5 |
| 17.4 | 2.9 |
| 18.3 | 8.6 |
| 18.8 | 17.1 |
| 19.2 | 1.4 |
| 19.9 | 20.4 |
| 20.2 | 1.4 |
| 20.7 | 24.4 |
| 21.0 | 4.1 |
| 21.2 | 47.0 |
| 21.8 | 3.7 |
| 22.3 | 16.6 |
| 23.2 | 17.0 |
| 24.1 | 12.4 |
| 24.4 | 1.9 |
| 24.8 | 1.7 |
| 24.9 | 0.9 |
| 25.3 | 0.8 |
| 25.5 | 3.9 |
| 25.9 | 1.5 |
| 27.0 | 14.7 |
| 27.3 | 3.4 |
| 27.9 | 5.8 |
| 29.1 | 1.4 |
| 29.7 | 1.2 |

DSC analysis of Form IC revealed one endothermic peak with an onset temperature of 173.4° C. and a maximum at 179.0° C. The DSC thermogram is provided in FIG. 15. Form IC was confirmed as an anhydrous, non-solvated crystalline form.

Example 11

2-(3-(8-Amino-6-(trifluoromethyl)imidazo[1,2-a] pyrazin-3-yl)-4-methylphenyl)-3,3,3-trifluoro-2-hydroxypropanamide hydrobromic acid (HBr) salt 2-(3-(8-amino-6-(trifluoromethyl)imidazo[1,2-a]pyrazin-3-yl)-4-methylphenyl)-3,3,3-trifluoro-2-hydroxypropanamide free base (98.81 mg) was dissolved in 2.5 mL of methanol in a 4 mL clear glass vial. To the solution, 42.4 μL of 6M aqueous HBr solution (1.2 eq.) was added and mixed well. The solution was evaporated at room temperature to obtain HBr salt crystal.

Example 12

Characterization of Single Crystal 2-(3-(8-Amino-6-(trifluoromethyl)imidazo[1,2-a]pyrazin-3-yl)-4-methylphenyl)-3,3,3-trifluoro-2-hydroxypropanamide hydrobromic acid (HBr) salt Crystal Data: C35H32 Br2 F12 N10 O5, from methanol, colorless, irregular plate, 0.450×0.210×0.060 mm, monoclinic, C2, a=20.055(7) Å, b=10.115(4) Å, c=21.363(8) Å, beta=94.953(7), Vol=4318(3) Å$^3$, Z=4, T=−40° C., Formula weight=1060.52, Density=1.631 g/cm$^3$, μ(Mo)=1.98 mm$^{-1}$.

Data Collection: Data collection was performed using a Bruker SMART APEX-II CCD system, MoKalpha radiation, standard focus tube, anode power=50 kV×30 mA, crystal to plate distance=5.0 cm, 512×512 pixels/frame, beam center=(259.19,253.13), total frames=2635, oscillation/frame=0.50°, exposure/frame=40.1 sec/frame, SAINT integration, hkl min/max=(−26,26,−12,13,−27,27), data input to shelx=38968, unique data=9756, two-theta range=4.51 to 55.43°, completeness to two-theta 55.43=99.60%, R(int-xl)=0.0672, SADABS correction applied.

Solution And Refinement: The crystal structure was solved using XS(Shelxtl) and refined using shelxtl software package. Refinement was by full-matrix least squares on F$^2$, scattering factors from Int. Tab. Vol C Tables 4.2.6.8 and 6.1.1.4, number of data=9756, number of restraints=1, number of parameters=584, data/parameter ratio=16.71, goodness-of-fit on F2=1.14, R indices [I>4sigma(I)] R1=0.0648, wR2=0.1560, R indices (all data) R1=0.1004, wR2=0.1719, max difference peak and hole=1.795 and −0.642 e/Å$^3$, refined flack parameter=0.038(6). All of the hydrogen atoms were idealized using a riding model. Table 7 shows atomic coordinates (×10$^4$) and equivalent isotropic displacement parameters (Å$^2$×10$^3$). U(eq) is defined as one third of the trace of the orthogonalized Uij tensor. Table 8 shows bond lengths [Å] and angles [deg]. Table 9 shows anisotropic displacement parameters (Å$^2$×10$^3$).

Figure 16A:
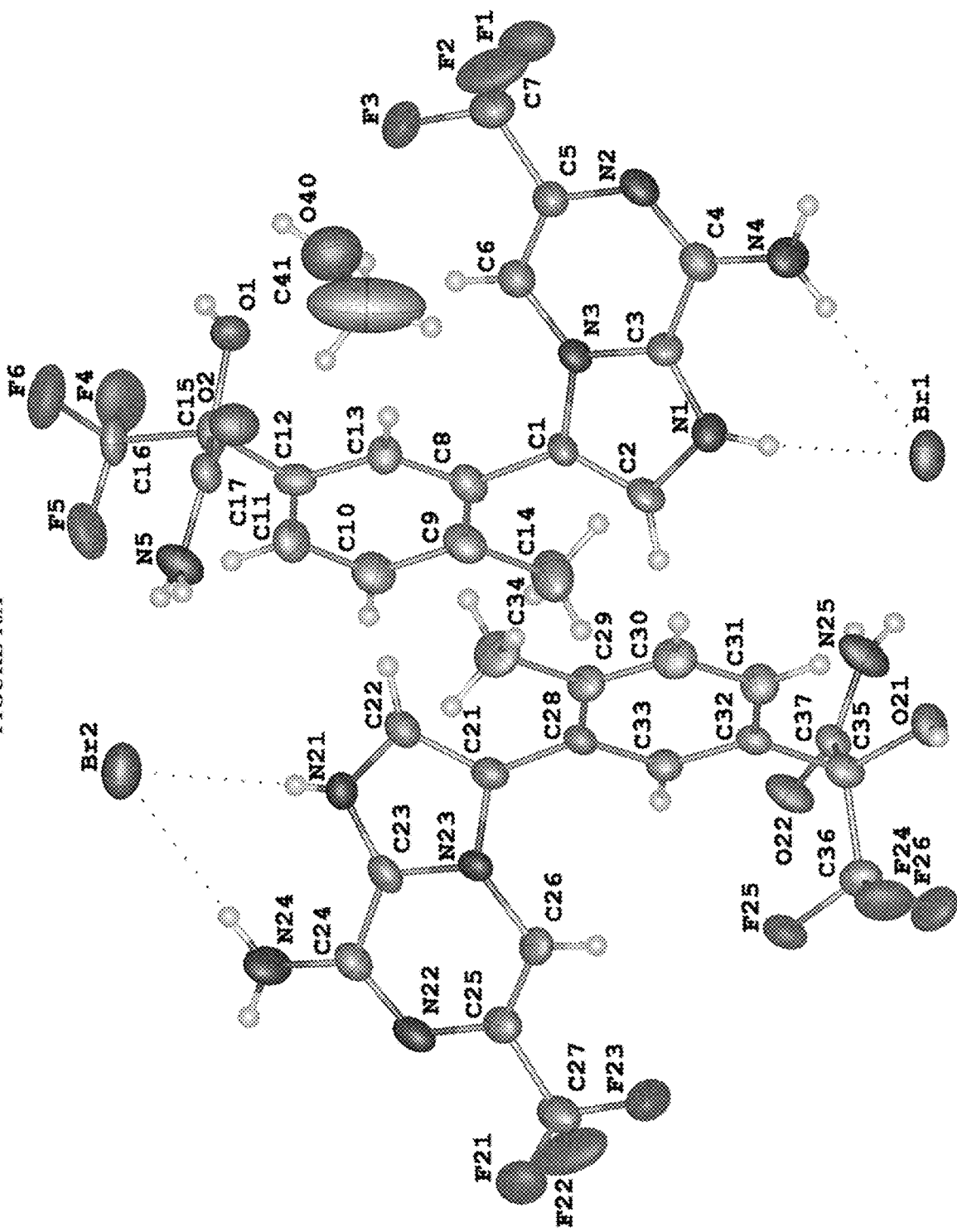
FIG. 16A shows the asymmetric crystalline unit of 2-(3-(8-amino-6-(trifluoromethyl)imidazo[1,2-a]pyrazin-3-yl)-4-methylphenyl)-3,3,3-trifluoro-2-hydroxypropanamide hydrobromic acid salt, methanol solvate form, with thermal ellipsoids drawn to the 30% probability level.
Figure 16B:
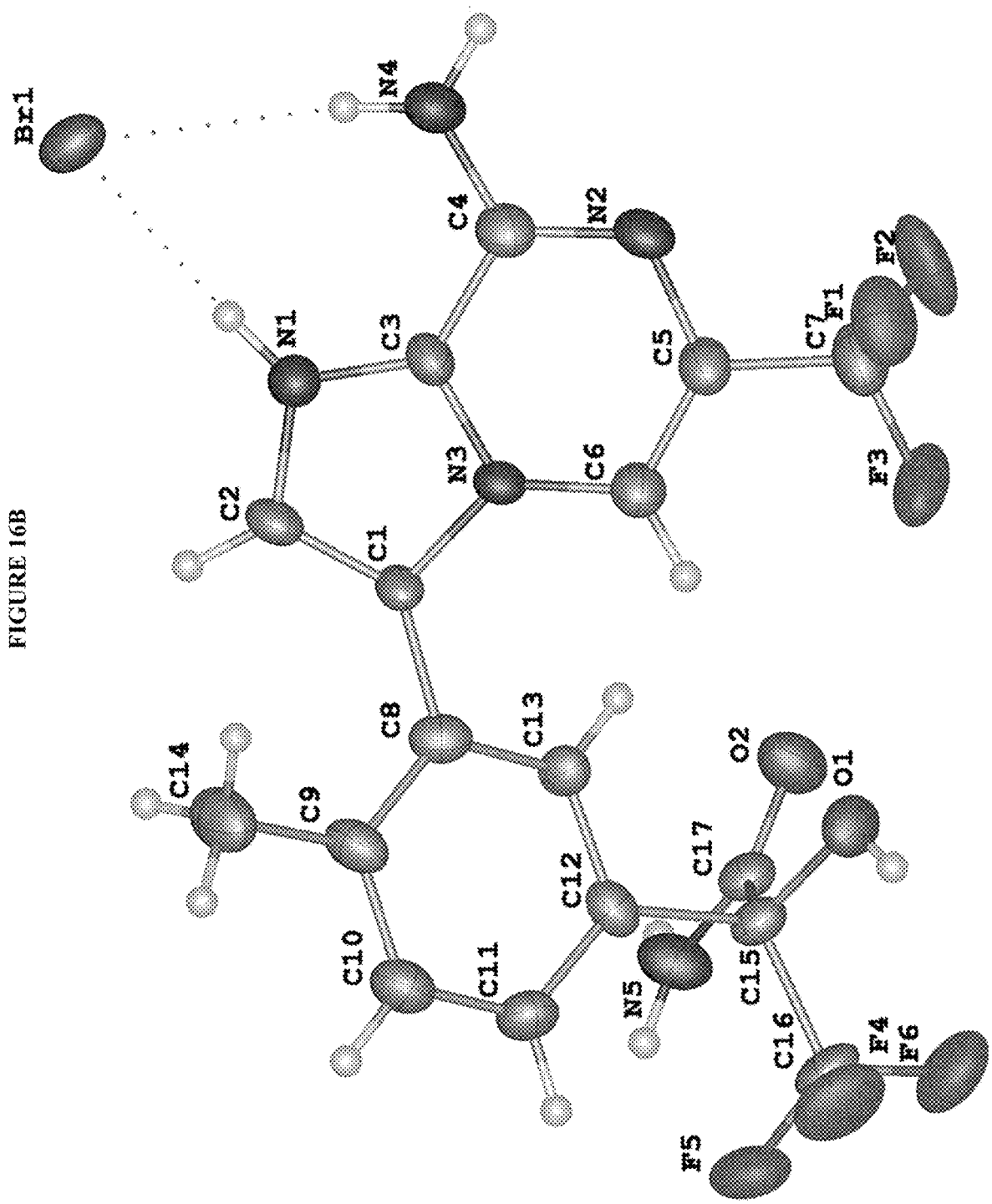
FIG. 16B shows a crystalline unit of 2-(3-(8-amino-6-(trifluoromethyl)imidazo[1,2-a]pyrazin-3-yl)-4-methylphenyl)-3,3,3-trifluoro-2-hydroxypropanamide hydrobromic acid salt, with thermal ellipsoids drawn to the 30% probability level.

Results: This analysis confirmed the structure of 2-(3-(8-amino-6-(trifluoromethyl)imidazo[1,2-a]pyrazin-3-yl)-4-methylphenyl)-3,3,3-trifluoro-2-hydroxypropanamide hydrobromic acid salt. The asymmetric unit contains two molecules of 2-(3-(8-amino-6-(trifluoromethyl)imidazo[1,2-a]pyrazin-3-yl)-4-methylphenyl)-3,3,3-trifluoro-2-hydroxypropanamide, two bromides to balance the charge, and one methanol solvent molecule, as shown in FIGS. 16A-16B. The enantiomeric setting was based on the Flack parameter that refined to 0.038(6). This study determined the absolute configuration at the chiral centers C15=S- and C35=S-.

TABLE 7

| | x | y | z | U(eq) |
|---|---|---|---|---|
| Br(1) | 5582(1) | 9450(1) | 4009(1) | 42(1) |
| Br(2) | 5862(1) | 10538(1) | 1429(1) | 55(1) |
| F(1) | 6628(3) | 14263(6) | 1224(3) | 55(2) |
| F(2) | 6580(3) | 15776(7) | 1906(3) | 69(2) |
| F(3) | 5777(3) | 15548(8) | 1169(3) | 76(2) |
| F(4) | 2936(3) | 16054(7) | 74(2) | 64(2) |
| F(5) | 2172(3) | 16617(6) | 663(3) | 53(2) |
| F(6) | 2941(3) | 17995(6) | 485(3) | 64(2) |
| F(21) | −154(3) | 10814(6) | 4245(3) | 56(2) |
| F(22) | −36(4) | 9202(6) | 3634(4) | 77(2) |
| F(23) | 718(3) | 9617(6) | 4368(4) | 95(3) |
| F(24) | 2863(3) | 8853(7) | 5238(2) | 50(2) |
| F(25) | 2167(2) | 8776(5) | 4410(3) | 42(1) |
| F(26) | 2742(3) | 7056(5) | 4708(3) | 49(1) |
| O(1) | 3939(3) | 16429(6) | 1010(3) | 37(1) |
| O(2) | 3666(3) | 17493(7) | 2068(3) | 43(2) |
| O(21) | 3946(3) | 8374(6) | 4603(3) | 32(1) |
| O(22) | 2767(3) | 7895(7) | 3331(3) | 36(2) |
| O(40) | 4500(4) | 14342(10) | 397(4) | 75(2) |
| N(1) | 4949(3) | 11437(8) | 3026(3) | 36(2) |
| N(2) | 6280(3) | 13465(8) | 2462(3) | 36(2) |
| N(3) | 4935(3) | 12867(7) | 2259(3) | 28(2) |
| N(4) | 6392(4) | 11972(9) | 3289(3) | 45(2) |
| N(5) | 2564(4) | 17096(8) | 1956(4) | 39(2) |

TABLE 7-continued

|      | x        | y         | z        | U(eq)   |
|------|----------|-----------|----------|---------|
| N(21) | 1533(4) | 13615(8) | 2454(4) | 33(2) |
| N(22) | 219(3) | 11535(8) | 3008(4) | 39(2) |
| N(23) | 1563(3) | 12205(7) | 3219(3) | 31(2) |
| N(24) | 98(4) | 12981(9) | 2172(4) | 50(2) |
| N(25) | 3891(3) | 7901(8) | 3415(3) | 39(2) |
| C(1) | 4279(4) | 12394(8) | 2289(4) | 28(2) |
| C(2) | 4303(4) | 11526(9) | 2766(4) | 32(2) |
| C(3) | 5320(4) | 12256(9) | 2717(4) | 31(2) |
| C(4) | 6017(4) | 12567(10) | 2820(4) | 35(2) |
| C(5) | 5853(4) | 13980(9) | 1980(4) | 33(2) |
| C(6) | 5199(4) | 13700(9) | 1858(4) | 34(2) |
| C(7) | 6210(5) | 14906(11) | 1569(5) | 49(3) |
| C(8) | 3706(4) | 12918(9) | 1867(4) | 31(2) |
| C(9) | 3210(4) | 12062(10) | 1606(4) | 35(2) |
| C(10) | 2685(4) | 12628(10) | 1211(4) | 39(2) |
| C(11) | 2677(4) | 13941(10) | 1064(4) | 34(2) |
| C(12) | 3181(4) | 14780(9) | 1310(4) | 29(2) |
| C(13) | 3678(4) | 14244(8) | 1725(3) | 26(2) |
| C(14) | 3214(5) | 10601(11) | 1716(6) | 54(3) |
| C(15) | 3278(4) | 16231(9) | 1162(4) | 28(2) |
| C(16) | 2819(5) | 16748(10) | 589(4) | 36(2) |
| C(17) | 3181(4) | 17041(9) | 1765(4) | 29(2) |
| C(21) | 2216(4) | 12663(9) | 3209(4) | 31(2) |
| C(22) | 2176(4) | 13579(10) | 2730(4) | 36(2) |
| C(23) | 1158(4) | 12776(9) | 2745(4) | 32(2) |
| C(24) | 462(4) | 12442(10) | 2644(4) | 34(2) |
| C(25) | 628(4) | 11023(9) | 3491(4) | 35(2) |
| C(26) | 1280(4) | 11327(8) | 3631(4) | 33(2) |
| C(27) | 287(4) | 10187(10) | 3932(5) | 42(2) |
| C(28) | 2774(4) | 12198(8) | 3629(4) | 27(2) |
| C(29) | 3264(4) | 13027(8) | 3916(4) | 30(2) |
| C(30) | 3753(5) | 12484(9) | 4315(4) | 35(2) |
| C(31) | 3802(4) | 11136(9) | 4439(4) | 32(2) |
| C(32) | 3317(4) | 10301(8) | 4149(4) | 22(2) |
| C(33) | 2819(4) | 10830(8) | 3738(4) | 26(2) |
| C(34) | 3239(5) | 14511(10) | 3811(5) | 45(2) |
| C(35) | 3344(4) | 8814(9) | 4276(4) | 29(2) |
| C(36) | 2773(4) | 8377(9) | 4650(4) | 34(2) |
| C(37) | 3309(4) | 8112(9) | 3631(4) | 27(2) |
| C(41) | 4168(10) | 13090(30) | 222(9) | 147(10) |

TABLE 8

| F(1)—C(7) | 1.332(12) |
|---|---|
| F(2)—C(7) | 1.323(12) |
| F(3)—C(7) | 1.334(12) |
| F(4)—C(16) | 1.343(11) |
| F(5)—C(16) | 1.327(11) |
| F(6)—C(16) | 1.307(11) |
| F(21)—C(27) | 1.315(11) |
| F(22)—C(27) | 1.322(12) |
| F(23)—C(27) | 1.345(12) |
| F(24)—C(36) | 1.342(10) |
| F(25)—C(36) | 1.341(10) |
| F(26)—C(36) | 1.344(10) |
| O(1)—C(15) | 1.405(10) |
| O(2)—C(17) | 1.211(10) |
| O(21)—C(35) | 1.414(10) |
| O(22)—C(37) | 1.232(9) |
| O(40)—C(41) | 1.46(2) |
| N(1)—C(3) | 1.327(11) |
| N(1)—C(2) | 1.368(10) |
| N(2)—C(4) | 1.326(12) |
| N(2)—C(5) | 1.382(11) |
| N(3)—C(6) | 1.343(11) |
| N(3)—C(3) | 1.342(11) |
| N(3)—C(1) | 1.407(10) |
| N(4)—C(4) | 1.341(11) |
| N(5)—C(17) | 1.338(11) |
| N(21)—C(23) | 1.323(12) |
| N(21)—C(22) | 1.372(11) |
| N(22)—C(24) | 1.323(12) |
| N(22)—C(25) | 1.364(12) |
| N(23)—C(23) | 1.369(11) |
| N(23)—C(21) | 1.392(10) |
| N(23)—C(26) | 1.404(11) |
| N(24)—C(24) | 1.311(11) |
| N(25)—C(37) | 1.310(10) |
| C(1)—C(2) | 1.344(12) |
| C(1)—C(8) | 1.494(11) |
| C(3)—C(4) | 1.432(12) |
| C(5)—C(6) | 1.345(12) |
| C(5)—C(7) | 1.506(13) |
| C(8)—C(13) | 1.376(12) |
| C(8)—C(9) | 1.399(12) |
| C(9)—C(10) | 1.413(13) |
| C(9)—C(14) | 1.497(15) |
| C(10)—C(11) | 1.365(14) |
| C(11)—C(12) | 1.388(12) |
| C(12)—C(13) | 1.386(11) |
| C(12)—C(15) | 1.518(12) |
| C(15)—C(17) | 1.552(12) |
| C(15)—C(16) | 1.556(11) |
| C(21)—C(22) | 1.377(12) |
| C(21)—C(28) | 1.450(11) |
| C(23)—C(24) | 1.435(12) |
| C(25)—C(26) | 1.351(12) |
| C(25)—C(27) | 1.478(13) |
| C(28)—C(29) | 1.394(12) |
| C(28)—C(33) | 1.404(12) |
| C(29)—C(30) | 1.359(12) |
| C(29)—C(34) | 1.517(13) |
| C(30)—C(31) | 1.391(13) |
| C(31)—C(32) | 1.393(11) |
| C(32)—C(33) | 1.380(11) |
| C(32)—C(35) | 1.529(12) |
| C(35)—C(36) | 1.518(11) |
| C(35)—C(37) | 1.546(11) |
| C(3)—N(1)—C(2) | 107.9(7) |
| C(4)—N(2)—C(5) | 115.9(7) |
| C(6)—N(3)—C(3) | 121.4(7) |
| C(6)—N(3)—C(1) | 131.5(7) |
| C(3)—N(3)—C(1) | 107.0(7) |
| C(23)—N(21)—C(22) | 109.4(8) |
| C(24)—N(22)—C(25) | 118.7(7) |
| C(23)—N(23)—C(21) | 110.3(7) |
| C(23)—N(23)—C(26) | 119.0(7) |
| C(21)—N(23)—C(26) | 130.7(7) |
| C(2)—C(1)—N(3) | 106.5(7) |
| C(2)—C(1)—C(8) | 131.6(7) |
| N(3)—C(1)—C(8) | 121.8(7) |
| C(1)—C(2)—N(1) | 108.8(7) |
| N(1)—C(3)—N(3) | 109.8(7) |
| N(1)—C(3)—C(4) | 129.9(8) |
| N(3)—C(3)—C(4) | 120.2(8) |
| N(2)—C(4)—N(4) | 120.9(8) |
| N(2)—C(4)—C(3) | 119.5(8) |
| N(4)—C(4)—C(3) | 119.6(8) |
| C(6)—C(5)—N(2) | 126.5(8) |
| C(6)—C(5)—C(7) | 121.6(8) |
| N(2)—C(5)—C(7) | 111.9(8) |
| N(3)—C(6)—C(5) | 116.1(8) |
| F(2)—C(7)—F(1) | 106.0(8) |
| F(2)—C(7)—F(3) | 109.1(9) |
| F(1)—C(7)—F(3) | 106.8(9) |
| F(2)—C(7)—C(5) | 111.7(9) |
| F(1)—C(7)—C(5) | 111.8(9) |
| F(3)—C(7)—C(5) | 111.1(8) |
| C(13)—C(8)—C(9) | 120.0(8) |
| C(13)—C(8)—C(1) | 119.6(7) |
| C(9)—C(8)—C(1) | 120.3(8) |
| C(8)—C(9)—C(10) | 117.1(9) |
| C(8)—C(9)—C(14) | 123.6(8) |
| C(10)—C(9)—C(14) | 119.2(8) |
| C(11)—C(10)—C(9) | 121.7(9) |
| C(10)—C(11)—C(12) | 121.0(8) |
| C(13)—C(12)—C(11) | 117.6(8) |
| C(13)—C(12)—C(15) | 114.4(7) |
| C(11)—C(12)—C(15) | 128.0(8) |
| C(8)—C(13)—C(12) | 122.5(7) |
| O(1)—C(15)—C(12) | 109.1(7) |
| O(1)—C(15)—C(17) | 107.7(7) |
| C(12)—C(15)—C(17) | 108.1(7) |
| O(1)—C(15)—C(16) | 106.0(7) |
| C(12)—C(15)—C(16) | 114.2(7) |

TABLE 8-continued

| | |
|---|---|
| C(17)—C(15)—C(16) | 111.5(7) |
| F(6)—C(16)—F(5) | 108.3(7) |
| F(6)—C(16)—F(4) | 108.5(8) |
| F(5)—C(16)—F(4) | 106.6(8) |
| F(6)—C(16)—C(15) | 110.6(8) |
| F(5)—C(16)—C(15) | 113.0(7) |
| F(4)—C(16)—C(15) | 109.7(7) |
| O(2)—C(17)—N(5) | 122.8(8) |
| O(2)—C(17)—C(15) | 119.4(8) |
| N(5)—C(17)—C(15) | 117.5(8) |
| C(22)—C(21)—N(23) | 103.9(7) |
| C(22)—C(21)—C(28) | 132.1(8) |
| N(23)—C(21)—C(28) | 124.0(7) |
| N(21)—C(22)—C(21) | 109.2(8) |
| N(21)—C(23)—N(23) | 107.0(7) |
| N(21)—C(23)—C(24) | 131.7(8) |
| N(23)—C(23)—C(24) | 121.3(8) |
| N(24)—C(24)—N(22) | 122.1(8) |
| N(24)—C(24)—C(23) | 119.2(9) |
| N(22)—C(24)—C(23) | 118.5(8) |
| C(26)—C(25)—N(22) | 126.0(8) |
| C(26)—C(25)—C(27) | 118.9(9) |
| N(22)—C(25)—C(27) | 114.7(8) |
| C(25)—C(26)—N(23) | 116.2(8) |
| F(21)—C(27)—F(22) | 106.7(7) |
| F(21)—C(27)—F(23) | 106.0(9) |
| F(22)—C(27)—F(23) | 105.7(9) |
| F(21)—C(27)—C(25) | 114.6(8) |
| F(22)—C(27)—C(25) | 111.0(9) |
| F(23)—C(27)—C(25) | 112.4(7) |
| C(29)—C(28)—C(33) | 119.1(7) |
| C(29)—C(28)—C(21) | 123.6(8) |
| C(33)—C(28)—C(21) | 117.3(7) |
| C(30)—C(29)—C(28) | 118.4(8) |
| C(30)—C(29)—C(34) | 120.3(8) |
| C(28)—C(29)—C(34) | 121.2(8) |
| C(29)—C(30)—C(31) | 123.5(8) |
| C(30)—C(31)—C(32) | 118.3(8) |
| C(33)—C(32)—C(31) | 119.2(8) |
| C(33)—C(32)—C(35) | 120.5(7) |
| C(31)—C(32)—C(35) | 120.3(7) |
| C(32)—C(33)—C(28) | 121.4(8) |
| O(21)—C(35)—C(36) | 107.4(7) |
| O(21)—C(35)—C(32) | 114.4(7) |
| C(36)—C(35)—C(32) | 111.2(7) |
| O(21)—C(35)—C(37) | 105.6(7) |
| C(36)—C(35)—C(37) | 110.9(7) |
| C(32)—C(35)—C(37) | 107.3(7) |
| F(25)—C(36)—F(24) | 107.1(7) |
| F(25)—C(36)—F(26) | 106.6(7) |
| F(24)—C(36)—F(26) | 105.9(7) |
| F(25)—C(36)—C(35) | 114.3(7) |
| F(24)—C(36)—C(35) | 110.1(7) |
| F(26)—C(36)—C(35) | 112.4(7) |
| O(22)—C(37)—N(25) | 124.1(7) |
| O(22)—C(37)—C(35) | 121.1(7) |
| N(25)—C(37)—C(35) | 114.5(7) |

TABLE 9

| | U11 | U22 | U33 | U23 | U13 | U12 |
|---|---|---|---|---|---|---|
| Br(1) | 47(1) | 38(1) | 38(1) | 8(1) | −8(1) | 5(1) |
| Br(2) | 62(1) | 48(1) | 52(1) | 12(1) | −1(1) | 10(1) |
| F(1) | 56(4) | 48(4) | 66(4) | −1(3) | 28(3) | −3(3) |
| F(2) | 77(4) | 53(4) | 79(4) | −12(4) | 25(3) | −43(4) |
| F(3) | 50(4) | 68(5) | 110(5) | 59(5) | 15(4) | 8(4) |
| F(4) | 82(5) | 80(5) | 29(3) | 2(3) | −6(3) | 13(4) |
| F(5) | 42(3) | 56(4) | 58(3) | 8(3) | −17(3) | 10(3) |
| F(6) | 84(5) | 43(3) | 62(4) | 21(3) | −6(3) | 10(3) |
| F(21) | 53(4) | 53(4) | 68(4) | 8(3) | 28(3) | 10(3) |
| F(22) | 95(5) | 38(4) | 107(5) | −13(4) | 52(4) | −32(4) |
| F(23) | 43(4) | 103(7) | 143(7) | 85(6) | 21(4) | 6(4) |
| F(24) | 46(3) | 68(4) | 40(3) | −9(3) | 17(2) | −8(3) |
| F(25) | 20(2) | 46(3) | 61(3) | 8(3) | 7(2) | 0(2) |
| F(26) | 55(3) | 25(3) | 70(4) | 8(3) | 17(3) | −7(2) |
| O(1) | 31(3) | 43(4) | 37(3) | 9(3) | 10(3) | 5(3) |

TABLE 9-continued

| | U11 | U22 | U33 | U23 | U13 | U12 |
|---|---|---|---|---|---|---|
| O(2) | 37(4) | 51(5) | 40(3) | −5(3) | 1(3) | −7(3) |
| O(21) | 30(3) | 34(4) | 31(3) | 0(3) | −8(2) | 1(3) |
| O(22) | 19(3) | 45(4) | 44(3) | −13(3) | −3(2) | −2(3) |
| O(40) | 72(5) | 83(7) | 72(5) | 6(5) | 14(4) | −2(5) |
| N(1) | 27(4) | 34(5) | 45(4) | 12(4) | −4(3) | −3(3) |
| N(2) | 20(3) | 39(5) | 49(5) | 4(4) | −2(3) | 0(3) |
| N(3) | 19(3) | 31(4) | 35(4) | 6(3) | −2(3) | 0(3) |
| N(4) | 28(4) | 56(6) | 50(5) | 16(4) | −7(3) | −7(4) |
| N(5) | 26(4) | 46(5) | 44(4) | −12(4) | 2(3) | 3(3) |
| N(21) | 27(4) | 35(5) | 37(4) | 13(4) | 2(3) | 6(3) |
| N(22) | 20(4) | 36(5) | 62(5) | 2(4) | 6(3) | 1(3) |
| N(23) | 21(3) | 28(4) | 45(4) | 7(3) | 10(3) | 5(3) |
| N(24) | 25(4) | 67(7) | 58(5) | 15(5) | −4(4) | −10(4) |
| N(25) | 23(4) | 59(6) | 35(4) | −18(4) | −5(3) | 4(3) |
| C(1) | 17(4) | 24(4) | 41(5) | 8(4) | −1(3) | 1(3) |
| C(2) | 18(4) | 33(5) | 44(5) | 3(4) | −2(3) | −2(3) |
| C(3) | 22(4) | 29(5) | 44(5) | 8(4) | 2(4) | −4(4) |
| C(4) | 27(5) | 34(5) | 44(5) | 3(4) | 1(4) | 2(4) |
| C(5) | 26(4) | 29(5) | 45(5) | 8(4) | 5(4) | 2(4) |
| C(6) | 27(4) | 33(5) | 41(5) | 6(4) | 3(4) | 1(4) |
| C(7) | 36(5) | 41(6) | 70(7) | 14(5) | 12(5) | −4(5) |
| C(8) | 26(4) | 35(5) | 31(4) | −3(4) | 0(3) | 5(4) |
| C(9) | 25(4) | 34(6) | 47(5) | −6(4) | −2(4) | −4(4) |
| C(10) | 30(5) | 43(6) | 44(5) | −1(5) | −4(4) | −5(4) |
| C(11) | 33(5) | 39(5) | 31(5) | 3(4) | −7(4) | 0(4) |
| C(12) | 24(4) | 30(5) | 34(4) | −4(4) | 6(3) | −6(3) |
| C(13) | 29(4) | 22(5) | 28(4) | −1(3) | −2(3) | −2(3) |
| C(14) | 41(5) | 33(6) | 85(8) | 9(6) | −9(5) | −5(5) |
| C(15) | 31(4) | 26(5) | 27(4) | 3(3) | −4(3) | 5(3) |
| C(16) | 42(5) | 35(5) | 30(4) | 10(4) | −8(4) | 11(4) |
| C(17) | 28(4) | 29(5) | 30(4) | 5(4) | −2(3) | 6(4) |
| C(21) | 22(4) | 29(5) | 42(5) | 4(4) | 7(4) | 0(3) |
| C(22) | 25(4) | 34(5) | 48(5) | 7(4) | 3(4) | 5(4) |
| C(23) | 25(4) | 31(5) | 42(5) | 1(4) | 4(4) | 9(4) |
| C(24) | 24(4) | 38(5) | 40(5) | 2(4) | 0(4) | 4(4) |
| C(25) | 29(5) | 22(5) | 54(6) | 3(4) | 9(4) | 1(4) |
| C(26) | 34(5) | 17(5) | 48(5) | 5(4) | 10(4) | 4(3) |
| C(27) | 28(5) | 30(6) | 69(7) | 2(5) | 8(5) | −2(4) |
| C(28) | 18(4) | 27(5) | 37(4) | 4(4) | 6(3) | 3(3) |
| C(29) | 30(4) | 20(5) | 39(5) | 0(4) | 4(4) | −5(3) |
| C(30) | 35(5) | 28(5) | 41(5) | −7(4) | 2(4) | −8(4) |
| C(31) | 32(4) | 26(5) | 37(5) | −2(4) | −2(4) | −3(4) |
| C(32) | 18(4) | 23(5) | 26(4) | −4(3) | 4(3) | −1(3) |
| C(33) | 22(4) | 25(5) | 32(4) | 1(3) | 3(3) | −3(3) |
| C(34) | 46(5) | 20(4) | 67(6) | −3(5) | 3(4) | −10(5) |
| C(35) | 21(4) | 33(5) | 31(4) | −3(4) | 0(3) | −3(3) |
| C(36) | 36(5) | 32(5) | 35(5) | −2(4) | 10(4) | −1(4) |
| C(37) | 21(4) | 28(5) | 30(4) | −2(3) | −2(3) | −1(3) |
| C(41) | 105(14) | 210(30) | 140(16) | −79(17) | 57(12) | −77(16) |

Example A

THP-1 RPS6 ELISA Assay

To measure the Phosphorylated Ribosomal Protein S6 (RPS6) in cell lysates, THP-1 cells (Human Acute Monocytic Leukemia) are purchased from ATCC (Manassas, Va.) and maintained in RPMI with 10% FBS (Gibco/Life Technologies, Carlsbad, Calif.). For the assay, THP-1 cells are serum starved overnight in RPMI, then plated in RPMI ($2\times10^5$ cells/well in 90 μL) into 96-well flat-bottom tissue culture treated plates (Corning, Corning, N.Y.), in the presence or absence of a concentration range of test compounds. Covered plates are incubated for 2 hours at 37° C., 5% $CO_2$ then treated with or without 10 nM MCP-1(MYBioSource, San Diego, Calif.) for 15 minutes at 37° C., 5% $CO_2$. Plates are centrifuged at 1600 RPM and supernatants are removed. Cells are lysed in Lysis Buffer (Cell Signaling, Danvers, Mass.) with Protease Inhibitor (Calbiochem/EMD, Germany), PMSF (Sigma, St Louis Mo.), HALTS (Thermo Fisher, Rockford, Ill.) for 30 min on wet ice. Cell lysates are frozen at −80° C. before testing. The lysates are tested in the Human/Mouse/Rat Phospho-RPS6 ELISA (R&D Systems, Inc. Minn, Minn.). The plate is measured using a microplate reader (SpectraMax M5—Molecular Devices, LLC Sunnyvale, Calif.) set to 450 nm with a wavelength correction of 540. IC$_{50}$ determination is performed by fitting the curve of inhibitor percent inhibition versus the log of the inhibitor concentration using the GraphPad Prism 5.0 software.

Example B

PI3K-γ Scintillation Proximity Assay

Materials

[γ-$^{33}$]ATP (10 mCi/mL) and Wheat Germ Agglutinin (WGA) YSi SPA Scintillation Beads was purchased from Perkin-Elmer (Waltham, Mass.). Lipid kinase substrate, D-myo-Phosphatidylinositol 4,5-bisphosphate (PtdIns(4,5)P2)D (+)-sn-1,2-di-O-octanoylglyceryl, 3-O-phospho linked (PIP2), CAS 204858-53-7, was purchased from Echelon Biosciences (Salt Lake City, Utah). PI3Kγ (p110γ) Recombinant Human Protein was purchased from Life technology (Grand Island, N.Y.). ATP, MgCl$_2$, DTT, EDTA, MOPS and CHAPS were purchased from SigmaAldrich (St. Louis, Mo.).

The kinase reaction was conducted in polystyrene 384-well Greiner Bio-one white plate from Thermo Fisher Scientific in a final volume of 25 μL. Inhibitors were first diluted serially in DMSO and added to the plate wells before the addition of other reaction components. The final concentration of DMSO in the assay was 2%. The PI3Kγ assay was carried out at room temperature in 20 mM MOPS, pH 6.7, 10 mM MgCl$_2$, 5 mM DTT and CHAPS 0.03%. Reactions were initiated by the addition of ATP, the final reaction mixture consisted of 20 μM PIP2, 2 μM ATP, 0.5 μCi [γ-$^{33}$P] ATP, 13 nM PI3Kγ. Reactions were incubated for 120 min and terminated by the addition of 40 μL SPA beads suspended in quench buffer: 163 mM potassium phosphate pH 7.8, 20% glycerol, 25 mM EDTA. The final concentration of SPA beads is 1.0 mg/mL. After the plate sealing, plates were shaken overnight at room temperature and centrifuged at 1500 rpm for 10 min, the radioactivity of the product was determined by scintillation counting on Topcount (Perkin-Elmer). IC$_{50}$ determination was performed by fitting the curve of percent of the solvent control activity versus the log of the inhibitor concentration using the GraphPad Prism 6.0 software.

Example C

PI3Kδ Scintillation Proximity Assay

Materials

[γ-$^{33}$P]ATP (10 mCi/mL) and Wheat Germ Agglutinin (WGA) YSi SPA Scintillation Beads was purchased from Perkin-Elmer (Waltham, Mass.). Lipid kinase substrate, D-myo-Phosphatidylinositol 4,5-bisphosphate (PtdIns(4,5)P2)D (+)-sn-1,2-di-O-octanoylglyceryl, 3-O-phospho linked (PIP2), CAS 204858-53-7, was purchased from Echelon Biosciences (Salt Lake City, Utah). PI3Kδ (p110δ/p85α) Recombinant Human Protein was purchased from Eurofins (St Charles, Mo.). ATP, MgCl$_2$, DTT, EDTA, MOPS and CHAPS were purchased from SigmaAldrich (St. Louis, Mo.).

The kinase reaction was conducted in polystyrene 384-well Greiner Bio-one white plate from Thermo Fisher Scientific in a final volume of 25 μL. Inhibitors were first diluted serially in DMSO and added to the plate wells before the addition of other reaction components. The final concentration of DMSO in the assay was 2%. The PI3Kδ assay was carried out at room temperature in 20 mM MOPS, pH 6.7, 10 mM MgCl$_2$, 5 mM DTT and CHAPS 0.03%. Reactions were initiated by the addition of ATP, the final reaction mixture consisted of 20 μM PIP2, 2 μM ATP, 0.5 μCi [γ-$^{33}$P] ATP, 3.4 nM PI3Kδ. Reactions were incubated for 120 min and terminated by the addition of 40 μL SPA beads suspended in quench buffer: 163 mM potassium phosphate pH 7.8, 20% glycerol, 25 mM EDTA. The final concentration of SPA beads is 1.0 mg/mL. After the plate sealing, plates were shaken overnight at room temperature and centrifuged at 1500 rpm for 10 min, the radioactivity of the product was determined by scintillation counting on Topcount (PerkinElmer). IC$_{50}$ determination was performed by fitting the curve of percent of the solvent control activity versus the log of the inhibitor concentration using the GraphPad Prism 6.0 software.

The compound of Examples 1, 5, 6 and 9 were tested in the assays described in Examples A, B and C, and found to have the IC$_{50}$ values shown in the Table A below.

TABLE A

| | IC$_{50}$ Values | | |
|---|---|---|---|
| Ex. No | PI3Kγ IC$_{50}$ (nM) | PI3Kδ IC$_{50}$ (nM) | PI3Kγ_THP1_RPS6_ELISA IC$_{50}$ (nM) |
| 1 | + | + | # |
| 5 | + | ++ | #### |
| 6 | + | ++ | ## |
| 9 | + | + | ## |

+ refers to IC$_{50}$ of ≤100 nM;
++ refers to IC$_{50}$ of ≤500 nM;
+++ refers to an IC$_{50}$ of <2000 nM;
++++ refers to an IC$_{50}$ of ≥2000 nM.
# refers to IC$_{50}$ of ≤100 nM;
## refers to IC$_{50}$ of ≤500 nM;
### refers to IC$_{50}$ of <1000 nM;
#### refers to an IC$_{50}$ of ≥1000 nM.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A crystalline form of the compound 2-(3-(8-amino-6-(trifluoromethyl)imidazo[1,2-a]pyrazin-3-yl)-4-methylphenyl)-3,3,3-trifluoro-2-hydroxypropanamide, wherein the crystalline form is selected from:
   Form IA having an X-ray powder diffraction pattern comprising 4 or more of the following peaks, in terms of 2θ: 8.6°±0.2°; 9.5°±0.2°; 10.3°±0.2°; 13.0°±0.2°; 13.6°±0.2°; 14.2°±0.2°; 14.9°±0.2°; 17.3°±0.2°; 19.2°±0.2°; 20.6°±0.2°; 24.0°±0.2°; and 28.7°±0.2°;
   Form IIA having an X-ray powder diffraction pattern comprising 4 or more of the following peaks, in terms of 2θ: 9.1°±0.2°; 11.1°±0.2°; 12.6°±0.2°; 13.5°±0.2°; 18.0°±0.2°; 19.0°±0.2°; 20.5°±0.2°; and 21.9°±0.2°; and
   Form IIIA having an X-ray powder diffraction pattern comprising 4 or more of the following peaks, in terms of 2θ: 8.1°±0.2°; 10.6°±0.2°; 13.5°±0.2°; 14.2°±0.2°; 16.4°±0.2°; 17.1°±0.2°; 17.9°±0.2°; 20.3°±0.2°; and 24.1°±0.2°.

2. The crystalline form of claim 1 that is Form IA, having an X-ray powder diffraction pattern substantially as shown in FIG. 1.

3. The crystalline form of claim 1 that is Form IA, having a DSC thermogram comprising an endothermic peak having a maximum at about 193° C.

4. The crystalline form of claim 1 that is Form IA, having a differential scanning calorimetry thermogram (DSC) substantially as shown in FIG. 2.

5. The crystalline form of claim 1 that is Form IA, having a thermogravimetric analysis (TGA) substantially as shown in FIG. 3.

6. The crystalline form of claim 1 that is Form IIA, having an X-ray powder diffraction pattern substantially as shown in FIG. 4.

7. The crystalline form of claim 1 that is Form I IA, having a DSC thermogram comprising an endothermic peak having a maximum at about 180° C.

8. The crystalline form of claim 1 that is Form IIA, having a differential scanning calorimetry thermogram (DSC) substantially as shown in FIG. 5.

9. The crystalline form of claim 1 that is Form IIA, having a thermogravimetric analysis (TGA) substantially as shown in FIG. 6.

10. The crystalline form of claim 1 that is Form IIIA, having an X-ray powder diffraction pattern substantially as shown in FIG. 7.

11. The crystalline form of claim 1 that is Form IIIA, having a DSC thermogram comprising an endothermic peak having a maximum at about 143° C.

12. The crystalline form of claim 1 that is Form IIIA, having a differential scanning calorimetry thermogram (DSC) substantially as shown in FIG. 8.

13. The crystalline form of claim 1 that is Form IIIA, having a thermogravimetric analysis (TGA) substantially as shown in FIG. 9.

14. The crystalline form of claim 1, which is substantially isolated.

15. A composition comprising the crystalline form of claim 1.

16. The composition of claim 15, wherein said composition further comprises at least one pharmaceutically acceptable carrier.

17. A method of inhibiting an activity of PI3Kγ kinase, comprising contacting the kinase with a crystalline form of claim 1.

18. The method of claim 17, wherein said crystalline form is a selective inhibitor for PI3Kγ over one or more of PI3Kα, PI3Kβ, and PI3Kδ.

19. A method of treating a disease or disorder in a patient, wherein said disease or disorder is associated with abnormal expression or activity of PI3Kγ kinase, comprising administering to said patient a therapeutically effective amount of a crystalline form of claim 1.

20. The method of claim 19, wherein the disease or disorder is an autoimmune disease or disorder, cancer, cardiovascular disease, or neurodegenerative disease.

21. A process of preparing a crystalline form of the compound 2-(3-(8-amino-6-(trifluoromethyl)imidazo[1,2-a]pyrazin-3-yl)-4-methylphenyl)-3,3,3-trifluoro-2-hydroxy-propanamide of claim 1, comprising dissolving the compound in a solvent to form a mixture and crystallizing the compound from the mixture.

22. The process of claim 21, wherein the solvent comprises isopropyl acetate.

23. The process of claim 22, wherein the solvent further comprises heptane.

24. The process of claim 21, wherein the process further comprises heating the mixture to a temperature of from about 70° C. to about 90° C.

25. The process of claim 24, wherein the process further comprises cooling the mixture to room temperature.

26. The process of claim 21, wherein the solvent comprises methanol.

27. The process of claim 21, wherein the process further comprises heating the mixture to a temperature of from about 50° C. to about 70° C.

28. The process of claim 27, wherein the process further comprises cooling the mixture to room temperature.

29. The crystalline form of claim 1, which is Form IA.

30. The crystalline form of claim 1, which is Form IIA.

31. The crystalline form of claim 1, which is Form IIIA.

* * * * *